US012751638B2

(12) United States Patent
Veszelei et al.

(10) Patent No.: US 12,751,638 B2
(45) Date of Patent: Oct. 6, 2026

(54) INTRAVASCULAR PRESSURE AND FLOW DATA DIAGNOSTIC SYSTEMS, DEVICES, AND METHODS

(71) Applicant: ST. JUDE MEDICAL COORDINATION CENTER BVBA, Zaventem (BE)

(72) Inventors: Eugen Veszelei, Uppsala (SE); Fredrik Lundgren, Uppsala (SE)

(73) Assignee: ST. JUDE MEDICAL COORDINATION CENTER BVBA, Zaventem (BE)

(*) Notice: Subject to any disclaimer, the term of this patent is extended or adjusted under 35 U.S.C. 154(b) by 905 days.

(21) Appl. No.: 18/086,317

(22) Filed: Dec. 21, 2022

(65) Prior Publication Data

US 2023/0132091 A1 Apr. 27, 2023

Related U.S. Application Data

(60) Division of application No. 16/402,789, filed on May 3, 2019, now Pat. No. 11,559,218, which is a (Continued)

(51) Int. Cl.
*A61B 5/027* (2006.01)
*A61B 5/00* (2006.01)
(Continued)

(52) U.S. Cl.
CPC .......... *A61B 5/027* (2013.01); *A61B 5/02055* (2013.01); *A61B 5/0215* (2013.01);
(Continued)

(58) Field of Classification Search
CPC ..... A61B 5/02055; A61B 5/026; A61B 5/029; A61B 5/02007; A61B 5/6851; A61B 2562/0247
See application file for complete search history.

(56) References Cited

U.S. PATENT DOCUMENTS 5,085,223 A 2/1992 Lars et al.
5,125,058 A 6/1992 Tenerz et al.
(Continued)

FOREIGN PATENT DOCUMENTS

CN 106264514 A 1/2017
EP 2 544 585 B1 1/2013
(Continued)

OTHER PUBLICATIONS

Pijls et al. ("Coronary Thermodilution to Assess Flow Reserve") Circulation. 2002; 105:2482-2486. (Year: 2002).*
(Continued)

*Primary Examiner* — Christian Jang
(74) *Attorney, Agent, or Firm* — Foley & Lardner LLP

(57) ABSTRACT

In part, the disclosure relates to computer-based methods, devices, and systems suitable for performing intravascular data analysis and measurement of various types of data such as pressure and flow data. The disclosure relates to probes and methods suitable for determining an event in a cardiac cycle such as flow threshold such as a peak flow, a fraction thereof, other intravascular parameters or a point in time during which peak flow or a change in one of the perimeters occurs. An exemplary probe includes one or more of a pressure sensor, a resistor, a flow sensor and can be used to generate diagnostic data based upon measured intravascular and other parameters. In part, the disclosure relates to methods and systems suitable for determining a coronary flow reserve value in response to one or more of intravascular pressure and flow data or data otherwise correlated therewith.

8 Claims, 37 Drawing Sheets

Related U.S. Application Data continuation of application No. 14/678,973, filed on Apr. 4, 2015, now Pat. No. 10,307,070.

(60) Provisional application No. 62/073,284, filed on Oct. 31, 2014, provisional application No. 61/975,424, filed on Apr. 4, 2014.

(51) Int. Cl.

| | |
|---|---|
| ***A61B 5/01*** | (2006.01) |
| ***A61B 5/02*** | (2006.01) |
| ***A61B 5/0205*** | (2006.01) |
| ***A61B 5/0215*** | (2006.01) |
| ***A61B 5/0245*** | (2006.01) |
| ***A61B 5/026*** | (2006.01) |
| ***A61B 5/029*** | (2006.01) |

(52) U.S. Cl.

CPC .......... *A61B 5/02158* (2013.01); *A61B 5/026* (2013.01); *A61B 5/029* (2013.01); *A61B 5/7225* (2013.01); *A61B 5/7278* (2013.01); *A61B 5/743* (2013.01); *A61B 5/7475* (2013.01); *A61B 5/01* (2013.01); *A61B 5/02007* (2013.01); *A61B 5/0245* (2013.01); *A61B 5/6851* (2013.01); *A61B 2560/0214* (2013.01); *A61B 2560/0223* (2013.01); *A61B 2560/0475* (2013.01); *A61B 2562/0247* (2013.01); *A61B 2562/0271* (2013.01)

(56) References Cited

U.S. PATENT DOCUMENTS

| | | | |
|---|---|---|---|
| 5,195,375 | A | 3/1993 | Tenerz et al. |
| 5,226,423 | A | 7/1993 | Tenerz et al. |
| 5,277,191 | A | 1/1994 | Hughes |
| 5,307,811 | A | 5/1994 | Sigwart et al. |
| 5,321,501 | A | 6/1994 | Swanson et al. |
| 5,346,508 | A | 9/1994 | Hastings |
| 5,459,570 | A | 10/1995 | Swanson et al. |
| 5,465,147 | A | 11/1995 | Swanson |
| 5,509,093 | A | 4/1996 | Miller et al. |
| 5,542,427 | A | 8/1996 | Åkerfeldt |
| 5,619,368 | A | 4/1997 | Swanson |
| RE35,648 | E | 11/1997 | Tenerz et al. |
| 5,694,946 | A | 12/1997 | Tenerz et al. |
| 5,748,598 | A | 5/1998 | Swanson et al. |
| 5,784,352 | A | 7/1998 | Swanson et al. |
| 5,868,684 | A | 2/1999 | Åkerfeldt et al. |
| 5,873,835 | A | 2/1999 | Hastings et al. |
| 5,938,624 | A | 8/1999 | Akerfeldt et al. |
| 5,965,355 | A | 10/1999 | Monis et al. |
| 6,089,103 | A | 7/2000 | Smith |
| 6,090,052 | A | 7/2000 | Akerfeldt et al. |
| 6,106,486 | A | 8/2000 | Tenerz et al. |
| 6,111,645 | A | 8/2000 | Tearney et al. |
| 6,112,598 | A | 9/2000 | Tenerz et al. |
| 6,129,674 | A | 10/2000 | Ovadia-Blechman et al. |
| 6,134,003 | A | 10/2000 | Tearney et al. |
| 6,142,958 | A | 11/2000 | Hammarstrom et al. |
| 6,160,826 | A | 12/2000 | Swanson et al. |
| 6,167,763 | B1 | 1/2001 | Tenerz et al. |
| 6,182,513 | B1 | 2/2001 | Stemme et al. |
| 6,191,862 | B1 | 2/2001 | Swanson et al. |
| 6,196,980 | B1 | 3/2001 | Akerfeldt et al. |
| 6,224,624 | B1 | 5/2001 | Lasheras et al. |
| 6,241,651 | B1 | 6/2001 | Smith et al. |
| 6,248,083 | B1 | 6/2001 | Smith et al. |
| 6,264,673 | B1 | 7/2001 | Egnelov et al. |
| 6,282,011 | B1 | 8/2001 | Tearney et al. |
| 6,312,380 | B1 | 11/2001 | Hoek et al. |
| 6,336,906 | B1 | 1/2002 | Hammarstroem et al. |
| 6,343,514 | B1 | 2/2002 | Smith |
| 6,409,677 | B1 | 6/2002 | Tulkki |
| 6,421,164 | B2 | 7/2002 | Tearney et al. |
| 6,425,911 | B1 | 7/2002 | Akerfeldt et al. |
| 6,431,010 | B1 | 8/2002 | Joffe |
| 6,445,939 | B1 | 9/2002 | Swanson et al. |
| 6,461,301 | B2 | 10/2002 | Smith |
| 6,477,233 | B1 | 11/2002 | Ribbing et al. |
| 6,485,413 | B1 | 11/2002 | Boppart et al. |
| 6,501,551 | B1 | 12/2002 | Tearney et al. |
| 6,503,266 | B1 | 1/2003 | Sjoegren et al. |
| 6,508,828 | B1 | 1/2003 | Akerfeldt et al. |
| 6,517,481 | B2 | 2/2003 | Hoek et al. |
| 6,546,804 | B2 | 4/2003 | Stemme et al. |
| 6,552,796 | B2 | 4/2003 | Magnin et al. |
| 6,564,087 | B1 | 5/2003 | Pitris et al. |
| 6,565,514 | B2 | 5/2003 | Svanerudh et al. |
| 6,570,659 | B2 | 5/2003 | Schmitt |
| 6,596,012 | B2 | 7/2003 | Akerfeldt et al. |
| 6,615,067 | B2 | 9/2003 | Hoek et al. |
| 6,615,667 | B2 | 9/2003 | Smith |
| 6,663,653 | B2 | 12/2003 | Akerfeldt |
| 6,672,172 | B2 | 1/2004 | Tulkki et al. |
| 6,682,489 | B2 | 1/2004 | Tenerz et al. |
| 6,692,446 | B2 | 2/2004 | Hoek |
| 6,706,004 | B2 | 3/2004 | Tearney et al. |
| 6,712,837 | B2 | 3/2004 | Åkerfeldt et al. |
| 6,754,608 | B2 | 6/2004 | Svanerudh et al. |
| 6,786,915 | B2 | 9/2004 | Akerfeldt et al. |
| 6,827,727 | B2 | 12/2004 | StåLemark et al. |
| 6,860,895 | B1 | 3/2005 | Akerfeldt et al. |
| 6,879,851 | B2 | 4/2005 | Mcnamara et al. |
| 6,891,984 | B2 | 5/2005 | Petersen et al. |
| 6,908,442 | B2 | 6/2005 | Von Malmborg et al. |
| 6,926,674 | B2 | 8/2005 | Tenerz et al. |
| 6,929,655 | B2 | 8/2005 | Egnelov et al. |
| 6,939,363 | B2 | 9/2005 | Akerfeldt |
| 6,976,965 | B2 | 12/2005 | Corl et al. |
| 6,993,974 | B2 | 2/2006 | Tenerz et al. |
| 7,006,858 | B2 | 2/2006 | Silver et al. |
| 7,011,636 | B2 | 3/2006 | Tenerz |
| 7,011,678 | B2 | 3/2006 | Tenerz et al. |
| 7,021,152 | B2 | 4/2006 | Tenerz |
| 7,044,916 | B2 | 5/2006 | Tenerz et al. |
| 7,073,509 | B2 | 7/2006 | Tenerz et al. |
| 7,094,209 | B2 | 8/2006 | Egnelov et al. |
| 7,097,620 | B2 * | 8/2006 | Corl ...................... G01L 19/141 600/488 |
| 7,134,994 | B2 | 11/2006 | Alpert et al. |
| 7,135,032 | B2 | 11/2006 | Åkerfeldt |
| 7,208,333 | B2 | 4/2007 | Flanders et al. |
| 7,222,539 | B2 | 5/2007 | Tulkki |
| 7,231,243 | B2 | 6/2007 | Tearney et al. |
| 7,241,286 | B2 | 7/2007 | Atlas |
| 7,263,894 | B2 | 9/2007 | Tenerz |
| RE39,863 | E | 10/2007 | Smith |
| 7,285,097 | B2 | 10/2007 | Tenerz et al. |
| 7,326,088 | B2 | 2/2008 | Tulkki |
| 7,329,270 | B2 | 2/2008 | Åkerfeldt et al. |
| 7,331,236 | B2 | 2/2008 | Smith et al. |
| 7,343,811 | B2 | 3/2008 | Tenerz et al. |
| 7,414,779 | B2 | 8/2008 | Huber et al. |
| 7,415,049 | B2 | 8/2008 | Flanders et al. |
| 7,445,625 | B2 | 11/2008 | Åkerfeldt |
| 7,450,989 | B2 | 11/2008 | Svanerudh |
| 7,472,601 | B1 | 1/2009 | Tenerz et al. |
| 7,625,366 | B2 | 12/2009 | Atlas |
| 7,637,921 | B2 | 12/2009 | Åkerfeldt et al. |
| 7,645,233 | B2 | 1/2010 | Tulkki et al. |
| 7,654,963 | B2 | 2/2010 | Egnelov et al. |
| 7,724,148 | B2 | 5/2010 | Samuelsson et al. |
| 7,775,988 | B2 | 8/2010 | Pijls |
| 7,775,992 | B2 | 8/2010 | Von Malmborg et al. |
| 7,813,609 | B2 | 10/2010 | Petersen et al. |
| 7,848,791 | B2 | 12/2010 | Schmitt et al. |
| 7,916,387 | B2 | 3/2011 | Schmitt |
| 7,931,603 | B2 | 4/2011 | Von Malmborg et al. |
| 7,935,060 | B2 | 5/2011 | Schmitt et al. |
| 7,938,846 | B2 | 5/2011 | Åkerfeldt et al. |
| 7,946,997 | B2 | 5/2011 | Hubinette |
| 7,967,761 | B2 | 6/2011 | Smith |

(56) References Cited

U.S. PATENT DOCUMENTS

| | | | |
|---|---|---|---|
| 7,998,089 | B2 | 8/2011 | Smith |
| 8,038,628 | B2 | 10/2011 | Von Malmborg et al. |
| 8,057,421 | B2 | 11/2011 | Akingba |
| 8,088,143 | B2 | 1/2012 | Åkerfeldt |
| 8,109,889 | B2 | 2/2012 | Von Malmborg et al. |
| 8,116,605 | B2 | 2/2012 | Petersen et al. |
| 8,187,195 | B2 | 5/2012 | Tulkki |
| 8,206,377 | B2 | 6/2012 | Petroff |
| 8,216,151 | B2 | 7/2012 | Smith |
| 8,216,434 | B2 | 7/2012 | Hsiai et al. |
| 8,308,758 | B2 | 11/2012 | Åkerfeldt |
| 8,323,215 | B2 | 12/2012 | Von Malmborg et al. |
| 8,325,419 | B2 | 12/2012 | Schmitt |
| 8,358,461 | B2 | 1/2013 | Huber et al. |
| 8,398,675 | B2 | 3/2013 | Egnelov |
| 8,403,868 | B2 | 3/2013 | Von Malmborg et al. |
| 8,412,312 | B2 | 4/2013 | Judell et al. |
| 8,449,468 | B2 | 5/2013 | Petersen et al. |
| RE44,297 | E | 6/2013 | Åkerfeldt et al. |
| 8,469,944 | B2 | 6/2013 | Mahlin |
| 8,478,384 | B2 | 7/2013 | Schmitt et al. |
| 8,478,387 | B2 | 7/2013 | Xu |
| 8,503,844 | B2 | 8/2013 | Petersen et al. |
| 8,579,825 | B2 | 11/2013 | Tenerz et al. |
| 8,581,643 | B1 | 11/2013 | Schmitt |
| 8,582,109 | B1 | 11/2013 | Schmitt |
| 8,582,619 | B2 | 11/2013 | Adler |
| 8,582,934 | B2 | 11/2013 | Adler et al. |
| 8,641,633 | B2 | 2/2014 | Smith |
| 8,652,166 | B2 | 2/2014 | Åkerfeldt |
| 8,687,201 | B2 | 4/2014 | Adler |
| 8,696,584 | B2 | 4/2014 | Kassab |
| 8,702,613 | B2 | 4/2014 | Kassab |
| 8,715,200 | B2 | 5/2014 | Pijls |
| 8,734,366 | B2 | 5/2014 | Egnelov et al. |
| 8,786,336 | B1 | 7/2014 | Schmitt |
| 8,802,124 | B2 | 8/2014 | Tenerz et al. |
| 8,831,321 | B1 | 9/2014 | Elbasiony |
| 8,948,228 | B2 | 2/2015 | Adler |
| 8,953,911 | B1 | 2/2015 | Xu et al. |
| 9,149,230 | B2 | 10/2015 | Caron et al. |
| 9,198,563 | B2 | 12/2015 | Ferren et al. |
| 9,295,842 | B2 | 3/2016 | Ghaffari et al. |
| 10,307,070 | B2 | 6/2019 | Veszelei et al. |
| 10,835,137 | B2 | 11/2020 | Sette et al. |
| 10,835,211 | B2 | 11/2020 | Sette |
| 2002/0161351 | A1 | 10/2002 | Samson et al. |
| 2003/0032886 | A1 | 2/2003 | Dgany et al. |
| 2003/0033095 | A1 | 2/2003 | Svanerudh et al. |
| 2003/0216621 | A1 | 11/2003 | Alpert et al. |
| 2004/0167385 | A1 | 8/2004 | Rioux et al. |
| 2005/0187487 | A1 | 8/2005 | Azizkhan et al. |
| 2005/0201662 | A1 | 9/2005 | Petersen et al. |
| 2006/0009817 | A1 | 1/2006 | Tulkki |
| 2006/0052700 | A1 | 3/2006 | Svanerudh |
| 2006/0095065 | A1 | 5/2006 | Tanimura et al. |
| 2006/0142786 | A1 | 6/2006 | Mathisen et al. |
| 2006/0161224 | A1 | 7/2006 | Samuelsson et al. |
| 2006/0178586 | A1 | 8/2006 | Dobak, III |
| 2006/0205910 | A1 | 9/2006 | Asplund et al. |
| 2006/0211839 | A1 | 9/2006 | Asplund et al. |
| 2006/0235314 | A1 | 10/2006 | Migliuolo et al. |
| 2007/0255145 | A1 | 11/2007 | Smith et al. |
| 2007/0299542 | A1 | 12/2007 | Mathisen et al. |
| 2008/0077050 | A1 | 3/2008 | Von Malmborg et al. |
| 2008/0139951 | A1 | 6/2008 | Patangay et al. |
| 2008/0197750 | A1 | 8/2008 | Katardjiev et al. |
| 2008/0302675 | A1 | 12/2008 | Hsiai et al. |
| 2008/0306494 | A1 | 12/2008 | Magnusson et al. |
| 2009/0030450 | A1 | 1/2009 | Preinitz et al. |
| 2009/0036920 | A1 | 2/2009 | Preinitz et al. |
| 2009/0069859 | A1 | 3/2009 | Whinnett et al. |
| 2009/0118643 | A1 | 5/2009 | Smith et al. |
| 2009/0174931 | A1 | 7/2009 | Huber et al. |
| 2009/0282437 | A1 | 11/2009 | Malec et al. |
| 2009/0306520 | A1 | 12/2009 | Schmitt et al. |
| 2010/0076320 | A1 | 3/2010 | Petersen et al. |
| 2010/0109104 | A1* | 5/2010 | Tiensuu .............. G01L 19/0092 257/419 |
| 2010/0286537 | A1 | 11/2010 | Pijls |
| 2010/0319345 | A1 | 12/2010 | Sinan et al. |
| 2011/0071404 | A1 | 3/2011 | Schmitt et al. |
| 2011/0071407 | A1 | 3/2011 | Hubinette et al. |
| 2011/0085977 | A1* | 4/2011 | Rosenmeier ........... A61K 51/04 424/9.1 |
| 2011/0101207 | A1 | 5/2011 | Schmitt |
| 2011/0157686 | A1 | 6/2011 | Huber et al. |
| 2011/0190586 | A1 | 8/2011 | Kemp |
| 2011/0228280 | A1 | 9/2011 | Schmitt et al. |
| 2012/0101409 | A1 | 4/2012 | Von Malmborg et al. |
| 2012/0220898 | A1 | 8/2012 | Tulkki |
| 2012/0238869 | A1 | 9/2012 | Schmitt et al. |
| 2012/0250028 | A1 | 10/2012 | Schmitt et al. |
| 2012/0278008 | A1 | 11/2012 | Davies et al. |
| 2012/0310081 | A1 | 12/2012 | Adler et al. |
| 2012/0316419 | A1 | 12/2012 | Chevalier |
| 2013/0010303 | A1 | 1/2013 | Petersen et al. |
| 2013/0012811 | A1 | 1/2013 | Schmitt et al. |
| 2013/0023761 | A1 | 1/2013 | Petroff |
| 2013/0046190 | A1 | 2/2013 | Davies |
| 2013/0051728 | A1 | 2/2013 | Petroff et al. |
| 2013/0072805 | A1 | 3/2013 | Schmitt et al. |
| 2013/0090555 | A1 | 4/2013 | Kassab |
| 2013/0131523 | A1 | 5/2013 | Suchecki et al. |
| 2013/0190633 | A1 | 7/2013 | Dorando et al. |
| 2013/0246034 | A1* | 9/2013 | Sharma .................. G16H 50/50 703/11 |
| 2013/0310698 | A1 | 11/2013 | Judell et al. |
| 2013/0345574 | A1 | 12/2013 | Davies et al. |
| 2014/0018669 | A1 | 1/2014 | Xu |
| 2014/0024931 | A1 | 1/2014 | Winston et al. |
| 2014/0039276 | A1 | 2/2014 | Hattangadi et al. |
| 2014/0094697 | A1 | 4/2014 | Petroff et al. |
| 2014/0114182 | A1 | 4/2014 | Petersen et al. |
| 2014/0135633 | A1 | 5/2014 | Anderson et al. |
| 2014/0136477 | A1 | 5/2014 | Young et al. |
| 2014/0142427 | A1 | 5/2014 | Petroff |
| 2014/0142432 | A1 | 5/2014 | Hutchins et al. |
| 2014/0142436 | A1 | 5/2014 | Hutchins et al. |
| 2014/0176554 | A1 | 6/2014 | Cohen et al. |
| 2014/0180030 | A1 | 6/2014 | Dorando |
| 2014/0180035 | A1 | 6/2014 | Anderson |
| 2014/0180072 | A1 | 6/2014 | Davies et al. |
| 2014/0180140 | A1 | 6/2014 | Alpert |
| 2014/0180268 | A1 | 6/2014 | Whiseant |
| 2014/0180702 | A1 | 6/2014 | Mansker et al. |
| 2014/0180703 | A1 | 6/2014 | Mansker et al. |
| 2014/0180721 | A1 | 6/2014 | Cheline et al. |
| 2014/0181716 | A1 | 6/2014 | Merritt et al. |
| 2014/0181717 | A1 | 6/2014 | Lahti et al. |
| 2014/0187929 | A1 | 7/2014 | Schmitt et al. |
| 2014/0188503 | A1 | 7/2014 | Balignasay et al. |
| 2014/0188513 | A1 | 7/2014 | Balignasay et al. |
| 2014/0188514 | A1 | 7/2014 | Balignasay et al. |
| 2014/0188515 | A1 | 7/2014 | Mansker et al. |
| 2014/0194757 | A1 | 7/2014 | 'T Hooft et al. |
| 2014/0207008 | A1 | 7/2014 | Davies |
| 2014/0218742 | A1 | 8/2014 | Adler |
| 2014/0236118 | A1 | 8/2014 | Unser et al. |
| 2014/0240713 | A1 | 8/2014 | Kemp |
| 2014/0249407 | A1 | 9/2014 | Adler et al. |
| 2014/0266577 | A1 | 9/2014 | Anderson et al. |
| 2014/0268167 | A1 | 9/2014 | Friedman et al. |
| 2014/0276011 | A1 | 9/2014 | Schmitt et al. |
| 2014/0276136 | A1 | 9/2014 | Hattangadi et al. |
| 2014/0276137 | A1 | 9/2014 | Burnett et al. |
| 2014/0276139 | A1 | 9/2014 | Burkett et al. |
| 2014/0276143 | A1 | 9/2014 | Corl |
| 2014/0276684 | A1 | 9/2014 | Huennekens et al. |
| 2014/0276687 | A1 | 9/2014 | Goodman et al. |
| 2014/0309536 | A1 | 10/2014 | Douk et al. |
| 2014/0336476 | A1 | 11/2014 | Li |
| 2014/0379269 | A1 | 12/2014 | Schmitt |
| 2015/0025330 | A1 | 1/2015 | Davies et al. |

(56) References Cited

U.S. PATENT DOCUMENTS

| | | | |
|---|---|---|---|
| 2015/0025398 | A1 | 1/2015 | Davies et al. |
| 2015/0080749 | A1 | 3/2015 | Anderson et al. |
| 2019/0046212 | A1 | 2/2019 | Unser |
| 2019/0082975 | A1 | 3/2019 | Sano et al. |
| 2019/0298187 | A1 | 10/2019 | Hendriks et al. |
| 2021/0038157 | A1 | 2/2021 | Sette |
| 2021/0052173 | A1 | 2/2021 | Desjardins et al. |

FOREIGN PATENT DOCUMENTS

| | | | |
|---|---|---|---|
| EP | 3 331 437 | B1 | 6/2018 |
| GB | 2 479 340 | | 10/2011 |
| JP | 07-313475 | | 12/1995 |
| JP | H08-266491 | | 10/1996 |
| JP | H11-318904 | A | 11/1999 |
| JP | 2000-050249 | A | 2/2000 |
| JP | 2000-083915 | A | 3/2000 |
| JP | 2000-504249 | A | 4/2000 |
| JP | 2000-513242 | A | 10/2000 |
| JP | 2001-245862 | A | 9/2001 |
| JP | 2003-033329 | A | 2/2003 |
| JP | 2003-525067 | A | 8/2003 |
| JP | 2006-513731 | A | 4/2006 |
| JP | 2012-501807 | A | 1/2012 |
| JP | 2014-504923 | A | 2/2014 |
| JP | 2014-533602 | A | 12/2014 |
| WO | WO-97/27802 | A1 | 8/1997 |
| WO | WO-00/53081 | A1 | 9/2000 |
| WO | WO-01/54576 | A1 | 8/2001 |
| WO | WO-2004/026128 | A1 | 4/2004 |
| WO | WO-2012/093266 | A1 | 7/2012 |
| WO | WO-2013/028612 | A2 | 2/2013 |
| WO | WO-2013/028613 | A1 | 2/2013 |
| WO | WO-2013/028613 | A2 | 2/2013 |
| WO | WO-2013/061280 | A1 | 5/2013 |
| WO | WO-2013/138428 | A1 | 9/2013 |
| WO | WO-2015/060252 | A1 | 4/2015 |
| WO | WO-2015/125289 | A1 | 8/2015 |

OTHER PUBLICATIONS

Office Action issued in Canadian Application No. 3,186,992, mailed Jun. 19, 2024.

Office Action issued in Canadian Application No. 3,187,018, mailed Jun. 19, 2024.

Extended European Search Report issued in EP Application No. 24156335.2, mailed Jun. 18, 2024.

Japanese Office Action issued in JP Application No. 2023-139464, mailed Jun. 25, 2024.

Office Action issued in connection with Japanese Application No. 2022-037713, dated Feb. 28, 2023.

Office Action issued in Canadian Application No. 3,186,992, mailed Jul. 18, 2025.

European Communication pursuant to Article 94(3) EPC issued in EP Application No. 24156335.2, mailed Apr. 4, 2025.

Chinese Office Action & Search Report issued in connection with CN 202010845974.5 dated Feb. 22, 2024.

Abe et al., "Diastolic Fractional Flow Reserve to Assess the Functional Severity of Moderate Coronary Artery Stenoses: Comparison with Fractional Flow Reserve and Coronary Flow Velocity Reserve", Circulation 2000; 102:2365-2370.

Annex to Form PCT/ISA/206 of International Patent Application No. PCT/IB2015//000675 mailed Aug. 31, 2015 (5 pages).

Brosh et al., "Pulse Transmission Coefficient: A Novel Nonhyperemic Index for Physiologic Assessment of Procedural Success Following Percutaneous Coronary Interventions", Catherization and Cardiovascular Interventions 61:95-102 2004).

Brosh et al., "Pulse Transmission Coefficient: A Novel Nonhyperemic Parameter for Assessing the Physiological Significance of Coronary Artery Stenoses", JACC 39:6; 1012-9, Mar. 20, 2002.

Canadian Office Action, Application No. 2,944,114, May 3, 2021,4 pages.

Candreva et al., TCT-256 A Novel Thermoconvection-Equipped Microcatheter (PhysioCath) for Coronary Blood Velocity and Pressure Measurement: Preliminary Experience, Journal of the American College of Cardiology, vol. 78, Issue 19, Nov. 9, 2021, pp. B104-B105.

El Farissi et al., Safety of Selective Intracoronary Hypothermia During Primary Percutaneous Coronary Intervention in Patients With Anterior STEMI, JACC. Cardiovascular interventions, vol. 14, Issue 18, Sep. 27, 2021, pp. 2047-2055.

English translation of JP 2017-503195 Office Action dated Jul. 3, 2018 (4 pages).

Floros et al., First-in-Human Clinical Application of the Medyria TrackCath System in Endovascular Repair of Complex Aortic Aneurysms (ACCESS Trial): A Prospective Multicenter Single-Arm Clinical Trial, Journal of Endovascular therapy : an Official Journal of the International Society of Endovascular Specialists, vol. 28, Issue 6, Dec. 2021, pp. 914-926.

Floros et al., First-in-man Clinical Application of the Trackcath System in Endovascular Repair of Aortic Aneurysms—A Prospective Multi-centre Clinical Trial, European Journal of Vascular and Endovascular Surgery, vol. 58, Issue 6, Dec. 2019, pp. e723-e724.

Floros et al., First-in-Man Clinical Application of the TrackCath System in Endovascular Repair of Aortic Aneurysms—A Prospective Multicenter Clinical Trial, Journal of Vascular Surgery, vol. 7, Issue 5, Nov. 2019, pp. e201-e202.

Guagliumi et al., Volumetric assessment of lesion severity with optical coherence tomography: relationship with fractional flow reserve, EuroIntervention 2013; 8: 1172-1181.

Holmes et al., "Coronary Pressure Notch: An Early Non-hyperemic Visual Indicator of the Physiologic Significance of a Coronary Artery Stenosis", JIC Invasivecardiology.com 16:11, 617-620 {Nov. 2004).

Japanese Office Action and English translation, Application No. 2020-183508, Sep. 14, 2021, 6 pages.

Mamas et al., "Resting Pd/Pa Measured with Intracoronary Pressure Wire Strongly Predicts Fractional Flow Reserve", JIC invasivecardiology.com 22:6, 260-265 (Jun. 2010).

Marques et al., "The Diastolic Flow-pressure Gradient Relation in Coronary Stenoses in Humans", JACC 39:10, 1630-6, May 15, 2002.

Parodi et al., "Patient-Specific Prediction of Coronary Plaque Growth from CTA Angiography: A Multiscale Model for Plaque Formation and Progression", IEEE Transactions on Information Technology in Biomedicine 16:Sep. 5, 2012, pp. 952-965.

Rancic et al., TrackCath System: New Approach to Cannulation, Journal of Vascular Surgery, vol. 68, Issue 5, Nov. 2018, pp. e137-e138.

Rancic et al., Trackcath System; New Approach to Cannulation, European Journal of Vascular and Endovascular Surgery, vol. 58, Issue 6, Dec. 2019, pp. e523-e524.

Saratizis et al., Interwoven Nitinol Stents versus Drug Eluting Stents in the Femoro-Popliteal Segment: A Propensity Matched Analysis, European Journal of Vascular and Endovascular Surgery, Nov. 2019, vol. 58, pp. 719-727.

Saratzis et al., Supervised Exercise Therapy and Revascularization for Intermittent Claudication, Network Meta-Analysis of Randomized Controlled Trials, JACC Cardiovascular Interventions, Jun. 24, 2019, vol. 12, No. 12, pp. 1125-1136.

Schmidt et al., Retrograde Tibioperoneal Access for Complex Infrainguinal Occlusions: Short- and Long-Term Outcomes of 554 Endovascular Interventions, JACC: Cardiovascular Interventions, vol. 12, Issue 17, Sep. 9, 2019, pp. 1714-1726.

Sette, A Novel Flow and Pressure Catheter for Complete Interventional Cardiology Physiology Management, European Heart Journal, vol. 42, Issue Suppl 1, Oct. 2021, p. 1198.

Smilowitz et al., Variability of Discharge Medical Therapy for Secondary Prevention Among Patients with Myocardial Infarction with Non-Obstructive Coronary Arteries (MINOCA) in the United States, Plos One, vol. 16, Issue 8, Aug. 2, 2021, 8 pages.

(56) References Cited

OTHER PUBLICATIONS

Taylor et al., "Computational Fluid Dynamics Applied to Cardiac Computed Tomography for Noninvasive Quantification of Fractional Flow Reserve", J Am Coll Cardiol 61:22, 2013 pp. 2233-2241.
Tenino et al., "Fractional Flow Reserve versus Angiography for Guiding Percutaneous Coronary Intervention", N Engl J Med 360:3, NEJM.org, Jan. 15, 2009 pp. 213-224.
Tu et al., "Fractional Flow Reserve Calculation From 3-Dimensional Quantitative Coronary Angiography and TIMI Frame Count A Fast Computer Model to Quantify the Functional Significance of Moderately Obstructed Coronary Arteries", JACC: Cardiovascular Interventions 7:7, Jul. 2014 pp. 768-777.
Van der Horst, "Guidewire-mounted thermal sensors to assess coronary hemodynamics", ISBN: 978-90-386-3142-4, Copyright 2012 by A. van der Horst, 174 pages.
Van der Sligte, "Radi Analyzer and Pressure Wire for Constant Temperature Anemometry", BMTE 09.23, Jun. 2009, 38 pages.
Volcano FFR Option Operator's Manual For Use with Volcano Imaging and Pressure Systems, Software Version Level 3.4.X, Apr. 2014 (64 pages).
Office Action issued in Canadian Application No. 3,187,018, mailed Sep. 5, 2025.
Chinese Office Action issued in Chinese Application No. 202010845974.5 on Jul. 31, 2024.
Office Action in JP Application No. 2025-001721, dated Dec. 2, 2025, 6 pgs. (with translation).
European Examination Report issued in Application No. 24156335.2, mailed Jul. 17, 2026 (6 pages).

* cited by examiner

INTRAVASCULAR PRESSURE AND FLOW DATA DIAGNOSTIC SYSTEMS, DEVICES, AND METHODS

CROSS REFERENCE TO RELATED APPLICATIONS

This application is a Divisional Application of U.S. application Ser. No. 16/402,789 filed on May 3, 2019 which is a Continuation Application of U.S. application Ser. No. 14/678,973 filed on Apr. 4, 2015, now U.S. Pat. No. 10,307,070, which claims priority to U.S. Provisional Patent Application No. 61/975,424 filed on Apr. 4, 2014 and U.S. Provisional Patent Application No. 62/073,284 filed on Oct. 31, 2014. The disclosures of these applications are incorporated herein by reference in their entireties.

FIELD OF THE INVENTION

The disclosure relates generally to intravascular measurements such as pressure, temperature and flow measurements and related diagnostic methods and devices.

BACKGROUND

Sensor and guide wire assemblies can be used to collect intravascular data using measurement sensors located at or near their distal tips. These devices are typically used in applications to measure internal properties of tissues and fluids such as blood pressure. Sensor and guide wire assemblies may be introduced into arteries, veins or other body organs either by themselves or through catheters that have been previously positioned within a patient. These assemblies can be used to measure pressure and other parameters.

For example, such assemblies can be used along with one or more pressure sensing devices such as a delivery catheter to measure a Fractional Flow Reserve (FFR) using pressure data. In addition, Coronary Flow Reserve (CFR) measurements can be performed using a thermodilution-based approach. In such an approach a CFR value is obtained by injecting a cold saline solution into the coronary artery of interest and using a temperature sensor to measure the onset of cold saline injection into the artery to the return of the temperature to a specific level.

The thermodilution method has a number of constraints. The stated accuracy of this method is as low as +/−30%. Further, the procedure is cumbersome/time-consuming, requiring a number of saline injections of a certain quality to produce enough data for the system software to calculate the CFR value. Performing FFR and CFR is performed as two separate methods given the nature of the thermodilution system, saline delivery, and subsequent measurements required.

FFR is used to provide a measure of stenosis severity in a coronary artery. The typical method to determine FFR is to measure a pressure drop in the coronary arteries at hyperemia. A hyperemia inducing substance is injected to create an increase in blood flow in the coronary system for a controlled period. The pressure drop is measured during this time period and used as an input in determining FFR.

In part, the disclosure relates to methods, systems and devices suitable for measuring FFR, CFR, and other values and generating diagnostic outputs that overcome some of the challenges with existing methods.

SUMMARY

In part, the disclosure relates to methods, systems and devices to simultaneously perform intravascular pressure measurements while measuring blood flow values or parameters correlated with such flow. These embodiments can be based upon hot-film or hot-wire anemometry. Hot-film or hot-wire anemometry is a method of measuring the cooling effect of a flowing fluid (or gas) on a heated surface. When using a sensor as a hot-film anemometer the sensor is heated by electrical current, and the cooling effect of the flowing blood is measured by sampling the voltage across a resistor. The voltage across the resistor can be measured as well as other resistances, currents, and electrical parameters and signals. These measured values can be correlated with a flow parameter. In one embodiment, the voltage can be used in two related anemometry methods: Constant Temperature anemometry (CTA) and Constant Excitation Voltage (CVEX) anemometry.

In one embodiment, a semiconductor based sensor that includes a first temperature sensitive resistor and a second temperature sensitive resistor is used as part of a pressure sensing intravascular device. Further, at least one of the first and second resistors is also pressure sensitive. The sensor can be delivered via a guide wire and can be used to measure pressure before and after a candidate stenosis while simultaneously obtaining flow data, pressure data or temperature data based upon changes in excitation voltage, current, temperature or other sensor parameters. Various control systems and calibration methods can be used to support such pressure and flow measurements.

In one embodiment, the disclosure relates to using a digital control system while performing simultaneous pressure and flow measurements using a semiconductor-based pressure sensor. The digital control system overcomes certain deficiencies of an analog control system. Specifically, some advantages of the digital control system include calibration features and user specified temperature selection features. The digital system also can be used to improve the signal relative to noise levels. The calibration features include reading information digitally encoded on a memory device associated with a given sensing probe and regulating control system stages in response thereto. The memory device can be attached to the probe such as a PROM, an EEPROM, an RFID, or other suitable memory storage device.

The temperature selection features include automatically obtaining the temperature of the blood vessel using one or more sensors and then changing an electrical property of the sensing system. This change to current, voltage, impedance, or another parameter is in response to a user specified temperature above the temperature of flowing blood such as an over-temperature or sensing temperature range. The over-temperature or sensing temperature range provides a range or value which can be reduced through cooling. The temperature reduction can be measured as a result of flowing blood. Alternatively, the degree to which an electrical property, such as voltage or current, needs to increase to maintain a constant over-temperature or sensing temperature range can be measured and correlated with blood flow. Thus, the over-temperature can be constant or can be a range which varies based on cooling.

In one embodiment, the disclosure relates to graphical user interfaces and probe interface or processing systems or display systems or integrated cardiology display systems (ICD) (each either separately or together, generally referred to as a "measurement system") that are in electronic communication with a guide wire-based probe simultaneously relaying pressure and flow related data thereto. In one embodiment, a suitable measurement system such as an ICD can include, without limitation, a RadiAnalyzer system, a RadiAnalyzer Xpress system, a Quantien system, an Aeris system, a Prestige guide wire-based probe system, CombοMap® Pressure and Flow System, and other intravascular pressure sensing or FFR determining devices and systems. In one embodiment, the measurement system and the probe interface or processing systems and display system are the same device or collection of devices.

In one embodiment, the interface device receives signals from the guide wire-based probe indicative of flow and pressure at one or more locations along a blood vessel. Prior to being introduced into a blood vessel, the guide wire-based probe sensor is disposed in a catheter. Further, prior to being introduced into a lumen of a blood vessel, the system obtains a zero flow reference value from inside the catheter. This zero flow reference can also be used as an input when calibrating the guide wire-based probe. Atmospheric pressure can also be used as a zero point during sensor calibration.

The timing of data collection and selection of the controlled environment in which data collection is performed provides a zero point or origin relative to which other flow measurements and/or pressure measurements can be evaluated. The zero point or calibration point can be used with other parameters and a transfer function to transform guide wire-based probe signal data to flow data suitable for display and subsequent data analysis using one or more processors in a measurement system.

In one embodiment, the transfer function T(x) is of the form T(x)=a+b*ln(x), wherein T(x) yields a temperature value in response to a flow value x. In one embodiment, the transfer function T(x) is of the form T(x)=a+b*ln(x), wherein T(x) yields an excitation voltage or electrical power value in response to a flow value x. The flow value x is a flow velocity in one embodiment. In another embodiment, the flow value x is flow rate. In one embodiment, the transfer function T(x) is of the form T(x)=a+b*x^c.

In one embodiment, the transfer function is determined based upon data fitting. In particular, the data used to perform such fitting can include can include flow vs temperature, flow vs excitation voltage, flow velocity vs temperature, flow velocity vs excitation voltage, and others. One or more sensor specific parameter(s) useable by the transfer function are stored in the guide wire-based probe memory storage. In one embodiment, the transfer function is determined based upon models, constraints, and other equations alone or in combination with data.

The time to collect data from a blood vessel and display pressure and flow information based on the collected data ranges from greater than about 0 zero seconds to about 1 second. In one embodiment, the data includes time varying electrical signals correlated with changes in resistance. In one embodiment, the data includes time varying electrical signals correlated with changes in current.

In one embodiment, the potential differences applied to one or more resistors disposed in the sensing portion of the guide wire-based probe ranges from about greater than about 0.1 to about 15 volts. In one embodiment, the temperature changes measured in a blood vessel using a pressure (P), flow (Q), or temperature (T) sensing portion of the guide wire-based probe ranges from about greater than about 0 degrees C. to about 5 degrees C. In one embodiment, the excitation voltage needed to create adequate over-temperature (i.e. sensitivity to flow changes) is greater than about 4 volts. This excitation voltage range applies to CVEX and CTA implementations in one embodiment.

In part, the disclosure relates to a method of collecting blood vessel related data. The method includes storing, in one or more memory devices, guide wire-based probe data; measuring a first electrical signal associated with a first resistor and a second resistor disposed in the blood vessel; measuring a second electrical signal associated with the second resistor disposed in the blood vessel; determining a transfer function using the guide wire-based probe data, the transfer function having a flow parameter as an output; determining a blood pressure value for the blood vessel using one or more of the first and second electrical signals; determining a blood temperature value for the blood vessel using one or more of the first and second electrical signals; determining a blood flow value for the blood vessel using one or more of the first and second electrical signals and the transfer function; and displaying a pressure versus flow curve for the blood vessel. In one embodiment, the transfer function relates the flow parameter and an excitation voltage. In one embodiment, the transfer function relates the flow value and a temperature of one or more of the first resistor and the second resistor. In one embodiment, the method further includes identifying one or more of an occurrence of a maximum flow, a minimum flow, and a relative extremum of flow and correlating such an occurrence with an intravascular or cardiac event.

In part, the disclosure relates to an intravascular pressure and flow monitoring system. The system includes one or more memory devices; and a computing device in communication with the memory device, wherein the memory device comprises instructions executable by the computing device to cause the computing device to: determine one or more intravascular pressure values in response to a first electrical signal from a measurement circuit formed from a guide wire-based probe and an interface device; determine one or more intravascular flow values using a transfer function in response to a second electrical signal from the measurement circuit formed from the guide wire-based probe and the interface device; and display a pressure versus flow curve generated based on the one or more intravascular pressure values and the intravascular flow values, wherein the pressure versus flow curve changes over time.

In one embodiment, the pressure versus flow curve is displayed on a substantial real time basis. In one embodiment, the transfer function T(x), wherein x is flow, is of the form T(x)=a+b*ln(x), wherein a and b are constants. In one embodiment, the transfer function T(x), wherein x is flow, is of the form $T(x)=a+b*x^c$, wherein a, b and c are constants. In one embodiment, the system further includes instructions which display one or more cardiovascular related values obtained during one or more points in time.

In one embodiment, the one or more cardiovascular related values are selected from the group consisting of a flow velocity, a pressure value, a maximum flow, a minimum flow, a relative extremum of flow one or more fractional flow reserve (FFR) values, coronary flow reserve (CFR) values, coronary flow velocity reserve (CFVR) values, instantaneous flow reserve (IFR) values, and one or more index of myocardial resistance (IMR) values.

In one embodiment, the system further includes instructions which display one or more trajectories or signatures generated in response to intravascular probe data with respect to one or more positions in an artery. In one embodiment, the system further includes instructions which display a user interface that includes a flow velocity, a pressure value, a maximum flow, a minimum flow, a relative extremum of flow one or more fractional flow reserve (FFR) values, coronary flow reserve (CFR) values, coronary flow velocity reserve (CFVR) values, instantaneous flow reserve (IFR) values, or one or more index of myocardial resistance (IMR) values generated using pressure and flow data from a intravascular probe.

In one embodiment, the system further includes instructions to determine one or more temperature values using a linear or other function in response to a second electrical signal from the measurement circuit formed from the guide wire-based probe and the interface device.

In part, the disclosure relates to an intravascular pressure and flow monitoring adapter kit. The kit includes a power supply unit comprising a first intravascular pressure measurement system output connection; and a second intravascular pressure measurement system output connection, wherein a power output range of the power supply unit ranges from greater than about 0.2 volts and less than about 12 volts, the power supply unit sized to electrically connect to an intravascular pressure measurement system. The kit may include one or more electrical components in electrical communication with the power supply. In one embodiment of the kit, the one or more electrical components are selected from the group consisting of a filter, an amplifier, a current source, a voltage source, and a control system connection.

In one embodiment of the kit, the power output range is from about 0.3 volts to about 30 volts. In one embodiment of the kit, the kit further includes a non-transitory storage medium comprising instructions to cause a computing device of the intravascular pressure monitoring system to: store a transfer function in memory that outputs intravascular flow values in response to a excitation voltage or a temperature; and generate an intravascular flow value in response to (i) an excitation voltage or (ii) a difference between a fixed voltage and a voltage across a temperature dependent resistor from the power supply unit and the transfer function.

In part, the disclosure relates to a method of calibrating a flow monitoring device. The method includes selecting an excitation voltage for a pressure sensor such that a temperature of the sensor and a temperature of blood in which the pressure sensor is disposed substantially match; determining an absolute temperature of blood in a blood vessel of interest; and measuring a flow value in the blood vessel using the pressure sensor. In one embodiment, the method includes determining an absolute temperature of blood in a blood vessel of interest comprises obtaining measurements during changes to a switch configuration in an interface system.

In part, the disclosure relates to an integrated cardiology system. The system includes a display system; a pressure and flow measurement system in electrical communication with the display system; a processor disposed in one of the display or pressure and flow measurement system; one or more panels generated using the processor and depicted on the display, wherein the one or more panels comprises flow values and pressure values obtained using an intravascular probe that comprises a pressure and flow sensor. In one embodiment, the one or more panels include a pressure versus flow curve that include one or more trajectories generated using intravascular pressure and flow data and further comprising an input to receive data signals from the intravascular probe, the intravascular probe comprising a temperature sensor to measure temperature changes correlated with flow values.

In one embodiment, a trajectory can include without limitation a graphical representation of transitions between states relevant to the cardiac cycle and vary based upon stenosis, pressure changes in the arteries, and flow changes due to constrictions and other artery or heart states. In one embodiment, one or more panels include a signature, a trajectory, a slope, a maximum point, a minimum point, a ratio of measured values, a ratio of a measured value and a derived value, a ratio of a first derived value and a second derived value, an area, one or more (FFR) values, coronary flow reserve (CFR) values, coronary flow velocity reserve (CFVR) values, instantaneous flow reserve (IFR) values, and one or more myocardial resistance (IMR) values.

In part, the disclosure relates to intravascular pressure and flow monitoring system. The system includes an intravascular pressure and flow interface system comprising a wired interface or a wireless interface to receive data from an intravascular probe; a display system in electrical communication with the intravascular pressure and flow interface system; one or more memory storage devices comprising instructions to output a user interface on the display, the user interface comprising one or more panels having fields for one or more flow measurements; and a processor in electrical communication with the intravascular pressure and flow interface system, the display system, and one or more memory storage devices, the processor responsive to the instructions such that the user interface is output on the display system.

In one embodiment, the system includes a calibration system configured to convert one of a measured temperature signal or an excitation voltage into a flow velocity using a transfer function. In one embodiment, the transfer function is of the form a+b*ln x and/or a+b*x°. In one embodiment, the display system simultaneously outputs pressure and flow velocity measurements. In one embodiment, the display system simultaneously outputs pressure and absolute temperature measurements. In one embodiment, the display system outputs one or more parameters or indexes corresponding to one or more signals obtained at the measurement position of a probe sensor.

In one embodiment, the one or more parameters or indexes are selected from the group consisting of a signature, a trajectory, a slope, a maximum point, a minimum point, a ratio of measured values, a ratio of a measured value and a derived value, a ratio of a first derived value and a second derived value, an area, (FFR) values, coronary flow reserve (CFR) values, coronary flow velocity reserve (CFVR) values, instantaneous flow reserve (IFR) values, and one or more myocardial resistance (IMR) values. In one embodiment, the wired interface comprises an excitation voltage source, a first resistor, a second resistor, a first switch and a second switch. In one embodiment, the wireless interface comprises a plurality of current sources, a plurality of switches, a first resistor and a second resistor, wherein each current source is in series with one of the switches.

Coronary Flow Reserve Related Features and Embodiments

In part, the disclosure relates to methods and systems suitable for determining one or more Coronary Flow Reserve (CFR) and Fractional Flow Reserve (FFR) values separately or simultaneously using a thermoconvection device such as an intravascular pressure and flow sensor and an intravascular data collection and processing system. In addition, in part, the disclosure also relates to determining CFR values using an intravascular probe having a pressure sensor and Constant Temperature Anemometry (CTA) or Constant Excitation Voltage (CVEX) anemometry.

The disclosure also relates to a method of determining coronary flow reserve data using an intravascular pressure or flow sensor. The method includes sampling an intravascular data collection probe to obtain a one or more distal pressure values (Pd) from a distal region of a vessel and one or more thermoconvection data values; receiving one or more aortic pressure values (Pa), at an intravascular data processing system, obtained from a proximal region of the vessel; determining one or more fractional flow reserve (FFR) values from the one or more distal pressure values and the one or more aortic pressure values; determining one or more coronary flow reserve (CFR) values from the one or more thermoconvection data values; and displaying one or more FFR values and one or more CFR values on a display unit.

In one embodiment, each CFR value is determined using a transfer function. In one embodiment, the transfer function is of the form T=a+c*ln Q, wherein T is the measured temperature of the temperature variable resistor of the thermoconvection device, Q is the flow, and a and c are constants. In one embodiment, determining one or more coronary flow reserve (CFR) values comprises determining a measured temperature at hyperemic flow $T_{hyp}$ and a measured temperature at baseline flow $T_{bas}$. In one embodiment, each CFR value is determined using a relationship between $T_{hyp}$ of and $T_{bas}$ of the form $$b^{\frac{T_{hyp}-T_{bas}}{c}},$$

the form being an algebraic simplification of the inverse of the function of, wherein b is a generalized base and c is a constant. In one embodiment, the FFR values and the CFR value are displayed as numerical values and as time varying plots relative to a graphical user interface comprising one or more controls. In one embodiment, wherein one of the one or more controls comprises an enable CFR control that can be adjusted by a user to selected between an FFR display mode and a combined FFR and CFR mode. In one embodiment, the method further includes tuning a temperature signal to find maximum, minimum, or other level. In one embodiment, the step of tuning is performed by adjusting a control until an auditory or visual cue indicative of a tuned state occurs.

In part, the disclosure relates to a data collection method and/or diagnostic methods using collected data such as measured pressure, temperature, or flow values. The method includes setting a zero value for a distal pressure signal measured by an intravascular thermoconvection device; positioning intravascular thermoconvection device to delivery catheter opening; setting zero value of temperature signal measured by intravascular thermoconvection device prior to advancing into vascular system; advancing intravascular thermoconvection device to a position distal to the catheter opening; equalizing intravascular thermoconvection device pressure signal (Pd) to the aortic pressure (Pa) signal; tuning or optimizing, temperature signal of intravascular thermoconvection device, when in measurement location of interest; sampling intravascular thermoconvection device to obtain baseline thermoconvection signal value; sampling intravascular thermoconvection device to obtain Pd values and thermoconvection device values for running FFR and CFR calculations. In one embodiment, the method further includes verifying pressure equalization and flow signal return to baseline level. In one embodiment, the method further includes displaying one or more FFR values and one or more CFR values relative to a graphic user interface comprising one or more axis and one or more control inputs. In one embodiment, the control inputs and user interface are implemented using a touch screen.

In part, the disclosure relates to an intravascular data monitoring system. The system includes an intravascular data collection system comprising an interface to receive data from an intravascular probe; a display system in electrical communication with the intravascular data collection system; one or more memory storage devices comprising instructions to output a user interface on the display system, the user interface comprising one or more regions for displaying one or more CFR values or a plot thereof, the user interface comprising one or more regions for displaying one or more FFR values or a plot thereof; a processor in electrical communication with the intravascular data collection system, the display system, and one or more memory storage devices, the processor programmed to sample a plurality of proximal pressure values (Pa); sample a plurality of distal pressure values (Pd); sample a plurality of thermoconvection data values and determine the one or more CFR values and the one or more FFR values using the sampled Pa values, Pd values, and thermoconvection data values.

In part, the disclosure relates to a method of calibrating an intravascular data collecting system. The method includes setting a baseline value for a distal pressure signal measured by an intravascular thermoconvection device; positioning intravascular thermoconvection device to delivery catheter opening; setting baseline value of temperature signal measured by intravascular thermoconvection device prior to advancing into vascular system; advancing intravascular thermoconvection device to a position distal to the catheter opening; equalizing intravascular thermoconvection device pressure signal (Pd) to the aortic pressure (Pa) signal; calibrating temperature signal of intravascular thermoconvection device, when in measurement location of interest; and sampling intravascular thermoconvection device to obtain Pd values and thermoconvection device values.

Stenosis Assessment and Flow Threshold/Peak Guided Measurement Embodiments

In part, the disclosure relates to intravascular pressure monitoring systems and data collection devices suitable for analysing pressure drops in a non-hyperemic state or hyperemic state and identifying one or more flow thresholds and collecting or otherwise generating diagnostic data relative to the data collect at such a selected point in time. In one embodiment, pressure ratios such as distal to proximal ratios or pressure differences are collected at different one or more flow thresholds over time. The pressure and flow values measured at each flow threshold can be used to calculate the arithmetic mean of the pressure ratio/difference over a number of heartbeats.

In part, the disclosure relates to a method of assessing a blood vessel. The method includes measuring a plurality of intravascular blood flow values and a plurality of blood pressure values during one or more heartbeats using one or more sensors; determining a flow threshold for one or more heartbeats using one or more of the plurality of intravascular blood flow values, determining, a proximal pressure value (Pa) and a distal pressure value (Pd) during the flow threshold; calculating a first diagnostic parameter based upon the Pa and Pd values at the flow threshold for one or more heartbeats; displaying, on a user display, the first diagnostic parameter for one or more heart beats or a second diagnostic parameter determined using the first diagnostic parameter. In one embodiment, the first diagnostic parameter is a pressure difference Pa−Pd or a pressure ratio Pd/Pa. In one embodiment, the plurality of blood pressure values comprise one or more of proximal pressure values relative measured relative to a stenosis and one or more aortic pressure values.

In one embodiment, the first diagnostic parameter and the second diagnostic parameter are selected from the group consisting of Pa, Pd, Pd/Pa, Pa−Pd, a flow velocity, a pressure value, a maximum flow, a minimum flow, a relative extremum of flow, a fractional flow reserve (FFR) value, coronary flow reserve (CFR) values, coronary flow velocity reserve (CFVR) values, instantaneous flow reserve (IFR) values, and one or more index of myocardial resistance (IMR) values. In one embodiment, the flow threshold is selected from the group consisting of a maximum flow during a cardiac cycle, a relative extremum flow value during a cardiac cycle, a fraction of the maximum flow during a cardiac cycle, a hyperemic max flow value, and a non-hyperemic flow value.

In one embodiment, measuring a plurality of intravascular blood flow values and a plurality of blood pressure values further includes measuring a first electrical signal associated with a first resistor and a second resistor disposed in the blood vessel; measuring a second electrical signal associated with the second resistor disposed in the blood vessel; determining one or more of the blood pressure values of the plurality of intravascular blood flow pressure values using one or more of the first and second electrical signals; determining one or more blood temperature values for the blood vessel using one or more of the first and second electrical signals; determining the plurality of intravascular blood flow values for the blood vessel using one or more of the first and second electrical signals.

In one embodiment, one or more of the blood pressure values is an aortic pressure value or proximal pressure value. In one embodiment, the first diagnostic parameter is a plot of a value over time. In one embodiment, calculating a first diagnostic parameter comprises calculating an average of pressure ratios or pressure differences for a plurality of cardiac cycles per a determined flow threshold for each cardiac cycle. In one embodiment, the first diagnostic parameter is a mean of pressure ratios for a plurality of cardiac cycles or a mean of the pressure differences for a plurality of cardiac cycles.

In part, the disclosure relates to a method of assessing a blood vessel. The method includes receiving intravascular blood flow data and blood pressure data obtained during one or more cardiac cycles, intravascular blood flow data comprising a peak blood flow value; determining a flow threshold comprising the peak blood flow value; determining, at the peak blood flow for each of the one or more heartbeats, a first intravascular blood pressure (Pa) and a second intravascular blood pressure (Pd); calculating one or more of a pressure difference between Pa and Pd for each of the one or more cardiac cycles or one or more of a pressure ratio Pd/Pa for each of the one or more cardiac cycles; and displaying, on a user display, diagnostic information about the blood vessel, wherein the diagnostic information comprises one or more of the pressure ratio, the pressure difference, or a plot thereof. In one embodiment, the calculating a pressure difference includes calculating a mean of the pressure difference for a plurality of heartbeats.

In one embodiment, the method further includes receiving electrical signals correlated with temperature changes of an intravascular thermoconvection device in thermal communication with the blood vessel, the temperature changes correlated with changes in a flow during one or more cardiac cycles, the intravascular blood flow data comprising the electrical signals; and determining the peak blood flow value from the electrical signals correlated with temperature changes.

In one embodiment, the method further includes receiving electrical signals correlated with temperature changes of an intravascular thermoconvection device in thermal communication with the blood vessel, the temperature changes correlated with changes in a flow during one or more cardiac cycles, the intravascular blood flow data includes the electrical signals; and determining the peak blood flow value from the electrical signals correlated with temperature changes.

Additional Embodiments and Implementations

In part, the disclosure relates to an intravascular pressure and flow monitoring system that includes one or more memory devices; and a computing device in communication with the memory device, wherein the memory device comprises instructions executable by the computing device to cause the computing device to: determine one or more intravascular pressure values in response to a first electrical signal from a measurement circuit formed from a guide wire-based probe and an interface device; determine one or more intravascular flow values using a transfer function in response to a second electrical signal from the measurement circuit formed from the guide wire-based probe and the interface device; and display a pressure versus flow curve generated based on the one or more intravascular pressure values and the intravascular flow values, wherein the pressure versus flow curve changes over time. In one embodiment, the pressure versus flow curve is displayed on a substantial real time basis. In one embodiment, the transfer function T(x), wherein x is flow, is of the form $T(x)=a+b*\ln(x)$, wherein a and b are constants. In one embodiment, the transfer function T(x), wherein x is flow, is of the form $T(x)=a+b*x^c$, wherein a, b and c are constants.

In one embodiment, the system further includes instructions which display one or more cardiovascular related values obtained during one or more points in time. In one embodiment, the one or more cardiovascular related values are selected from the group consisting of a flow velocity, a pressure value, a maximum flow, a minimum flow, a relative extremum of flow one or more fractional flow reserve (FFR) values, coronary flow reserve (CFR) values, coronary flow velocity reserve (CFVR) values, instantaneous flow reserve (IFR) values, and one or more index of myocardial resistance (IMR) values.

In one embodiment, the system further includes instructions which display one or more trajectories or signatures generated in response to intravascular probe data with respect to one or more positions in an artery. In one embodiment, the system further includes instructions which display a user interface that includes a flow velocity, a pressure value, a maximum flow, a minimum flow, a relative extremum of flow one or more fractional flow reserve (FFR) values, coronary flow reserve (CFR) values, coronary flow velocity reserve (CFVR) values, instantaneous flow reserve (IFR) values, or one or more index of myocardial resistance (IMR) values generated using pressure and flow data from a intravascular probe.

In one embodiment, the system further includes instructions to determine one or more temperature values using a linear or other function in response to a second electrical signal from the measurement circuit formed from the guide wire-based probe and the interface device. In one embodiment, the system further includes instructions to calibrate the guide-wire based probe by the following calibration method steps selecting an excitation voltage for a pressure sensor such that a temperature of the sensor and a temperature of blood in which the pressure sensor is disposed substantially match; determining an absolute temperature of blood in a blood vessel of interest; and measuring a flow value in the blood vessel using the pressure sensor. In one embodiment, determining an absolute temperature of blood in a blood vessel of interest comprises obtaining measurements during changes to a switch configuration in an interface system.

In one embodiment, the intravascular pressure and flow monitoring system further includes a display system; a pressure and flow measurement system in electrical communication with the display system and comprising the computing device; the computing device disposed in one of the display or pressure and flow measurement system; and one or more panels generated using the computing device and depicted on the display, wherein the one or more panels comprises flow values and pressure values obtained using an intravascular probe that comprises a pressure and flow sensor.

In one embodiment, one or more panels includes a pressure versus flow curve comprising one or more trajectories generated using intravascular pressure and flow data and further comprising an input to receive data signals from the intravascular probe, the intravascular probe comprising a temperature sensor to measure temperature changes correlated with flow values. In one embodiment, one or more panels include a signature, a trajectory, a slope, a maximum point, a minimum point, a ratio of measured values, a ratio of a measured value and a derived value, a ratio of a first derived value and a second derived value, an area, one or more (FFR) values, coronary flow reserve (CFR) values, coronary flow velocity reserve (CFVR) values, instantaneous flow reserve (IFR) values, and one or more myocardial resistance (IMR) values.

In one embodiment, the intravascular pressure and flow monitoring system further comprising instructions to process coronary flow reserve data using an intravascular pressure or flow sensor comprising: sampling an intravascular data collection probe to obtain a one or more distal pressure values (Pd) from a distal region of a vessel and one or more thermoconvection data values; receiving one or more aortic pressure values (Pa), at an intravascular data processing system, obtained from a proximal region of the vessel; determining one or more fractional flow reserve (FFR) values from the one or more distal pressure values and the one or more aortic pressure values; determining one or more coronary flow reserve (CFR) values from the one or more thermoconvection data values; and displaying one or more FFR values and one or more CFR values on a display unit, wherein each CFR value is determined using a transfer function. In one embodiment, the transfer function is of the form T=a+c*ln Q, wherein T is the measured temperature of the temperature variable resistor of the thermoconvection device, Q is the flow, and a and c are constants. In one embodiment, each CFR value is determined using a relationship between $T_{hyp}$ of and $T_{bas}$ of the form $$b^{\frac{T_{hyp}-T_{bas}}{c}},$$

the form being an algebraic simplification of the inverse of the function of claim 3, wherein b is a generalized base and c is a constant.

In part, the disclosure relates to a method of intravascular pressure and flow monitoring. The method includes measuring a plurality of intravascular blood flow values and a plurality of blood pressure values during one or more heartbeats using one or more sensors; determining a flow threshold for one or more heartbeats using one or more of the plurality of intravascular blood flow values, determining, a proximal pressure value (Pa) and a distal pressure value (Pd) during the flow threshold; calculating a first diagnostic parameter based upon the Pa and Pd values at the flow threshold for one or more heartbeats; and displaying, on a user display, the first diagnostic parameter for one or more heart beats or a second diagnostic parameter determined using the first diagnostic parameter. In one embodiment, the first diagnostic parameter can be a pressure difference Pa–Pd or a pressure ratio Pd/Pa. In one embodiment, the plurality of blood pressure values comprise one or more of proximal pressure values relative measured relative to a stenosis and one or more aortic pressure values.

In one embodiment, the first diagnostic parameter and the second diagnostic parameter are selected from the group consisting of Pa, Pd, Pd/Pa, Pa–Pd, a flow velocity, a pressure value, a maximum flow, a minimum flow, a relative extremum of flow, a fractional flow reserve (FFR) value, coronary flow reserve (CFR) values, coronary flow velocity reserve (CFVR) values, instantaneous flow reserve (IFR) values, and one or more index of myocardial resistance (IMR) values. In one embodiment, the flow threshold is selected from the group consisting of a maximum flow during a cardiac cycle, a relative extremum flow value during a cardiac cycle, a fraction of the maximum flow during a cardiac cycle, a hyperemic max flow value, and a non-hyperemic flow value. In one embodiment, measuring a plurality of intravascular blood flow values and a plurality of blood pressure values further includes measuring a first electrical signal associated with a first resistor and a second resistor disposed in the blood vessel; measuring a second electrical signal associated with the second resistor disposed in the blood vessel; determining one or more of the blood pressure values of the plurality of intravascular blood flow pressure values using one or more of the first and second electrical signals; determining one or more blood temperature values for the blood vessel using one or more of the first and second electrical signals; and determining the plurality of intravascular blood flow values for the blood vessel using one or more of the first and second electrical signals.

In one embodiment, calculating a first diagnostic parameter comprises calculating an average of pressure ratios or pressure differences for a plurality of cardiac cycles per a determined flow threshold for each cardiac cycle. In one embodiment, the first diagnostic parameter is a mean of pressure ratios for a plurality of cardiac cycles or a mean of the pressure differences for a plurality of cardiac cycles. In one embodiment, the method includes receiving electrical signals correlated with temperature changes of an intravascular thermoconvection device in thermal communication with the blood vessel, the temperature changes correlated with changes in a flow during one or more cardiac cycles, the intravascular blood flow data comprising the electrical signals; and determining the peak blood flow value from the electrical signals correlated with temperature changes.

In one embodiment, the method includes further comprising the steps of calibrating an intravascular data collection system comprising: setting a baseline value for a distal pressure signal measured by an intravascular thermoconvection device; positioning intravascular thermoconvection device to delivery catheter opening; setting baseline value of temperature signal measured by intravascular thermoconvection device prior to advancing into vascular system; advancing intravascular thermoconvection device to a position distal to the catheter opening; equalizing intravascular thermoconvection device pressure signal (Pd) to the aortic pressure (Pa) signal; calibrating temperature signal of intravascular thermoconvection device, when in measurement location of interest; and sampling intravascular thermoconvection device to obtain Pd values and thermoconvection device values.

BRIEF DESCRIPTION OF DRAWINGS

The figures are not necessarily to scale, emphasis instead generally being placed upon illustrative principles. The figures are to be considered illustrative in all aspects and are not intended to limit the disclosure, the scope of which is defined only by the claims.

DETAILED DESCRIPTION

Figure 1A:
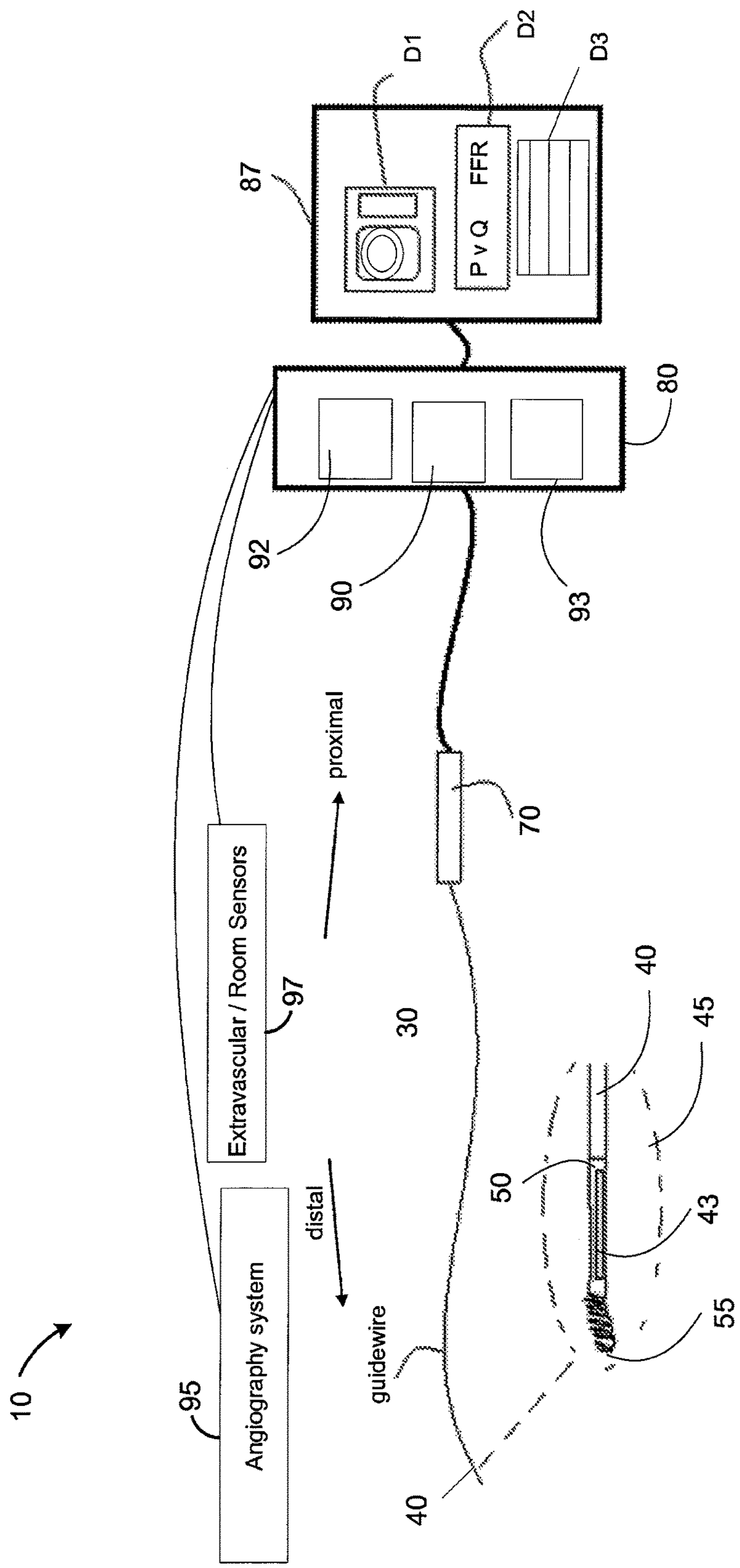
FIG. 1A is a schematic diagram of an intravascular probe suitable for measuring pressure, flow parameters and other parameters of interest in a wired configuration with one or more measurement systems.

Various data collection and analysis systems are available to obtain information with regard to the coronary system. The data obtained using a device from a blood vessel or derived data from intravascular or extravascular measurements associated therewith can be analyzed or displayed to provide correlations and extrapolations to assist researchers and clinicians. For example, various measurement systems and intravascular probes are available to determine fractional flow reserve (FFR) with respect to a blood vessel using a pressure-sensor based device. Intravascular ultrasound (IVUS) is an imaging modality that uses sound waves to image portions of a blood vessel. In turn, optical coherence tomography (OCT) is an imaging modality that uses an interferometer to obtain distance measurements relative to a blood vessel or objects disposed therein.

Intravascular data collection devices can be used to generate and receive signals that include diagnostic information relative to the blood vessel in which they are used. These devices can include without limitation imaging devices, such as optical or ultrasound probes, pressure sensor devices, flow sensors, temperature sensors, ion and other chemical sensors, and other devices suitable for collecting data with regard to a blood vessel or other components of a cardiovascular system. Angiograph system 95 and other external sensors 97 in a cath lab can also be used to image a patient and provide data to a measurement system along with data from the other devices and systems 10, 20 described herein such as for example in FIGS. 1A and 1B.

Using such devices and systems Coronary Flow Reserve (CFR) and Fractional Flow Reserve (FFR) values can be determined separately or simultaneously as described in more detail herein. Further, pressure ratios and pressure differences can be selectively measured at a specific point or a plurality of specific points in time. These points can correspond to flow thresholds such as a peak flow or another flow extremum value or a value correlated with or derived from a flow value at a point corresponding to a periodic event in the cardiac cycle. One example of such a periodic event is the point of peak or maximum flow which occurs repeatedly as the heart expands and contracts although not necessarily to the same level of flow.

In part, the disclosure relates to methods, systems, and devices by which intravascular blood flow measurements and pressure measurements can be obtained and used to generate diagnostic feedback for a subject. As used herein, references to obtaining a blood flow measurement, measuring a blood flow value or parameter, and similar references to blood flood refer to a flow velocity value or correlated value rather than an absolute flow value. Specifically, various embodiments of the disclosure described herein simultaneously perform intravascular pressure measurements while obtaining blood flow information or parameters correlated with such flow. CTA and CVEX anemometry based methods can be used in one or more embodiments to perform simultaneous flow and pressure measurements with regard to a blood vessel using a single guide wire-based probe that includes one or more optical or electrical sensors. The probe can include other sensors such as OCT, IVUS, and other data collecting sensors.

In a CTA embodiment, a constant temperature is maintained with respect to the temperature sensor. A control system is used to maintain the temperature and can detect when changes in the voltage required to maintain the temperature occur. As a result, the cooling effect of fluid flowing relative to the temperature sensor can be translated to a time varying voltage corresponding to a flow parameter. In contrast, for a CVEX embodiment, the excitation voltage of the temperature sensor is held constant and changes in resistance, impedances, and other voltages, current or time varying parameters are measured as being indicative of a flow parameter.

Intravascular blood flow measurements can be used alone or in combination with other measurements to display diagnostic information of interest on a real time or substantially real time basis such in a time period greater than about 0 seconds to about 5 seconds. Various types of data relating to a patient obtained using intravascular probes and other catheter lab measurement devices such as angiography system and room temperature, blood oximetry, and others can be integrated and displayed using an integrated cardiology display system (ICD) which can include one or more measurement systems. Additional details relating to these features are described herein.

Figure 1B:
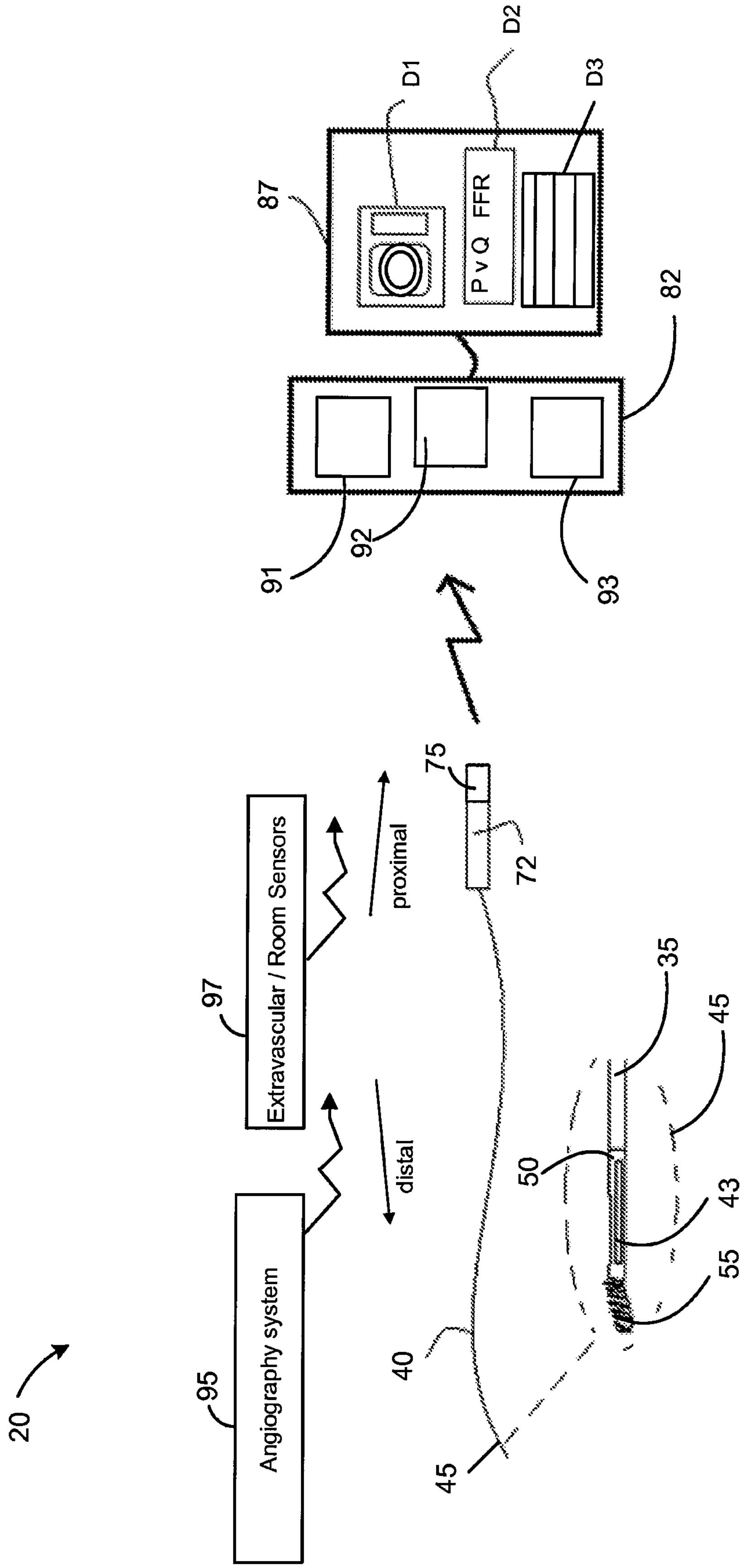
FIG. 1B is a schematic diagram of an intravascular probe suitable for measuring pressure, flow and other parameters of interest in a wireless configuration with one or more measurement systems.

FIGS. 1A and 1B show systems 10, 20 different types of guide wire-based devices suitable for use in a catheter lab or other environment by which intravascular blood flow measurements can be obtained and displayed. In FIG. 1A, an intravascular probe 20 that includes a wired connection 90 to an interface system 80 is shown. In contrast, in FIG. 1B, an intravascular probe 35 that includes a wireless connection 91 to an interface system 82 is shown. Each of the devices shown in FIGS. 1A and 1B include a guide wire 40 and one or more sensors disposed on the distal end of a guide wire which constitute components of an intravascular probe. The distal end of the guide wire is sized for insertion into a blood vessel such as a coronary artery. The one or more sensors define a sensing region suitable for sensing or measuring one or more of a pressure value P, a flow value Q, a value correlated with flow, a temperature value T, and changes relating to any of the foregoing. The P Q T sensing region 45 can correspond to the tip of the intravascular probe. The pressure sensors can be electrical, mechanical, or optical, as suitable for a given implementation.

Each of FIGS. 1A and 1B also show a magnified view of the probe tip of each respective type of intravascular probe. As shown in the magnified view the guide wire 40 is adjacent to a jacket or capsule 50 or other support structure which defines a cavity above the sensor array 43. The jacket or capsule can be a metal tube in one embodiment. The sensor array can include one or more sensors. In one embodiment, the sensor array 43 includes a pressure sensitive resistor and a temperature sensitive resistor. In another embodiment, the sensor array includes an optical pressure sensor such as an optical fiber-based pressure sensor. The sensory array can include optical flow sensor, a mechanical flow sensor, and other flow sensors. Electrical connections or optical connections, depending on the type of pressure and flow sensor, extend from the sensor array through the guide wire to the proximal connector. The probe tip can include one or more coils 55 such as for navigability or angiography detection as shown in FIG. 2D.

As shown in FIGS. 1A and 1B, the proximal connectors 70, 72 differentiate the two types of probes 30, 35. The proximal connector 70 of FIG. 1A is in communication with the probe tip at the distal end and connected to the guide wire at the proximal end of the probe. The proximal connector 70 as shown in FIG. 1A connects to a probe interface/processing system 80 via a releasable wired connection 90. In contrast, the intravascular probe 35 of FIG. 1B has a guide wire that terminates at a proximal connector 72 that includes a transmitter 75.

With regard to a wireless embodiment of FIG. 1B, the transmitter sends signals from the probe to the probe interface/processing system 82 wirelessly while the embodiment of FIG. 1A uses a wired connection 90. The proximal connector and transmitter also include a power supply such as a battery in one embodiment. Each of the proximal connectors includes electrical or optical connections to the sensor array disposed in the probe tip. The proximal connector can also include interface circuitry that forms a wired or wireless bridge with a measurement system such as the probe interface/processing system.

Figure 4A:
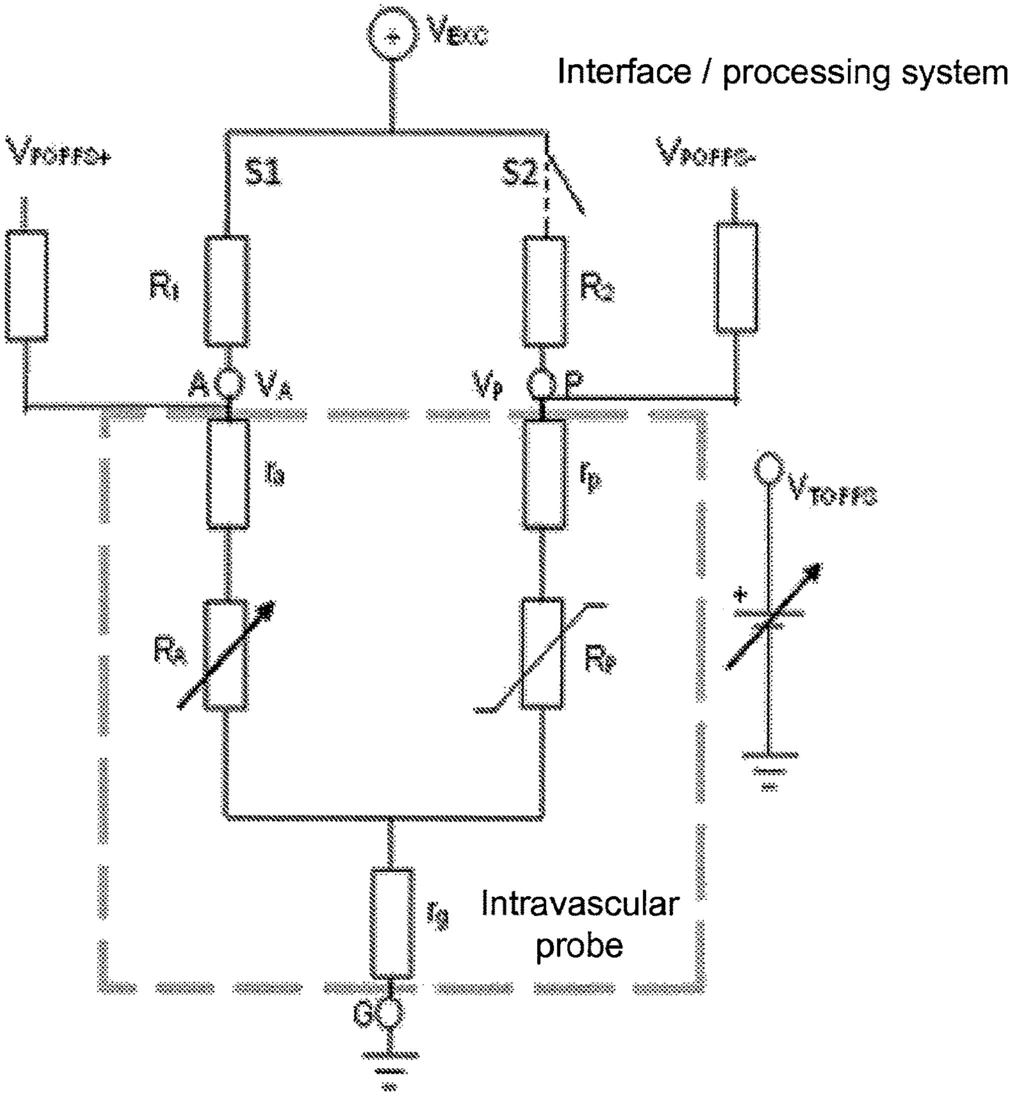
FIG. 4A is a circuit diagram including various resistors and nodes as a representation of components of an intravascular probe and an interface or processing system in a bridge configuration in accordance with an illustrative embodiment of the disclosure.

In a wired connector-based system that uses an electrical pressure sensor, the interfacing electronics, such as for example those of FIG. 4A, are located inside the display system 87 or another measurement system in one embodiment. The display system, the interface/processing system and other systems that have inputs to receive intravascular probe signals can be separate systems or combined in varying degrees as one or more systems such as an ICD. Analog-to-digital conversion, signal processing and conversion of raw signal data into calibrated data, and Graphical User Interfaces for real-time presentation of pressure, flow, and temperature data can be implemented in one or more of the systems described herein that directly or indirectly receive probe signals or data including data generated from probe signals or data received from a given intravascular probe.

The interfaces or the interface unit are connected to one or more circuits or signal processing or control elements. These circuits, elements, and other components of a given intravascular measurement system are used to convert the time varying electrical signals from the guide wire-based probe to flow data and pressure data. The time varying electrical signals can be currents, voltages, resistance changes, temperature changes, or other data correlated with flow or pressure in a vessel. The interfaces and displays are formatted and programmed to display one or more panels. Panels can include sections of display such as those used in measurement systems for pressure data, ultrasound images, angiography images, OCT images, and other intravascular images and data. One or more such panels, such D1, D2, and D3 can be controlled and programmed using a display system or other measurement system to display the flow data as a real-time curve in the time domain. Pressure data can be displayed simultaneously with flow data. FFR values based on pressure data can also be displayed. Various trajectories and loops as described herein can also be displayed with points of interest.

The display system includes various panels, displays or GUIs such as D1, D2, and D3. These panels can represent suitable intravascular measurement data such as imaging data or pressure data or other data such as angiography data, ultrasound data or OCT data. For example, D1, D2, or D3 can show pressure versus flow curves and real-time FFR data obtained using pressure measurements for other measurements. D1, D2, or D3 can also show other intravascular data of interest including imaging data, relative extrema, maximum flow, minimum flow, maximum pressure, minimum pressure, myocardial resistance, flow data, stent placement images, and other details of interest.

In one embodiment, the flow data is displayed in the same way or a compatible or synchronized format as the pressure data. For example, an additional panel such as D1 or D2 or D3 can be added to an existing user interface or data display screen for a measurement system such as an FFR system or a combination or multimodal intravascular data collection system. The extra panel or panels can display pressure and flow information simultaneously such as via pressure and flow curves or through other representations integrated with FFR results. The displays or interfaces can be part of or in electrical communication, such as by wireless communication, with an interface unit for a guide wire-based probe, OCT, FFR, IVUS, or other intravascular data collection system. In one embodiment, a transfer function or a calibration function is used to calibrate the guide wire-based probe and uses the memory stored parameters as inputs as part of a calibration system 93. The calibration system 93 can be part of a control system 92 in one embodiment.

D1, D2, and D3 can provide control user interfaces for the flow and pressure measurement system. In addition, the information or graphical user interface panels D1, D2, D3 and others can be used to display one or more of the plots or parameters depicted in FIGS. 7A to 10B. Although, D1, D2, and D3 are shown, these are by way of example and not limitation. Thus, various additional or fewer displays, panels or subpanels can be used for one or more of the types of real time and stored data and user interfaces described herein.

In a wireless probe-based system, in one embodiment, the interfacing electronics are located inside the proximal connector and transmitter. Analog-to-digital conversion of signal data obtained with regard to blood flowing in a vessel is performed within the proximal connector in one embodiment. Further, conversion of raw data into calibrated data can be performed by circuit elements or a processor in the proximal connector and transmitter or in the display system. The Graphical User Interface (GUI) for real-time presentation of pressure, flow, and temperature data is implemented in the display system in one embodiment.

In part, embodiments of the disclosure relate to various features of pressure sensing devices, measurement systems, and software relating thereto suitable for pressure monitoring and flow monitoring. The pressure monitoring and flow monitoring can be performed using a guide wire-based probe with a semiconductor device that includes components that undergo electrical changes in response to flow and pressure changes. Simultaneous pressure and flow measurements are desirable for a number of clinical measurements such as coronary flow reserve (CFR), coronary flow velocity reserve (CFVR), fractional flow reserve (FFR) and index of myocardial resistance (IMR). In one embodiment, a max flow value or other flow value of interest, such as from a region of a P-Q plot, is identified using one of the embodiments described herein such that one or more of CFR, CFVR, FFR, or IMR can be performed in response to such a value. The embodiments described herein support methods of performing these procedures and measurements using a guide wire-based probe and associated software and electrical components of a measurement system.

A guide wire-based probe can be used in conjunction with a measurement platform and software-based methods as described herein to simultaneously measure pressure and flow based on electrical signal changes. These components provide a useful diagnostic tool and various interface types for displaying data on a real time basis. In light of the ability to obtain such data from electrical signals from a guide wire-based probe, the pressure and flow data can be displayed while the probe is in the patient. In turn, the pressure and flow data can be plotted together in real-time as a pressure versus flow or P-Q plot and used to trigger events or as a diagnostic tool as described herein. A stent can be deployed along the guide wire of the probe or using other catheter deployable wires or devices to a location identified by an angiography system or other imaging system co-registered with the pressure and flow probe's position in a patient and its output data.

Figure 2A:
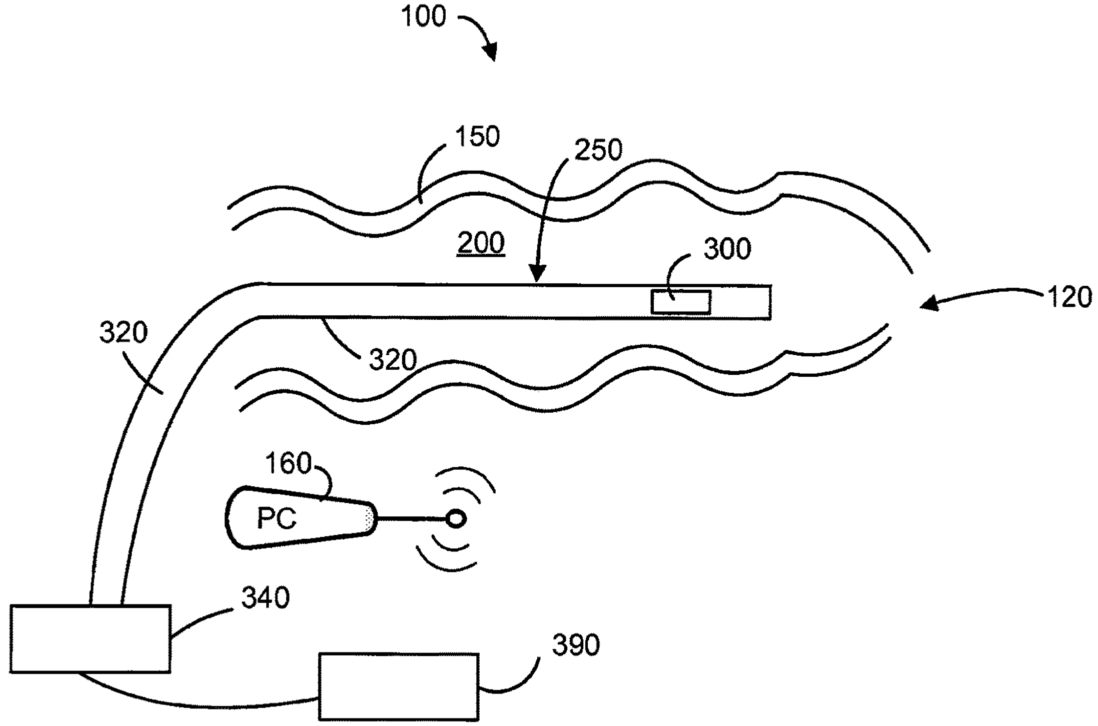
FIG. 2A is a schematic diagram of a blood vessel having a pressure and flow sensing guide wire-based probe disposed therein in accordance with an illustrative embodiment of the disclosure.

As shown in FIG. 2A, a blood vessel 100 is shown, which can be, for example, a segment of a coronary artery. Blood flows in the vessel 100 and throughout the rest of the artery and undergoes flow changes and pressure drops as the blood encounters areas of constriction in the path of flow such as a stenosis 120, as shown. The wall 150 of the blood vessel 100 surrounds a lumen 200 through which blood flows. A pressure sensor-based device 250, such as a guide wire-based probe, can be inserted in the lumen 200 of the vessel 100 to obtain data with regard to the vessel 100. The sensing region 300 of the device 250 in which flow and pressure sensing is performed is exposed to the blood, but can be surrounded by a capsule, jacket or other structural support or other structure. The capsule, jacket or other elongate supporting region or member provides structural support while allowing an opening for the sensing region.

A guide wire 320 that includes electrical leads in communication with circuit elements in region 300 can be used to introduce the device 250 into the blood vessel's lumen 200 as shown in FIG. 2A. The guide wire 320 is part of the guide wire-based probe in one embodiment. Typically, the pressure sensor-based device 250 is disposed within a catheter (not shown). Measurements can be obtained within the catheter during which flow is constrained or substantially zero to provide a reference or calibration value for flow. The guide wire may terminate in a wireless proximal connector PC in one embodiment.

In one embodiment, the electrical leads disposed in the guide wire and the guide wire-based probe terminate in a connector or a wireless device such that data can be relayed to a probe interface system 340 also referred to an interface unit. The probe interface system or unit 340 can perform measurement calculations based on signals from the probe. Alternatively, the system 340 can receive signals encoding results of calculations performed using circuitry or processing elements disposed in the probe such as for example in the probe's proximal connector. In one embodiment, the interface unit 340 is a component or subsystem of a measurement unit. In one embodiment, the interface unit 340 is in communication with a measurement system 390 that can include a display unit or an ICD. Systems 340 and 390 can include a power supply and other adapter components to provide or control the over-temperature or excitation voltages as described herein. Adapter components can be used to retro-fit existing pressure monitoring systems.

The measurement or interface unit 340 can include circuit elements selected to balance or operate with those disposed in the guide wire-based probe. The interface unit can also include software, control systems, and data analysis and display devices and processors suitable for graphing and displaying pressure, flow, and relative extremum relating to the foregoing. In one embodiment, the control systems are programmed to trigger pressure measurements, flow measurements or otherwise perform FFR, CFR, CFVR or other procedures or calculations when one of the following occurs: maximum flow, maximum pressure, relative maximum flow, relative maximum pressure, and other values or thresholds.

Figure 2B:
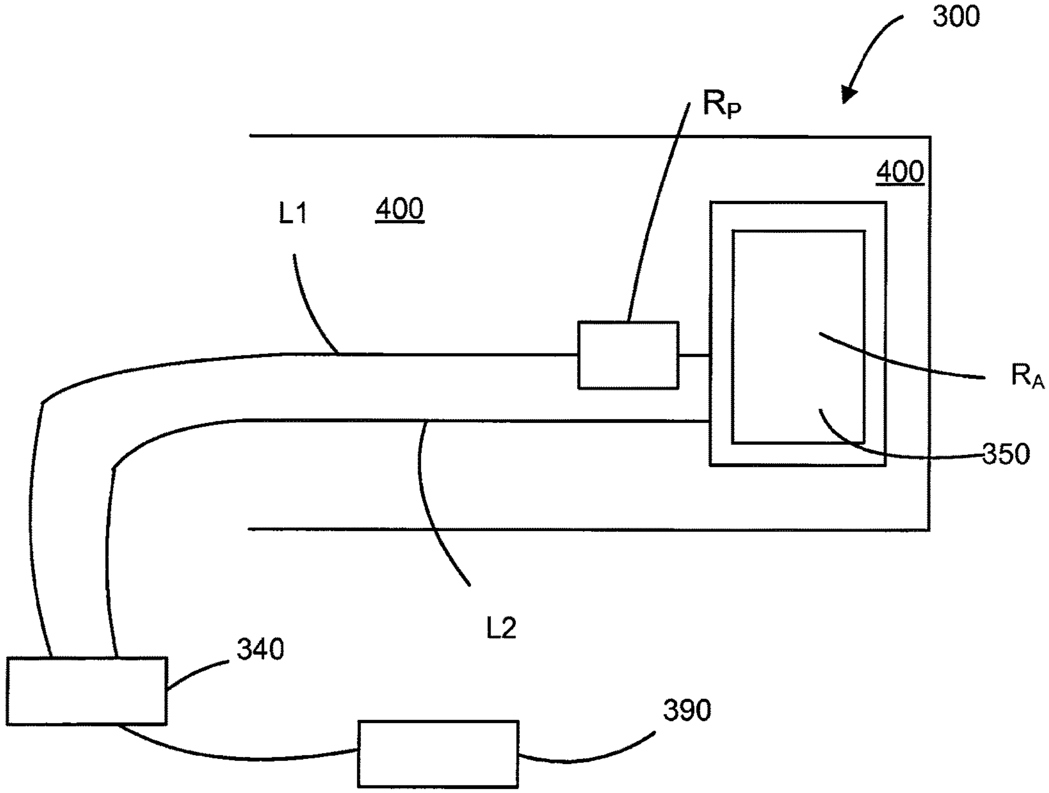
FIG. 2B is a schematic diagram of a sensing region and related components of an exemplary guide wire-based probe embodiment suitable for simultaneous pressure and flow measurements in accordance with an illustrative embodiment of the disclosure.

FIG. 2B shows additional details relating to the sensing region 300 of the guide wire-based probe of FIG. 2A. The guide wire 320 typically includes a sensing region 300, which may be partially covered or otherwise supported by a capsule which is exposed to flowing blood. The sensing region can be cooled directly or indirectly by flowing blood. The temperature of the sensing region can be raised to a temperature equal to or greater than flowing blood. Without being limited to a particular mechanism, in one embodiment, flowing blood contacts the sensing region 300 and transfers heat therefrom. In another embodiment, the flowing blood transfers heat from the capsule and other mass of the guide wire or other supporting structures disposed around and in thermal communication with the sensing region 300. Thus, the sensing region, capsule, and surround materials can be sized and made from suitable thermally conductive materials to increase heat transfer to improve detection of blood flow parameters.

In one embodiment, as shown in FIG. 2B, the sensing region 300 of the guide wire-based probe is in fluid communication with the surrounding blood. This sensing region is bounded by a capsule or other barrier being disposed around the sensing region. In one embodiment, the sensing region is directly cooled by flowing blood. In another embodiment, heat transfer through a capsule or other components of the probe supporting the sensing region is correlated with one or more blood flow parameters. Efficient heat transfer to the sensing region whether or not in direct contact with the surrounding blood increases the thermal response and accuracy of flow measurement. In one embodiment, the capsule is not present.

In one embodiment, a piezoelectric membrane 350 is disposed on a semiconductor substrate 400. The membrane 350 moves in response to pressure changes and serves as an active resistor or $R_A$. In turn, a reference resistor, which is also referred to as a passive resistor $R_P$ is also disposed or formed on the semiconductor substrate 400. The pressure sensor and reference or passive resistor can be electrically connected to one or more electrical leads or other electrical components in various configurations for different probe embodiments.

Figure 2C:
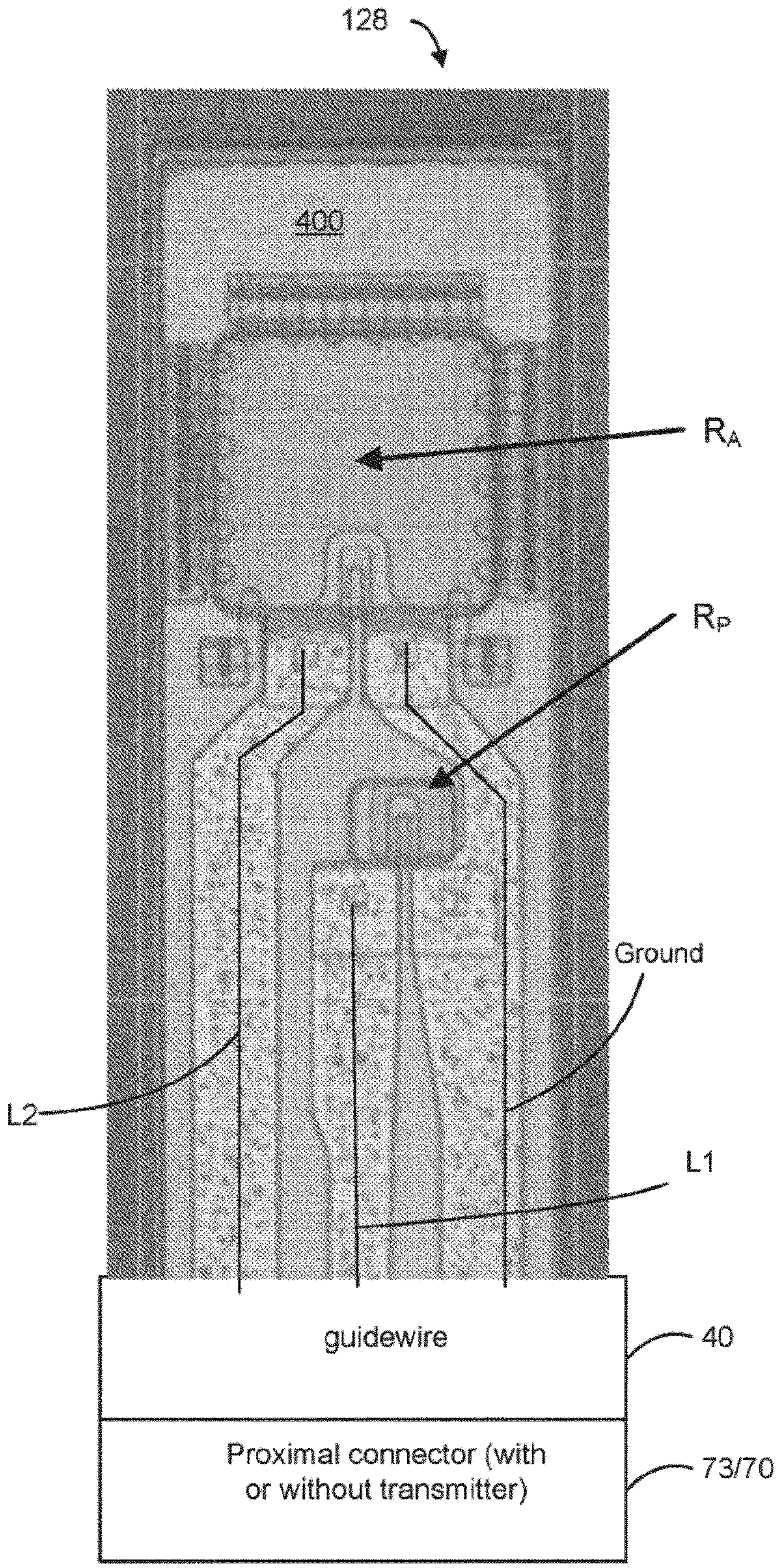
FIG. 2C is an image of a portion of a semiconductor substrate of a guide wire-based probe that includes active and passive resistors for pressure and flow sensing in accordance with an illustrative embodiment of the disclosure.
Figure 2D:
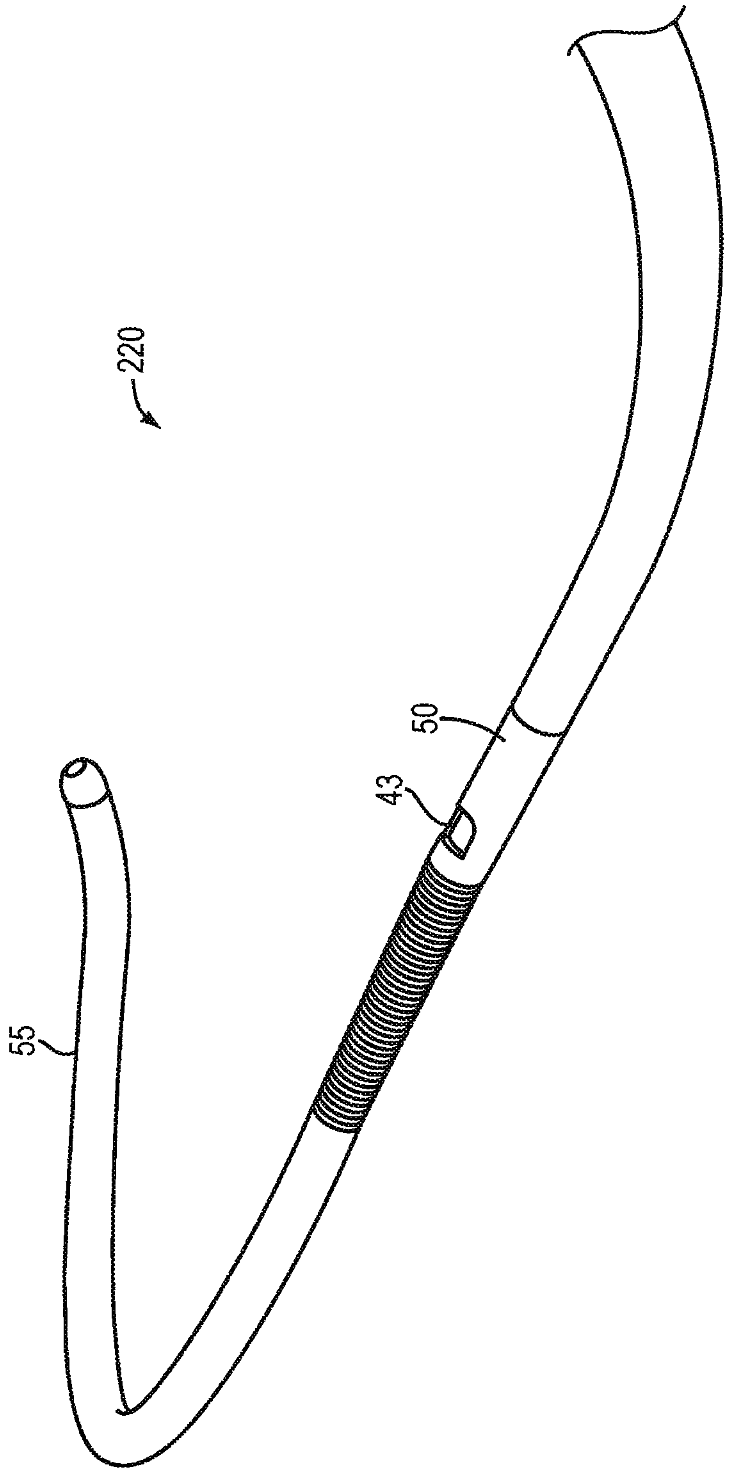
FIG. 2D is a perspective view of a guide wire-based probe showing a capsule surrounding a sensor array in accordance with an illustrative embodiment of the disclosure.

For example, electrical leads L1 and L2 are shown in electrical communication with resistors $R_P$ and $R_A$, respectively. As an alternate embodiment, FIG. 2C shows a semiconductor chip portion 128 of a guide wire-based probe device that includes a semiconductor substrate and an active and passive resistor $R_A$ and $R_P$. In one embodiment, one or more electrical leads such as leads L1 and L2 connect to a measurement system 340 through a coupler or terminal end of a guide wire integrate as part of the guide wire-based probe. A connection to ground can also be another connection from the guide wire-based probe as shown in FIG. 2B. The pressure sensor can also be implemented using an optical sensor such as an optical-fiber based etalon. The optical sensor can be integrated with other hot wire anemometry devices.

Temperature, Pressure, and Flow Data Collection

The pressure sensor-based device includes a miniature pressure sensor mounted in the tip of a guide wire as discussed herein. The pressure sensor is typically disposed on or formed from a semiconductor substrate as shown in FIGS. 2B and 2C. The pressure sensor is part of a sensor array that connects to a guide wire and support in part by a capsule as shown in FIGS. 1A and 1B. In one embodiment, the sensor array includes one sensor suitable for performing flow measurement, pressure measurement, or both of the foregoing. An exemplary representation of a sensing device such as an intravascular probe 220 having a capsule 50 and a sensory array 43 are shown in FIG. 2D. The guide wire-based probe 220 can include two or more measurement resistors, such as for example $R_A$ and $R_P$ as part of the sensor array. The pressure sensor has a membrane with a tensile strength resistor in communication with the membrane as shown by $R_A$ in FIG. 2C. When the pressure changes, it will affect the sensor membrane, and in turn change the resistance in the tensile strength resistor also referred to as an active resistor $R_A$.

$R_A$ is typically sensitive to temperature. A similar reference resistor or passive resistor $R_P$ is placed on the substrate 400 that is only sensitive to temperature. This reference resistor facilitates compensating for temperature changes that may change the pressure signal or serve as noise. As a result, in one embodiment, one guide wire-based probe resistor is sensitive to pressure and temperature ($R_A$), and the other guide wire-based probe resistor is sensitive to only temperature ($R_P$).

Figure 3:
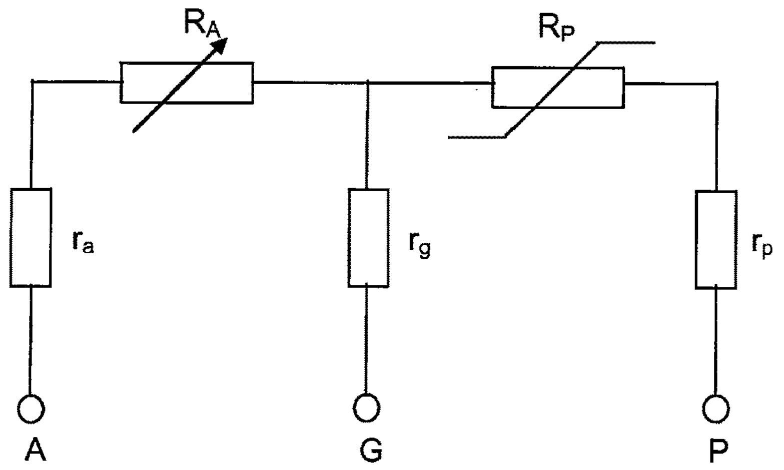
FIG. 3 is a circuit diagram including various resistors and nodes as a representation of components of a probe, connections and contact pads relating thereto in accordance with an illustrative embodiment of the disclosure.

The resistors are connected to measurement electronics, which can be disposed within or in electrical communication with an interface unit or measurement system by micro-cables. The cables selected are sized to fit in a guide-wire. Because the cables are thin, $r_a$, $r_p$, and $r_g$ have significant resistance values, typically between about 40 ohms to about 70 ohms depending on length. The micro-cables are also sensitive to temperature. An electrical equivalent model is shown in FIG. 3. The sensor array is connected to an elongate guide wire shown in schematic form that terminates at a proximal connector. As shown in FIGS. 1A and 1B, the proximal connector may include a transmitter in a wireless implementation or use a wired connection for data signal transmission as an alternative implementation.

Guide Wire-Based Probe Capsule and Flow Directing Components

FIG. 2D shows the tip 220 of a guide wire-based probe with a sensor array 43 such as that shown in FIGS. 1A, 1B, 2A, 2B, and 2C exposed through an opening in a capsule 50. The capsule or jacket, which can be a tube with an opening in its side, abuts a guide wire portion as shown and defines an opening through which one or more components of the sensor array are visible. The role of the capsule is to provide structural support for guide wire-based probe while permitting flowing blood to pass relative to sensing region and remain in contact with and cool the tip of the probe. In one embodiment, the sensitivity of the $V_{TOFFS}-V_P$ signal increases in response to a thinning or removal of the capsule. Accordingly, a combined pressure and flow measurement probe can be used with or without a capsule.

Electrical Interface Components

When using a guide wire-based probe that includes $R_A$ and $R_P$ to measure pressure and flow, it transmits data to an interface or display system such as for example a RadiAnalyzer, a RadiAnalyzer Xpress, a Quantien, or an Aeris system. In one embodiment, the guide wire-based probe device, with its own arrangement of circuit elements, is shown in FIG. 3, forms a bridge, such as for example a Wheatstone bridge when connected with the electronics of a measurement system as shown in FIG. 4A.

A shown in the circuit diagram of FIG. 3, $R_A$ and $R_P$ represents the resistors on the semiconductor substrate 40 and $r_a$, $r_g$ and $r_p$ corresponds to the micro-cables, including bond and connector of a given guide wire-based probe. The resistance of the grounding cable is $r_g$. The active and passive resistors, $R_A$ and $R_P$, can range from about 2200 ohms to about 3200 ohms, with a typical value of 2700 ohms. In one embodiment, the pressure sensitivity of $R_A$ is at least about 7.9 ppm/mmHg, and typically is about 10 ppm/mmHg. Accordingly, for a typical guide wire-based probe sensor the resistance to pressure sensitivity ratio is about 2700*10/1000000=27 mΩ/mmHg. The temperature sensitivity of $R_A$ and $R_P$ is at least 400 ppm/° C., typical is 500 ppm/° C. That means for a typical sensor the ratio of resistance to temperature is about 2700*500/1000000=about 1.35Ω/° C. A change of 0.02° C. corresponds to 1 mmHg change of the active resistor $R_A$.

FIG. 4A shows electronic components of an interface or measurement system that interface with the electronic components of the guide wire-based probe. The active resistor and the active resistor connection cable having resistance $r_a$ interface with node A of the interface or measurement system. In turn, node A is in electronic communication with resistor R1 when the guide wire-based probe is connected to the measurement device. $V_A$ is measured from node A in one embodiment. The passive resistor and the passive resistor connection having resistance $r_p$ interface with node P of the interface or measurement system. In turn, node P is in electronic communication with resistor R2 when the guide wire-based probe is connected to the measurement device. $V_P$ is measured from node P in one embodiment.

The grounding cable having resistance $r_g$ is connected to ground G. An excitation voltage $V_E$XC is applied to resistors R1 and R2. R1 and R2 are disposed in one or more systems such as a probe interface system. In one embodiment, $V_E$XC is the Wheatstone bridge excitation voltage. In one embodiment, the bridge excitation voltage ranges from about 1 volt to about 15 volts. R1 and R2 can range from about 2000 to about 3000 ohms in one embodiment. In one embodiment, the Wheatstone bridge is excited by the guide wire-based probe interface using the excitation voltage $V_E$XC and the potential difference between $V_A$ and $V_P$ is measured to derive the pressure. The temperature is measured between the $V_{TOFFS}$ and $V_P$. A 10% constraint is selected such that the $P_{OFFS}$ is able to level the bridge. The $V_{TOFFS}$ voltage corresponds to an offset voltage that is substantially equal to $V_P$ at about 37° C.

Still referring to FIG. 4A, the $V_{POFFS}$ voltage, which is applied positively and negatively as $V_{POFFS}$+ and $V_{POFFS}$− as shown in FIG. 4A, corresponds to an offset voltage used to level or balance nodes A and P on the Wheatstone bridge. $V_{POFFS}$ is an offset voltage used to balance the pressure channel in order to compensate for resistance difference between $R_A$ and Rr. The $V_{POFFS}$ is adjusted to achieve zero potential between $V_A$ and $V_P$ at zero pressure in normal barometric pressure (760 mmHg) assuming a temperature of about 37° C.

Figure 5A:
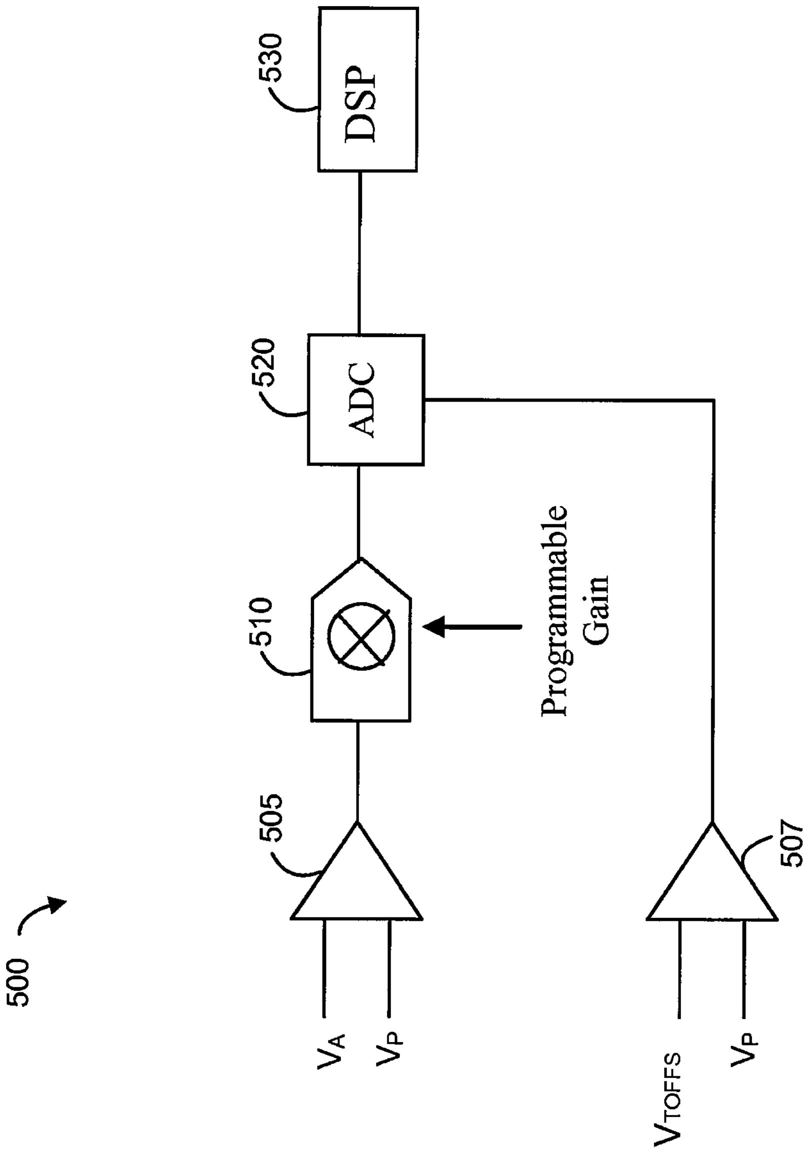
FIG. 5A is a schematic diagram of a signal sampling system for use with an intravascular probe in conjunction with a measurement bridge such as shown in FIG. 4A.

As shown in FIG. 4A, the connection of a guide wire-based probe's and a measurement system's respective electrical components allow an excitation voltage to be applied in a bridge configuration or for other current or voltage levels to be maintained as needed to support a CTA or CVEX-based approach. FIG. 5A shows how the voltages of the measurement bridge in FIG. 4A are sampled, converted and processed using a DSP. The $V_A$ and $V_P$ can be amplified using a programmable gain prior to analog to digital conversion.

A wireless interface system as shown in FIG. 1B has an electrical signal interface that forms a measurement bridge with the transmitter of a wireless intravascular probe or an equivalent or similar interface to when connecting a guide wire-based probe to a RadiAnalyzer, Xpress, a Quantien or a ComboMap® Pressure and Flow System. The guide wire-based probe interface unit or measurement system includes interface electronics that sample the analog signals of a bridge such as a Wheatstone bridge or other balanceable circuit arrange. An example of such interface electronics is shown in FIG. 4B.

Figure 4B:
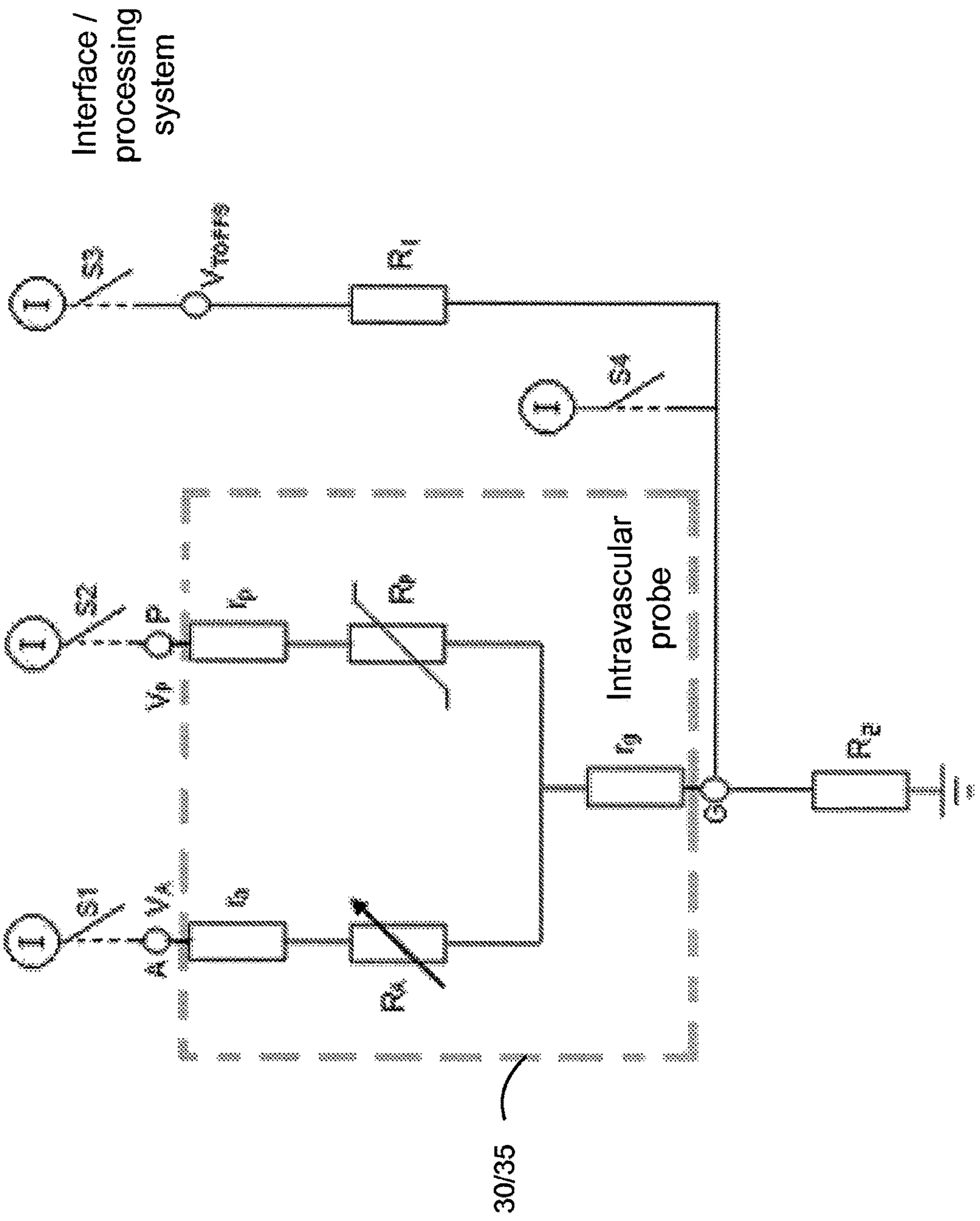
FIG. 4B is a circuit diagram including various resistors and nodes as a representation of components of an intravascular probe and an interface or processing system in a bridge configuration in accordance with an illustrative embodiment of the disclosure.

Specifically, FIG. 4B is a circuit diagram depicting interface electronics suitable for use with a wireless intravascular flow and pressure sensor. The dotted region corresponds to electrical components in the intravascular probe. For example, the embodiment of FIG. 1B is compatible with the interface circuit of FIG. 4B. The right side of the figure shows how the electronic components of the guide wire-based probe are connected to a constant current interface circuit. The constant current sources can be switched into contact with the circuit using the switches S1, S2, S3, and S4. The switches can be physical switches, a multiplexer, or implemented as software control of the current source. The resistors R1 and R2 are fixed precision resistors. In one embodiment, one or more current sources I are disposed in the proximal connector. The $V_{TOFFS}$ voltage is substantially equal to $V_P$ in one embodiment. By measuring the voltage difference $V_A - V_P$, a measure of pressure can be derived. The temperature can be derived from the $V_{TOFFS} - V_P$ voltage. The constant current circuit creates an electrical current induced heating of the guide wire-based probe chip sufficient for flow measurement using anemometry methods such CVEX, CTA and others. Switching between the current sources allows pressure and temperature (flow) values to be obtained which can then be transmitted to a measurement system wirelessly.

Modifications to Legacy System Embodiments

In one embodiment, the disclosure relates to a system adapter for adapting or otherwise retrofitting a measurement system such as a pressure measurement interface unit, such as for example a unit originally design only for pressure monitoring. Thus, after the addition of the adapter, the sensing unit can then support simultaneous pressure and flow sensing via a guide wire-based probe. The adapter includes a power supply comprising an output power range. In one embodiment, the output power range is greater than about 5 volts. In one embodiment, the output power range is greater than about 10 volts. In one embodiment, the output power range is greater than or equal to about 12 volts. In one embodiment, the adapter is a circuit board sized for installation in the measurement system.

One or more circuit elements in a guide wire-based probe interface unit can be modified or replaced to achieve a greater guide wire-based probe excitation voltage in a legacy pressure, FFR, and other intravascular data collection systems. In one embodiment, power supply components can be added or modified such that the excitation voltage applied to the sensing region is greater than about 10 volts. In other embodiment, filters can be incorporated with pass bands set to remove noise scaled to the level of flow parameter measurement signals.

Each pressure sensor-based unit has a memory storage such as an EEPROM. In one embodiment, one or more parameters obtained with regard to a guide wire-based probe, such as during its manufacture, are stored in a memory device. In one embodiment, the memory device is attached to the guide wire-based probe. The memory device can be an EEPROM, an RFID, or other suitable memory storage. The storage of one or more sensor parameters in a memory device associated with the pressure probe allows the parameters to be read as needed. Once read by a suitable scanner or interface device or component thereof, the parameters can be used to perform calibration of the guide wire-based probe prior to using it to collect pressure and flow information.

In one embodiment, the parameters stored on the probe include a zero level or baseline temperature, a zero level or baseline excitation voltage, and a sensitivity factor associated with the over-temperature. Pressure versus flow curves can also be output that show changes of pressure and flow over time and at locations in the vessel. The stored memory parameters can be used to scale or calibrate pressure versus flow curves. Pressure and flow data can also be displayed with image data such as optical coherence tomography images, ultrasound images, and angiography images.

In one embodiment, the memory is disposed at the connector end containing individual specific calibration parameters set during production. These stored parameters are used by the guide wire-based probe interface unit software to convert the sampled "raw" voltages into a correct pressure value in mmHg. Specifically, the pressure sensor is measured in a final measurement station during manufacturing process. The purpose is to measure pressure sensitivity of $R_A$, temperature sensitivity of $R_A$ and $R_P$, balance the bridge with $VP_{OFFS}$ and $V_{TOFFS}$, sensor current, and temperature range. In one embodiment, relevant parameters are then stored in a memory such an RFID chip or an EEPROM or other memory. In one embodiment, the memory is located in the guide wire-based probe connector.

Flow Measurement

When using the pressure sensor-based as a hot-film anemometer the sensor array, such as the semiconductor sensor described herein, is heated by electrical current, and the cooling effect of the flowing blood is measured by sampling the voltage across the $R_P$ resistor. A circuit showing a suitable configuration of $R_P$ in which the voltage across $R_P$ can be measured as well as other resistors and electrical connections is shown in FIG. 4A. This voltage can be used in two related anemometry methods: CTA and CVEX anemometry.

One consideration associated with pressure sensor-based hot-film anemometry is to recognize that the electrical signals generated by the relevant resistors do not distinguish between flow changes and blood temperature changes. If any unusual blood temperature changes occur, they will be interpreted by the system as flow changes. As a result, a feedback loop that monitors the environment the subject is in as well as temperature reading of the patient can be obtained using other temperature sensors. Notwithstanding the foregoing, typically the blood temperature can be considered as constant give the duration of the procedure and the time it takes for blood temperature to change.

Constant Temperature Anemometry (CTA)

As an example, the guide wire-based probe shown in FIGS. 1A, 1B, 2A and 2C and the components described herein can be used as a flow measuring device, as an anemometer in a constant temperature mode also referred to as Constant Temperature Anemometry (CTA). A temperature sensitive resistor of the guide wire-based probe sensor chip is heated, by applying a controlled excitation voltage, to a certain temperature above ambient temperature. The resistor is exposed to the surrounding fluid or otherwise in communication with other thermally conductive materials that respond to changes in blood flow induce cooling and cause a related cooling change in the sensor. In turn, the flow of the fluid will have a variable cooling effect on the resistor. Higher flow increases the cooling effect, and lower flow decreases cooling. A digital system controls the excitation voltage such that the temperature sensitive ($R_P$) is stable, at a pre-defined level. Thus, the excitation voltage becomes a measure of the flow.

Figure 5B:
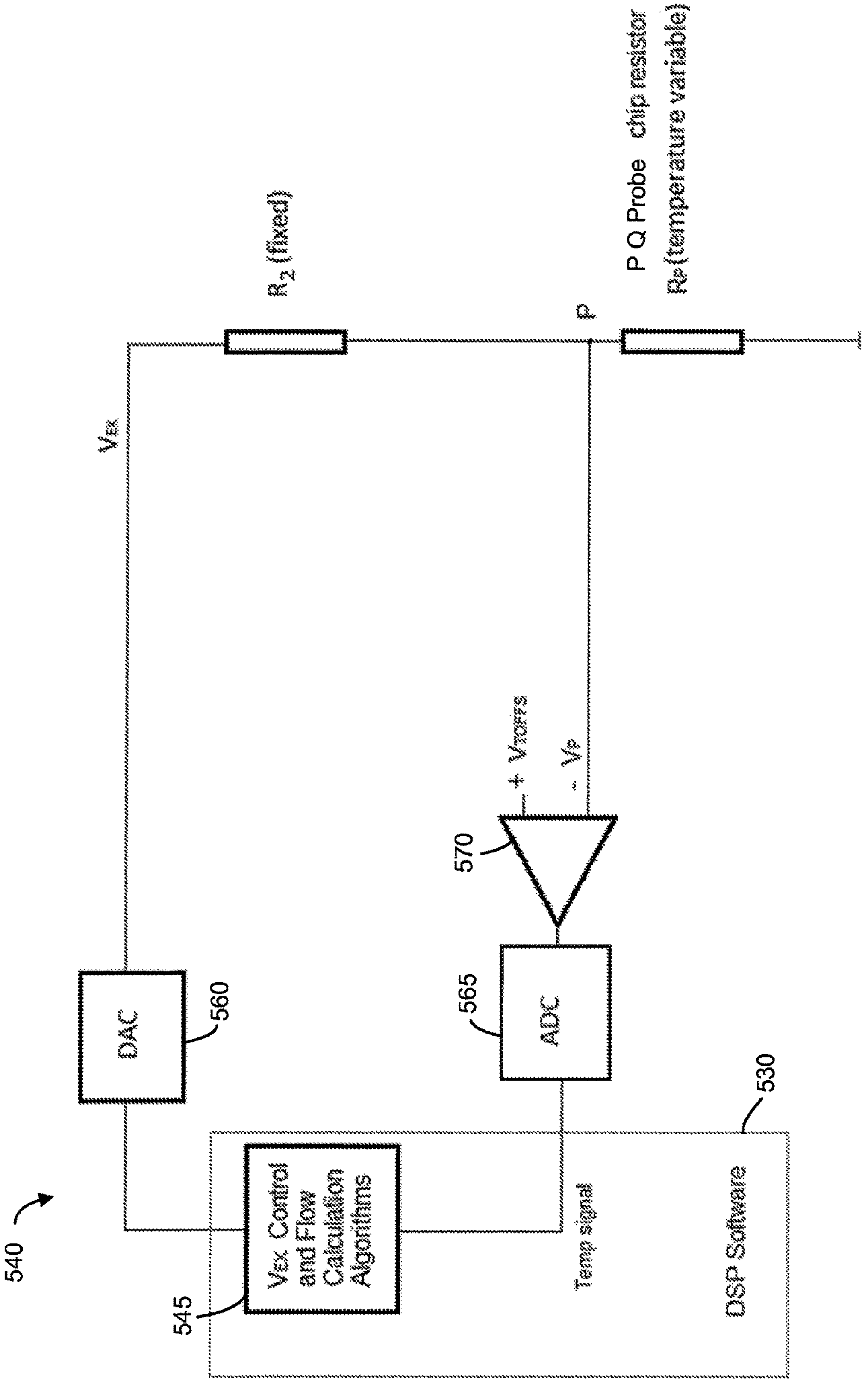
FIG. 5B is a schematic diagram of a control system for a constant temperature anemometry (CTA) embodiment, using a guide wire-based probe in accordance with an illustrative embodiment of the disclosure.

The temperature of the pressure sensor-based Rr resistor is kept at a constant level, typically ranging from about 10 to about 20 degrees C. above blood temperature. This constant temperature is controlled by the bridge excitation voltage. Higher blood flow means a higher cooling effect, leading to higher bridge excitation voltage. In contrast, a lower flow leads to lower excitation voltage. The excitation voltage thus becomes a measure of the flow. The guide wire-based probe interface unit software extracts the Rr temperature from the V $V_{TOFFS}-V_P$ voltage, and uses the temperature as the input to the excitation voltage control system. The control system is also implemented within the guide wire-based probe interface unit software, as a proportional (P) controller as shown in FIG. 5B.

CTA Control System Embodiments

FIG. 5A shows the principle of measuring flow using the measurement devices of FIGS. 1-4, using a Constant Temperature Anemometry (CTA) approach. By measuring the $V_{TOFFS}-V_P$ difference, as shown in FIG. 5A, in the signal processing system 500 shown, and dividing this signal with the applied excitation voltage (VEX), a signal which is dependent only on temperature changes of Rr and microcable resistances ra, rp, and rg of FIG. 4 is obtained. This temperature dependent signal also referred to as Temp signal in FIG. 5B is used as an input to the VEX control of the DSP software. The control system is designed to maintain a constant temperature signal by controlling the VEX. A constant temperature signal is the same as a constant temperature of Rr, which is the fundamental idea of CTA where a certain overheat is created and maintained on a surface (in this case $R_P$) subjected to a flowing fluid.

As shown in FIG. 5A, for pressure measurement, the voltage difference between $V_A$ and $V_P$ is sampled. Since $V_A$ is both temperature and pressure sensitive, ambient temperature changes that affect the $V_A-V_P$ voltage difference are compensated for using one or more signals. In one embodiment, the $V_A-V_P$ voltage difference is temperature compensated by processing it with the $V_{TOFFS}-V_P$ voltage difference using a control system or circuit or signal processing device. The $V_{TOFFS}-V_P$ is a temperature dependent signal.

As shown in FIG. 5A, there are two signal channels that are measured, pressure branch ($V_A$ and $V_P$) 505 and temperature branch ($V_{TOFFS}$ and $V_P$) 507. The pressure branch measures the difference between $V_A$ and $V_P$. The programmable gain 510 amplifies the pressure signal. The gain value can be selected on an individual basis for each guide wire-based probe sensor and stored in or generated from information stored in the memory of a given pressure probe. In one embodiment, the programmable gain value is calibrated so that one analog to digital unit (ADU) corresponds to about 0.1 mmHg. The analog to digital converter (ADC) 520 performs sampling in response to the amplified $V_A-V_P$ pressure value and outputs a pressure value in ADU units. The gain value is read by the signal processing software of DSP 530 which also loads the gain value in the gain digital to analog converter (DAC) circuit as shown in FIG. 5A.

Figure 5C:
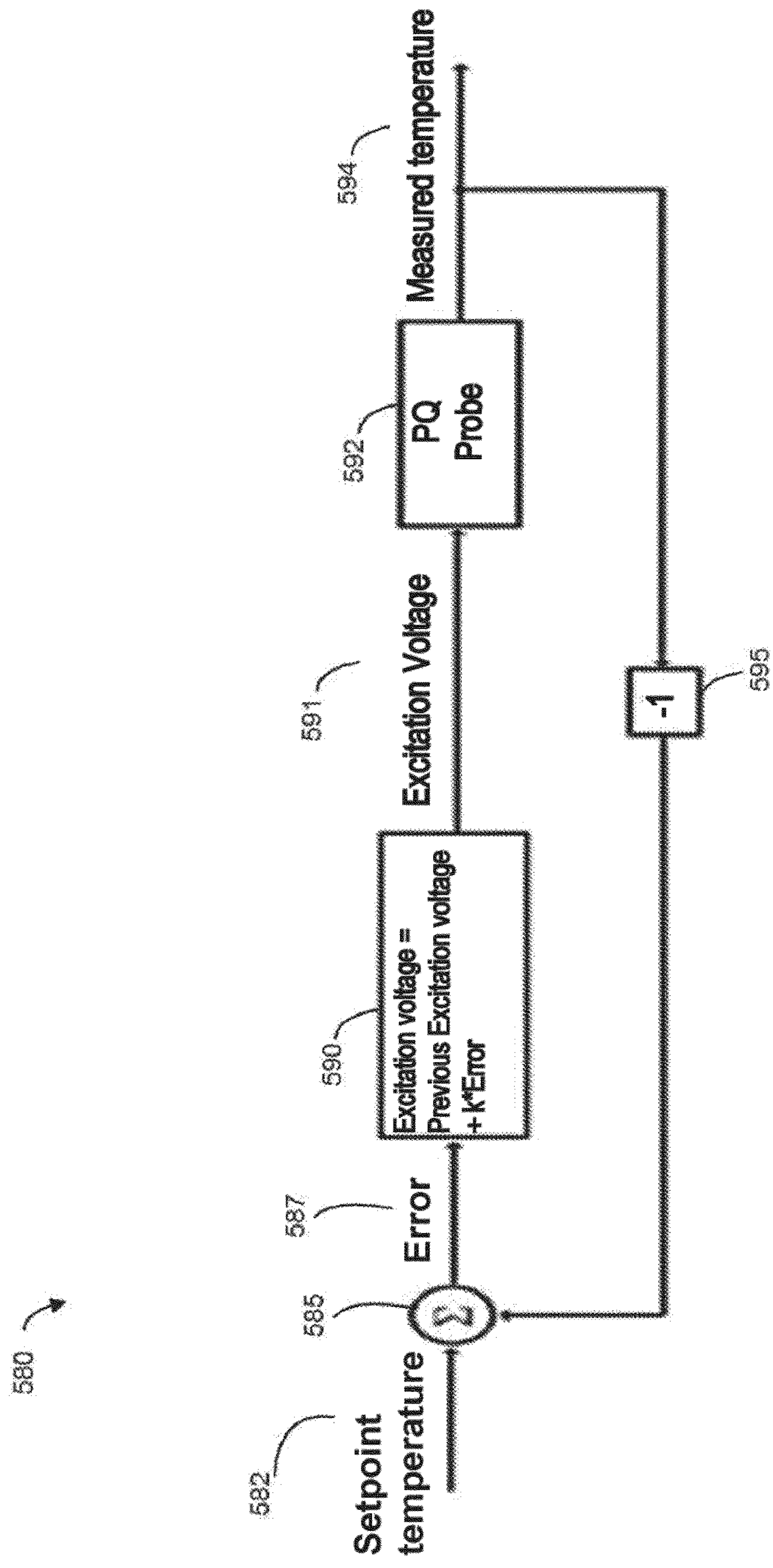
FIG. 5C is a schematic diagram of a constant temperature control system that monitors excitation voltage changes in accordance with an illustrative embodiment of the disclosure.

FIG. 5C shows a control system 580 for an intravascular measurement system based upon the CTA operating principles. The control system is programmed to keep the temperature of $R_P$ constant. The control system measures temperature changes of $R_P$ by dividing the $V_{TOFFS}-V_P$ signal with VEX, as depicted in FIG. 5B, and using this signal, denoted measured temperature in FIG. 5C as an input to the control system. The control system compares the input signal to a setpoint value corresponding to a certain $R_P$ over-temperature. The difference between the setpoint and the measured $R_P$ temperature is the error of the system which is multiplied with a factor k. The result of this multiplication is then added to the excitation voltage from the previous control iteration to produce a new excitation voltage which is used to regulate the sensing circuit in the probe tip.

Before the control system is initiated, a setpoint value based on the temperature of the fluid is established. Determining a setpoint is performed by converting the measured temperature signal at a VEX that ranges from about 0.5 to about 2 V into a centigrade value by using an ADU-to-Centigrade conversion parameter stored in memory of the guide wire-based probe. The user defined over-temperature is then added to the measured temperature of the fluid to determine the setpoint in centigrade units. The temperature representation of the setpoint is then converted into an ADU (Analog-to-Digital Unit) value to be used as the control system setpoint. The ADU-to-Centigrade conversion parameter stored in the intravascular probe memory storage or in another memory location is used to perform the conversion to a setpoint in ADU. A user can set the over-temperature using the interface of a measurement system in one embodiment.

As shown in FIG. 5C, a summer Σ 585 adds the sign inverted (−1) measured temperature 595 to the setpoint temperature 582 to produce the Error 587 of the active control system. This Error is then multiplied with a factor k as shown is processing step or stage 590 and then added to the previous excitation voltage 591. As a result of this use of a scaled error, a new excitation voltage level is generated. This new excitation voltage can then be applied to the intravascular pressure and flow monitoring probe 592. In turn, the probe 592 can be used to sample intravascular data and generate a measured temperature 594.

The measured temperature depicted in FIG. 5C is the $V_{TOFFS}-V_P$ voltage divided by the excitation voltage. This division by an excitation voltage results in a signal which is dependent only on temperature changes. The set point temperature is stored on the pressure sensor-based memory. For example, if the memory setpoint parameter is 10, the system software or the control system will keep the $R_P$ temperature at 10 degrees C. above the blood temperature. The excitation voltage ranges from about 5 volts to about 7 volts with regard to a 10 degrees C. over-temperature. A higher over-temperature (greater than 10 degrees C.) can require using a higher voltage range, i.e. greater than 7 volts, in one embodiment. These excitation voltage variations track changes in flow.

Constant Excitation Voltage

Figure 5D:
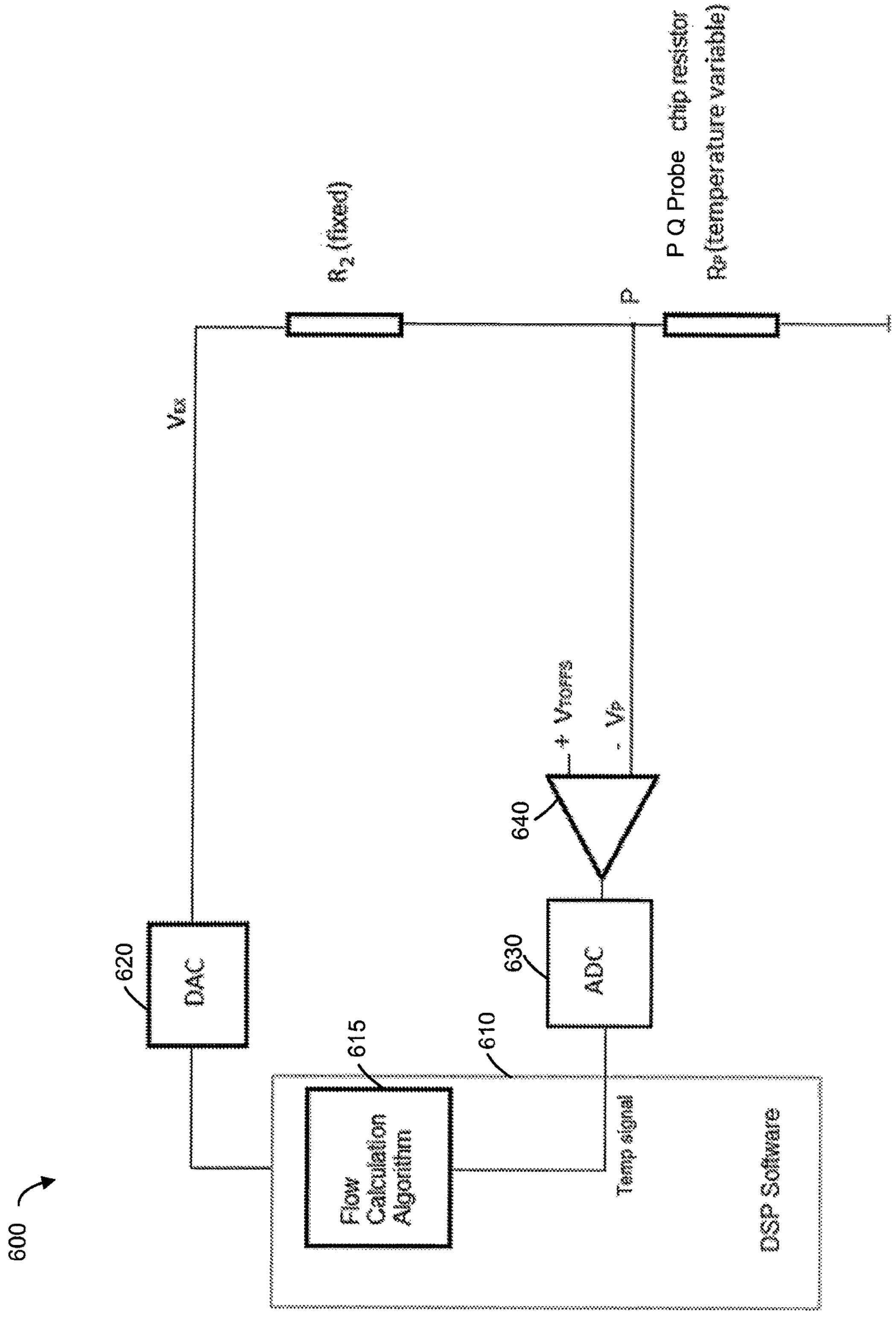
FIG. 5D is a schematic diagram of a flow calculation system implemented using a constant excitation voltage (CVEX) in accordance with an illustrative embodiment of the disclosure.

In one embodiment, a fixed excitation voltage, such about 5 volts, is used to perform flow and pressure measurements. In one embodiment, a CVEX-based approach does not include a control system algorithm because the $V_{TOFFS}-V_P$ voltage is used directly as a measure of the flow measured in a vessel. Instead, a flow value calculation algorithm is used without controlling for VEX changes as described above in terms of the control system of FIG. 5C. In contrast, the $R_P$ temperature changes with the flow. If there is a higher flow, this results in a lower $R_P$ temperature. Conversely, if there is a lower flow this results in a higher $R_P$ temperature. FIG. 5D shows a flow measurement system 600 that processes signals from a guide wire-based probe while using a constant excitation voltage or CVEX.

As shown in FIG. 5D, the DSP software embodiment of the disclosure receives the Temp signal (the sampled $V_{TOFFS}-V_P$ signal) from the analog to digital converter 630. The VEX, which is constant, is set by the DSP software and converted to an analog signal by a Digital-to-Analog converter (DAC) 620. The flow calculation algorithm 615 receives the Temp signal as an input from which it can generate flow values.

Figure 5E:
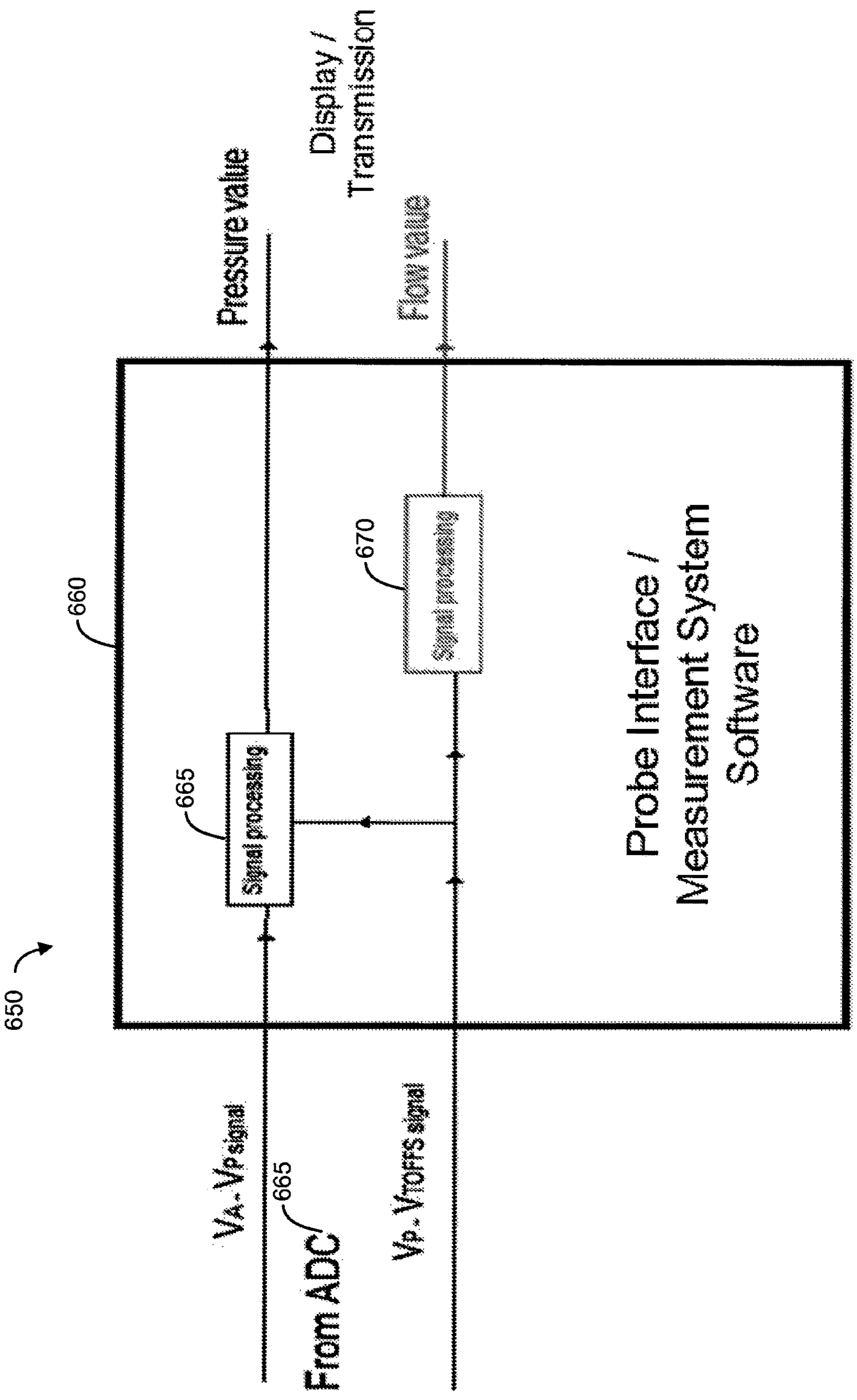
FIG. 5E is a schematic diagram of software signal processing diagram for simultaneous pressure and flow measurement using a CVEX in accordance with an illustrative embodiment of the disclosure.

FIG. 5E is a schematic diagram of software embodiment for a simultaneous pressure and flow measurement system 650 according to a CVEX method. As shown, the probe interface/measurement system software 660 receives input voltage differences from the analog to digital converter 665. The $V_A-V_P$ difference signal and the $V_{TOFFS}-V_P$ difference signal are processed to generate a pressure value which can be displayed as a value or a plot on a console or other display as described herein. In turn, the $V_{TOFFS}-V_P$ difference signal is processed to generate a flow value or a plot on a console or other display as described herein. These values can be displayed, plotted as pressure versus flow curves, and otherwise used as inputs for FFR calculations using a measurement system or calculated using a circuit or processor integrated in the probe itself.

CVEX and CTA Transfer Function Features and Embodiments

Figure 6A:
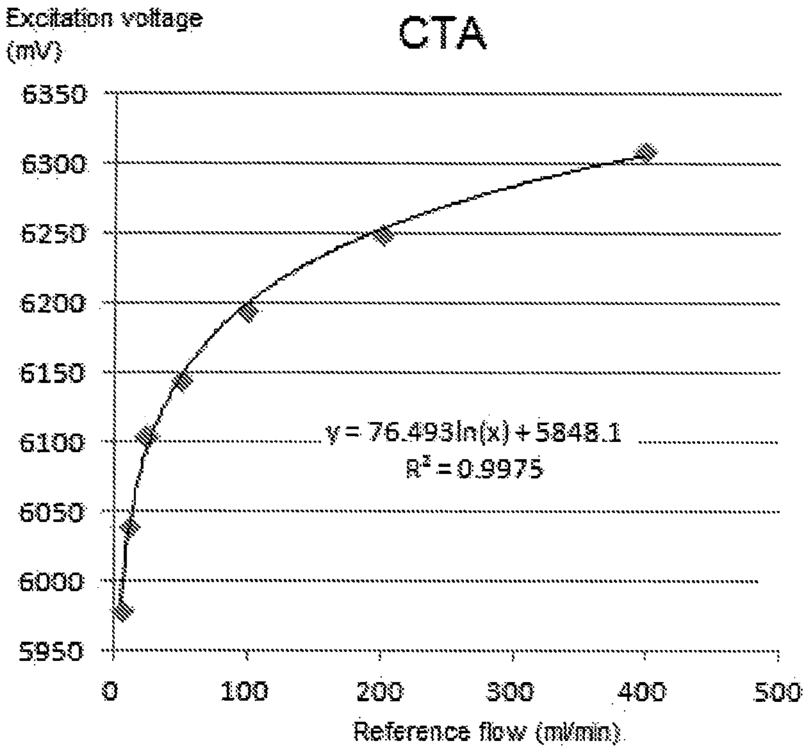
FIGS. 6A and 6B are plots and representations of transfer functions for CTA and CVEX implementations of pressure and flow monitoring using an intravascular probe, respectively, in accordance with an illustrative embodiment of the disclosure.
Figure 6B:
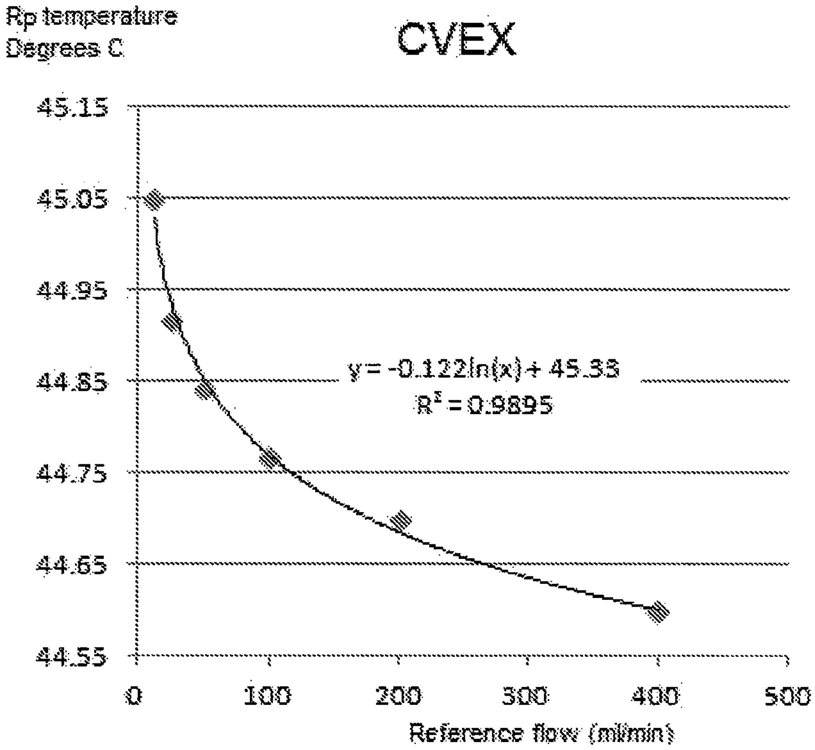

An applied excitation voltage (when using CTA) or the measured temperature (when using CVEX) can be converted to a flow value or a value correlated with flow using a transfer function. In one embodiment, the transfer function is determined by subjecting the pressure sensor-based to known reference flows and plotting the measurement signal versus the reference flow. A reference flow can be generated using a fluid flowing in a closed loop system such as water flowing in loop or curved tank. FIGS. 6A and 6B show typical relationships between measurement signals and reference flow.

FIGS. 6A and 6B shows curve fitting performed for both CTA and CVEX to obtain suitable transfer functions that relate flow, x, and temperature or excitation voltage, respectively, T(x). A pressure sensor-based unit can be calibrated by subjecting it to a number of flow levels and then, by curve fitting or other methods, determining a constant and the b constant for its individual T(x)=a+b*ln X function. T(x) outputs excitation voltage in the CTA context and T(x) outputs temperature in the CVEX context. The X value is flow or a flow parameter in either context. The transfer function constants (a and b) can be stored on the pressure sensor-based memory.

Further, the inverse of the function a+b*ln X will then be used by the guide wire-based probe interface unit software to calculate the flow value as part of a flow calculation algorithm. The flow values can be tracked overtime to display points of maximum flow. The points of maximum flow or relative extremum generated using pressure versus flow plots or other representations can be used to identify points in time or locations along a blood vessel during which images may be co-registered or measurements obtained such as a series of FFR measurements corresponding to different points in time and levels of flow that span one or more of a maximum value, a minimum value or a relative extrema.

There are several differences worth considering regarding CTA and CVEX based methods. FIGS. 6A and 6B show that CTA and CVEX share the same type of relation between flow and measured units (a+b*ln X). Further, both methods measure pulsating flow with the same accuracy (observed during lab testing). Accordingly, by taking flow measurement into account, the CVEX and CTA methods can be considered as equal. In one embodiment, measuring flow and pressure simultaneously appears to benefit from a CVEX approach because it simplifies pressure measurements. A CTA-based approach makes pressure measurements more complicated because of the varying excitation voltage. In one embodiment, the hardware and software of a CTA pressure and flow measurement system are selected to measure pressure accurately while simultaneously controlling the excitation voltage within narrow error limits.

Adapting FFR and Other Measurement Platforms for Pressure and Flow Measurements

A system measuring pressure and flow simultaneously typically can be performed based upon the CVEX principle. Implementing CVEX flow measurement in a pressure sensor-based measurement system can be performed using an adapter, such as a circuit board or circuit and power supply, and some changes in the software and control flow.

From a device or hardware standpoint, it is useful to increase maximum excitation voltage output to the pressure sensor-based measurement Wheatstone bridge. As part of the process of retrofitting an intravascular measurement system, such as a pressure only measurement system, for simultaneous pressure and flow monitoring, a guide wire-based probe interface unit board can be fitted with a 12V output power supply unit (PSU) board. In addition one or more amplifiers in a guide wire-based probe interface unit are biased with +12V and −12V instead of the usual +/−5V used for pressure sensing.

In one embodiment, the guide wire-based probe interface software samples the $V_{TOFFS}-V_P$ voltage at about sampling rate that ranges from about 400 Hz to about 600 Hz. This sampled signal is stored in memory. In one embodiment, the signal is stored at a certain position of a signal data array as a variable typically denoted TEMP. The CVEX implementation converts the voltage difference stored as the TEMP signal and converts it to a flow value, using a transfer function as described herein. A software representation of this signal processing is shown in FIG. 5E. These hardware and software features are used to provide a system which can use a pressure sensor-based to measure pressure and flow simultaneously, using a CVEX-based approach.

The flow measurement systems described herein can be implemented using certain temperature related design modifications. These include implementing one or more of a cable temperature compensation and a flow insensitive absolute temperature measurement.

Cable Temperature Compensation Method Embodiments

The switches S1 and S2 of the guide wire-based probe measurement bridge of FIG. 4A (which is typically "ON" during standard guide wire-based based probe interface unit operation) can be used to switch off either of the branches of the bridge. If S2 is switched off, resistance changes (i.e. temperature changes) of the micro-cables ra, rp, and rg can be measured by sampling the voltage ($V_{TOFFS}-V_P$). In contrast, by switching S2 on and off at a certain rate (ranging from about 400 to about 600 Hz) and sampling $V_{TOFFS}-V_P$ during both S2 states sensor array's temperature signal can be extracted:

$$\text{Sensor Temperature} = (S2\_ON\_V_{TOFFS} - V_P) - k^*(S2\_OFF\_V_{TOFFS} - V_P)$$

where ($S2\_ON\_V_{TOFFS}-V_P$) is the sampled signal during the S2 switching element's "ON" state, ($S2\_OFF\_V_{TOFFS}-V_P$) is the sampled signal during the S2 switching element's "Off" state, and k is a compensation constant associated with a particular probe interface unit. The k value can be stored in memory and accessible as needed by the sensor temperature determination method.

This cable temperature compensation method, which determines the sensor temperature, removes or reduces the impact of the cable temperature changes on the flow signal. Specifically, the method of compensating for cable effects using the "switched ON" signal with the "switched OFF" signal creates a signal which responds only to sensor temperature changes associated with the sensor array in the intravascular probe tip. This is desirable because standard handling and clinical use of a guide wire based probe induces temperature changes in the micro-cables.

These induced temperature changes can degrade an uncompensated (S2 switching element's "ON" state) signal as a result of cable resistance changes. Since flow measurement uses the $V_{TOFFS}-V_P$ signal, the cable temperature compensation method described herein yields a signal which responds only to probe tip sensor temperature changes. Further, if a stable blood temperature is present, as would typically be the case for a patient resting in a constant temperature environment, the only temperature changes to the sensor would correspond to changes in a flow parameter. In one embodiment, the flow parameter is flow velocity. In another embodiment, the flow parameter is a flow rate.

Flow Insensitive Absolute Temperature Measurement Embodiments

By using the cable temperature compensation described herein and lowering the excitation voltage to about 0.5V, a system which measures blood temperature changes (or the temperature changes of whatever medium the probe is inserted into) results. Selecting an excitation voltage that ranges from greater than about zero to about 2 volts is advantageous because it results in a sensor array temperature that is approximately the same as the surrounding blood temperature. As a result, by selecting an excitation voltage that results in sensor and fluid temperature substantially matching, the pressure and flow monitoring system is insensitive to flow changes. This results because flow measurement is based on creating a sensor array temperature in response to an excitation voltage which can be affected by the cooling of the surrounding fluid as it flows relative to the probe tip. This allows the flow of blood to be measurable as opposed to simply measuring changes in blood temperature.

The sensor temperature signal defined above is measured at 0.5V excitation voltage in one embodiment. The absolute temperature of the fluid (blood) can then be calculated using a difference relationship between a first constant and the product of a second constant and the sensor temperature:

$$\text{absolute temperature} = C - D(\text{sensor temperature})$$

wherein C and D are constants specific to the individual interface or processing systems or related integrated systems that receive data from a given intravascular probe and its sensory array. The sensor temperature referenced in the absolute formula above can be obtained using the relationship above in which sensor temperature is given by ($S2\_ON\_V_{TOFFS}-V_P$)$-k^*$($S2\_OFF\_V_{TOFFS}-V_P$). In one embodiment, the constants C and D are specific to the individual intravascular probe together with the individual interface or processing systems. These constants C and D can be encoded on a memory attached to each probe in one embodiment.

Cable compensation and absolute temperature measurements are useful features in a flow measurement system. In part, this is the case because signal influences from the micro-cable resistances are removed. Further, monitoring of the blood temperature during flow measurement is helpful since the flow measurement signal is sensitive to both flow and blood temperature changes. The user controls of the measurement system allow the user to manually switch between flow mode and absolute temperature mode.

FFR Measurements and Applications Thereof

In one embodiment, one or more pressure versus flow plots are obtained following the administration of hyperemic drugs. In one embodiment, one or more pressure versus flow plots are obtained without administering hyperemic drugs. In one embodiment, one or more FFR, pressure, flow, resistance, or other cardiovascular related measurements are obtained following the administration of hyperemic drugs. In one embodiment, one or more FFR, pressure, flow, resistance, or other cardiovascular related measurements are obtained without administering hyperemic drugs. In one embodiment, one or more FFR, pressure, flow, resistance, or other cardiovascular related measurements are obtained during periods of high or maximum flow as determined by measurements from an intravascular pressure and flow sensor.

In one embodiment, an FFR value or a related value is obtained based on the ratio of a distal pressure to a proximal pressure (Pdistal/Pproximal) in a blood vessel. In one embodiment, an FFR value or a related value is obtained based on the ratio of an obstructed max flow/an unobstructed max flow. These various approaches to obtaining flow data such as flow velocities at points in the cardiovascular system can be displayed individually or along with other cardiovascular values as ratios or through other relationships indicative of a state of a subject.

In one embodiment, the intravascular probe is moved along the length of an artery and a data set of one or more of pressure measurements, flow parameter measurements, and positional measurements are obtained over time. The elements of this data set can be synchronized with each other and registered with IVUS, angiography, OCT, or other data from additional sensors. The data set can be processed to calculate a measure distal pressure such as a distal coronary pressure and a proximal pressure such as an aortic pressure.

From these distal and proximal pressures a plurality of $FFR_i$ values can be obtained using the following relationship:

$$FFR_i = P_{distal_I}/P_{proximal_I} = \text{an obstructed max flow/an unobstructed max flow}$$

The i value can be selected as the index of the set of elements obtained with regard to the blood vessel such a flow parameters, pressure values, etc. an obstructed max flow/an unobstructed max flow FFR can also be evaluated as a maximum blood flow, a first flow, in the presence of a stenosis divided by the maximum flow if there was no stenosis, as a second flow, as noted above. The ratio of these obstructed versus unobstructed max flows yields an FFR value in terms of a flow ratio. These flows can be obtained using an intravascular probe as described herein.

In one embodiment, the FFR values that are obtained during periods of maximum or minimum flow are evaluated to determined FFR values based on events occurring during their respective measurement times and the positions along the blood vessel at which they were obtained. In one embodiment, the smallest FFR values obtained or the FFR values obtained for a maximum flow or an average maximum flow is displayed as the FFR value.

Pressure and Flow Plots and Trajectories

In one embodiment, the disclosure relates to performing pattern recognition with respect to pressure versus flow plots or datasets generated using CTA or CVEX based methods. This pattern recognition can be performed using a processor in a measurement device or another device that receives data generated from the intravascular pressure and flow probe. The pressure versus flow plots can be displayed on a real time or substantially real time basis in response to the simultaneous collection of pressure and flow data using a guide wire-based probe. The pattern recognition process can compare pressure versus flow trajectories or patterns or subsets of such curves and correlate them with conditions or patient states of interest.

In one embodiment, patient data for a healthy population is used to establish baseline signatures such as tracings or trajectories of a P-Q plot for comparison to individuals seeking diagnostic information. Individual tracings can also be obtained for individual patients and compared to subsequent tracings to show efficacy of a given treatment regimen or procedure. The quality and duration of a recovery can also be evaluated using pressure versus flow curves and other plots and FFR values obtained before during and a procedure, such as stenting, as described herein.

Figure 7A:
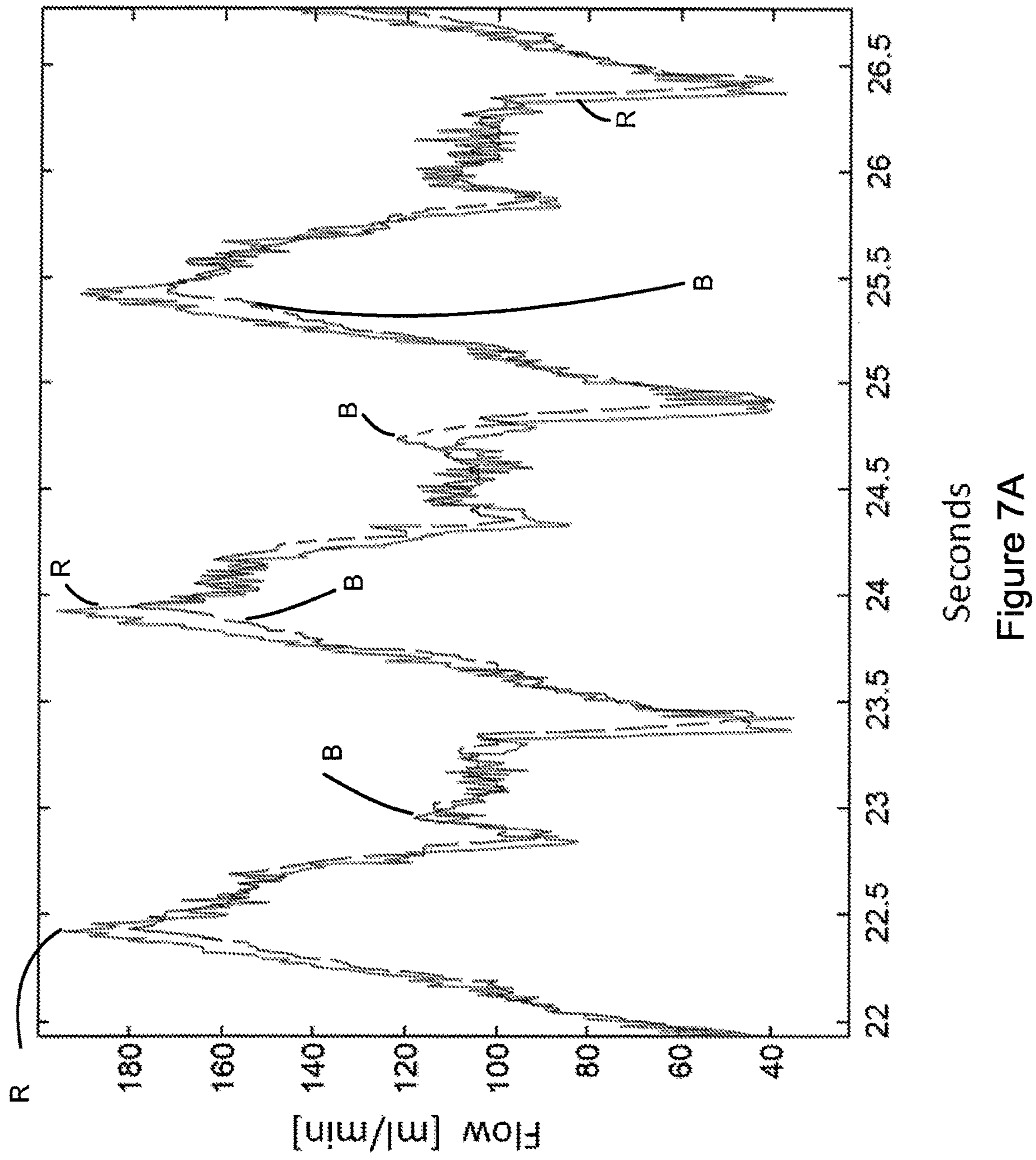
FIG. 7A shows a flow signal measured with an embodiment of the disclosure (blue color), compared to a reference flow signal (red color). The measurements were performed using a flow phantom.

The measurement or display system's graphical user interface (GUI) displays the flow data, as a real-time curve in the time domain. The pressure and flow data can be plotted together in real-time, producing a P-Q plot as shown in FIG. 7A with additional details relating to pressure and flow ranges. The indicia G for green, B for blue, and R for red are used to identify curves as recited in the legends for the plots or described herein. G is generally used to indicate a curve relating to the right side of the heart. R is generally used to indicate a curve relating to the left side of the heart. B is generally used to indicate a curve relating to blood pressure versus time.

In one embodiment, the pressure versus flow curves include relative extrema, inflexion points, maximum values and minimum values correlated with one or more dynamic events, cardiac cycle events, cardiac conditions, degree of stenosis, pre-stent flow, and post stent-flow, degree of recovery following a cardiac event, comparisons to historic data, and data obtained at different points in time. In one embodiment, the different points in time can be correlated with the introduction of one or more drugs or treatment regimen such as a stent.

In one embodiment, the pressure versus flow curves can also be used to calibrate pace maker function. This can be done by obtaining pressure versus flow curves for the patient and monitoring them as they change over time and converge to one or more trajectories or shapes. In one embodiment, adjustments to a pacemaker can be made using historic and current pressure versus flow plots to cause the trajectories to track those of a healthy heart. In this way, pacemaker operating parameters can be tuned and calibrated. The pressure versus flow curves can also be used to establish pressure readings and flow readings before and after renal denervation to provide efficacy and diagnostic information. In one embodiment, a guide wire-based probe can be positioned at various locations in arteries such as near trunks and branches while collecting pressure and flow data. Locations in which flow changes from one branch to another can be used to categorize a given branch as potentially occluded. These locations can be identified using IVUS, OCT, angiography and other imaging modalities during a procedure.

Various exemplary curves which can be obtained using a pressure and flow sensing probe are discussed in more detail below. These curves are generated using sensor data obtained in an artery at one or more locations using an intravascular probe comprising a sensor suitable for simultaneously measuring pressure, temperature, and flow. The sensor data can be used to generate one or more of the following a signature, a trajectory, a slope, a maximum point, a minimum point, a ratio of measured values, a ratio of a measured value and a derived value, a ratio of a first derived value and a second derived value, an area, a FFR value, a CFR value, a CFVR value, a IFR value, a IMR values, an index, a patient state, and other values and representations of information as described herein.

Individual data elements and curves that evolve and change over time can be used for various diagnostic purposes as described herein. In one embodiment, the trajectories or shapes or areas (or other features) of the pressure versus flow curves can be fit to historic data such as those of a patient's age, weight, activity level, and one or more patient conditions such as a heart attack, a damaged valve, and other measureable patient parameters, such that a new patient's pressure versus flow curve can be compared relative to pressure versus flow curves indicative of a particular patient state to facilitate a diagnosis.

FIG. 7A shows a plot of flow versus time using a reference flow probe, identified by R or a red color or other first indicia, and a guide-wired based pressure and flow probe, identified by B or blue color or other second indicia. The reference flow probe and the guide-wire based pressure and flow probe embodiment were both subjected to pulsatile flow in a water circulation loop. The patterns of the reference and measured flow reveal a linear relation between the applied flow and the measured signal.

Figure 7B:
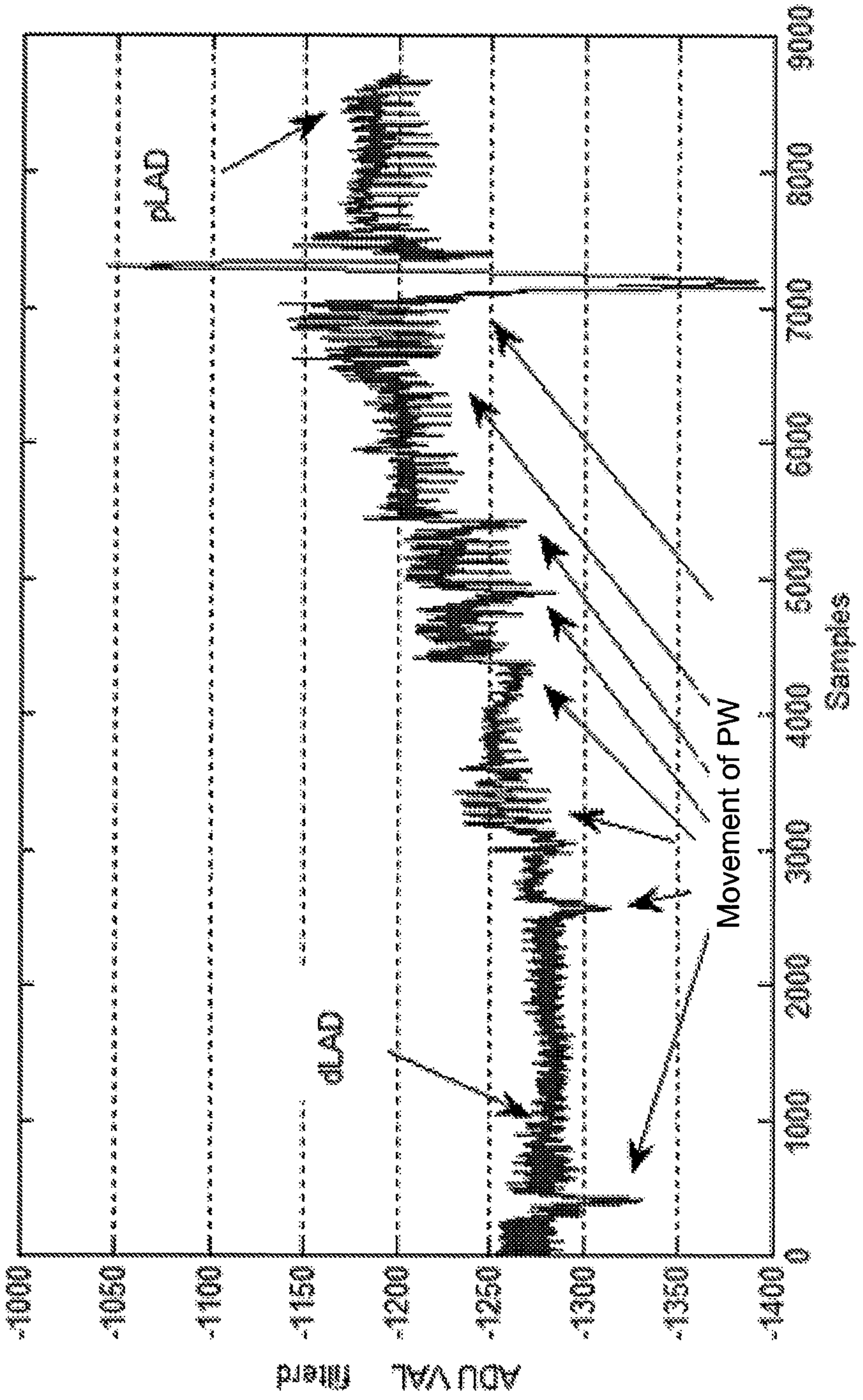
FIG. 7B shows a plot of a flow velocity pullback from distal LAD to proximal LAD. The recording was done in a beating isolated pig heart.

FIG. 7B shows a plot of measured temperature (flow) signal increases in response to when the guide wire-based probe is pulled back from a distal Left Anterior Descending Artery (dLAD) position to a proximal Left Anterior Descending Artery (pLAD) position. The pressure signal is substantially constant during the pullback of the guide wire-based probe through the artery.

Figure 8A:
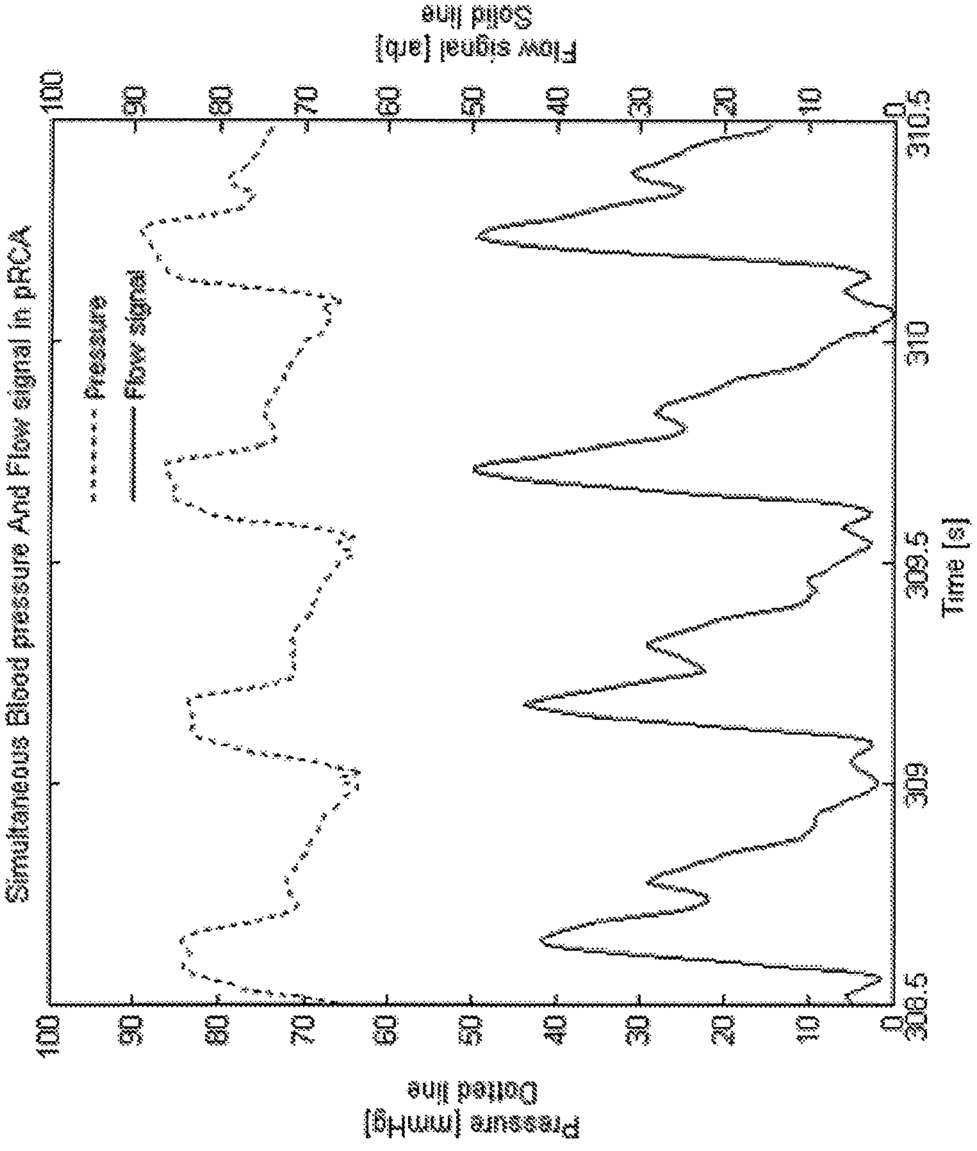
FIG. 8A shows a pressure and flow versus time plot obtained using a pressure and flow sensing probe in which the sensor is placed in the proximal RCA in a pig heart in accordance with an illustrative embodiment of the disclosure.

FIG. 8A shows a pressure and flow versus time plot obtained using a pressure and flow sensing probe with a 40 kg swine. The proximal right coronary artery (pRCA) (right side) is the location being monitored with the sensing probe. Pressure and flow are shown by the vertical axis with time along the horizontal axis. The small bump at the bottom of the curve is a small back-flow. The dotted line shows pressure values which generally rise and fall in a pattern correlated with flow in the bottom curve. The phase of the pressure and flow curves is aligned with respect to the pRCA data shown in FIG. 8A.

Figure 8B:
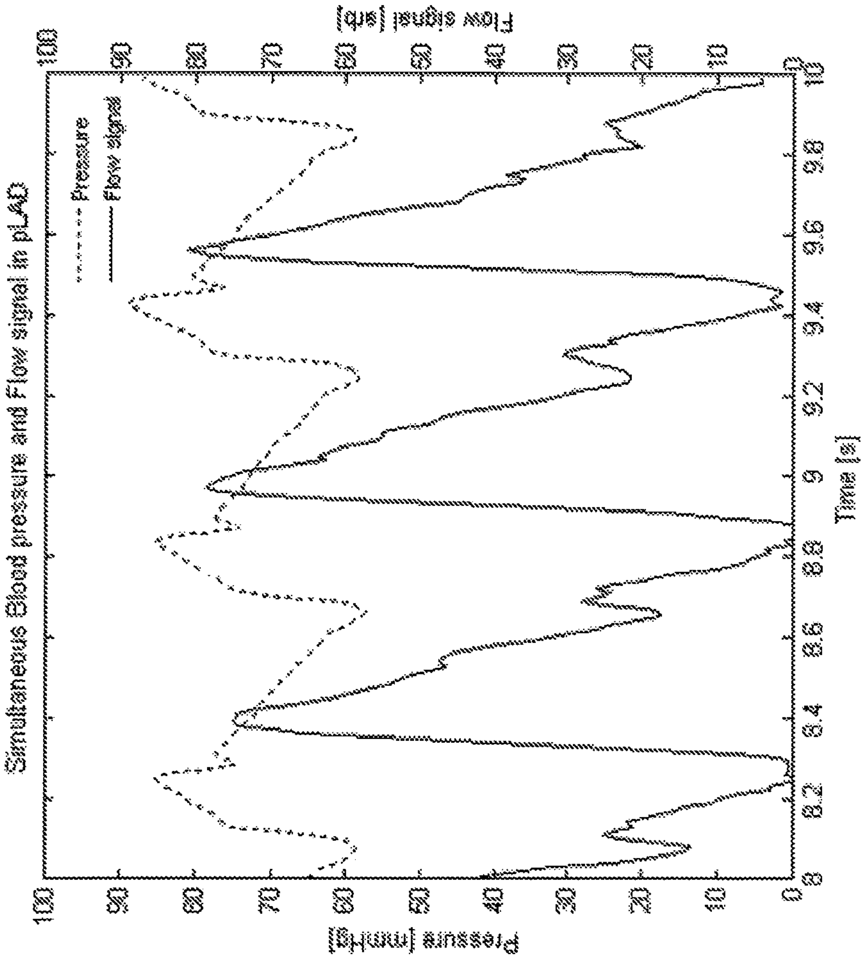
FIG. 8B shows pressure and flow versus time plots obtained using a pressure and flow sensing probe in which the sensor is placed in the proximal LAD in a pig heart in accordance with an illustrative embodiment of the disclosure.

FIG. 8B show pressure and flow versus time plots obtained using a pressure and flow sensing probe with a 40 kg swine. The pLAD is the location being monitored with the sensing probe. Pressure and flow are shown by the vertical axis with time along the horizontal axis. The small bump at the bottom of the curve is a small back-flow. In contrast with FIG. 8A, the phase of the pressure and flow curves is shifted in FIG. 8B with the pressure signal's peaks appearing as shifted to the right relative to the flow signals. As FIGS. 8A and 8B show, the flow peak is during Systole on the right side and occurs in Diastole on the left side.

Figure 8D:
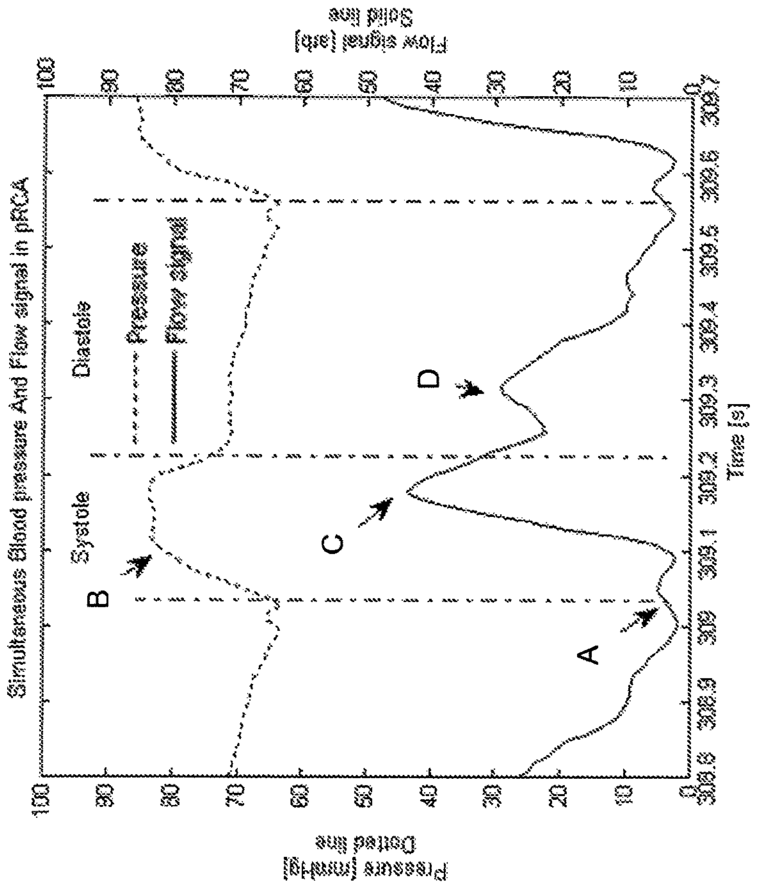
FIG. 8D shows pressure and flow versus time plots of a flow velocity profile obtained with regard to the RCA using a pressure and flow sensing probe in accordance with an illustrative embodiment of the disclosure. The marked corresponding points are shown in FIG. 8C.
Figure 8C:
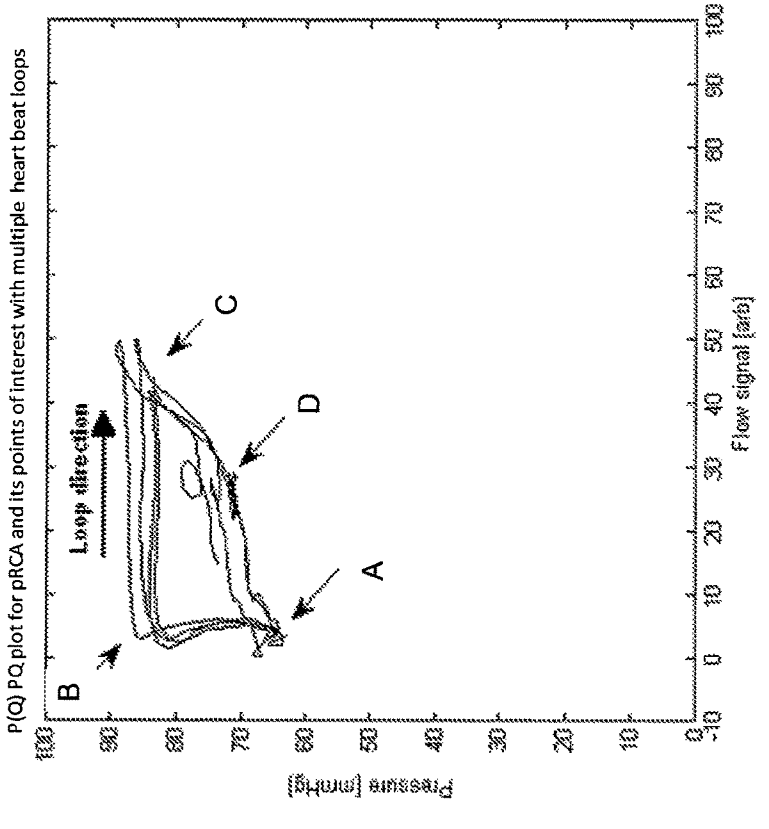
FIG. 8C shows a pressure versus flow plot obtained using a pressure and flow sensing probe having a loop or trajectory obtained with regard to the RCA in accordance with an illustrative embodiment of the disclosure. The marked corresponding points are shown in FIG. 8D.

FIG. 8C shows a pressure versus flow plot obtained using a pressure and flow sensing probe with a 40 kg swine. The proximal right coronary artery (pRCA) is the location being monitored with the sensing probe in FIG. 8C. The loop direction is in a clockwise direction. Various points of interest A, B, C and D are shown. Although, any point can be selected as a starting point, a trajectory or loop can be traced from the bottom left point A. The shape or area of the loop can be stored and compared to other loops to identify correlations in one embodiment. The shape or loop can also be monitored for contractions, expansions, shifts, or other changes before, during or after a procedure.

For example, a path from point A, which corresponds to a low flow and low pressure state, the path along the loop can be traced up to point B as pressure increases before moving along the loop to the right along a substantially horizontal path of increasing flow to point C. From point C, pressure and flow decrease as point D is reached along an angled path until the loop returns to point A. Point A corresponds to a low flow and low pressure state which characterizes the start of Systole. Point B corresponds to state of max pressure and minimum flow occurring in Systole. Point C corresponds to maximum pressure and flow, which occurs during Systole. Point D corresponds to a transitional state between A and C with a relative extremum corresponding to a second highest flow in diastole. This flow at point D is a backflow.

FIG. 8D show pressure and flow versus time plots obtained using a pressure and flow sensing probe with a 40 kg swine. The proximal RCA is the location being monitored with the sensing probe. The corresponding points A, B, C, and D from FIG. 8C are also shown in FIG. 8D. The points show rising pressure and flow as Systole commences and then decreasing pressure and flow in diastole following the contraction of the heart.

Figure 8F:
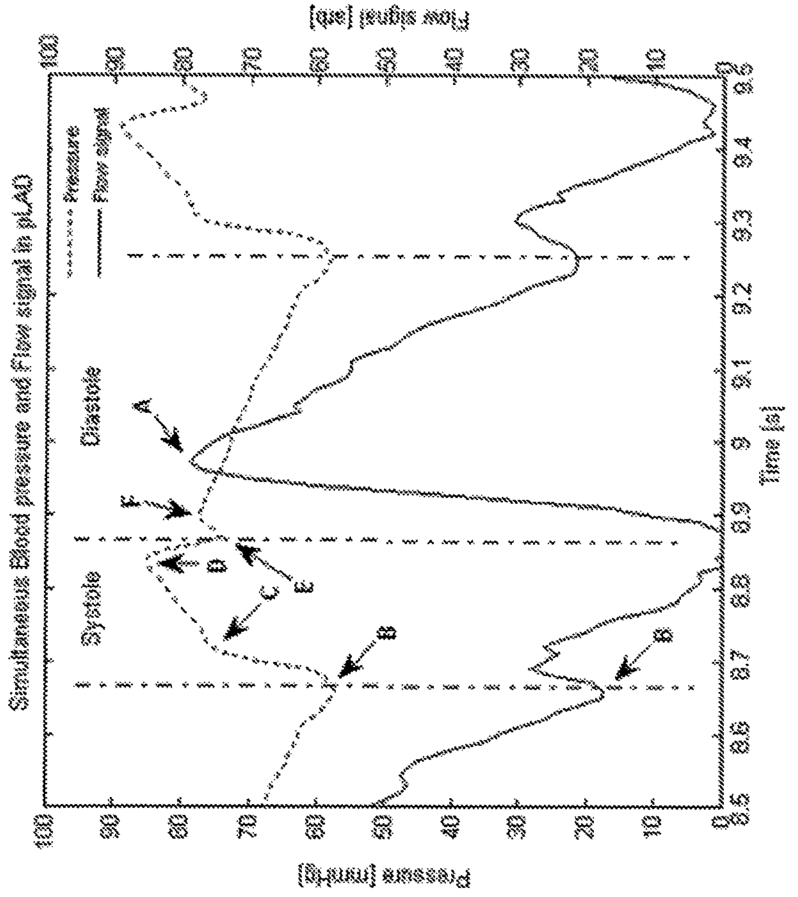
FIG. 8F shows a pressure and flow versus time plot of a flow velocity profile obtained with regard to the LCA in accordance with an illustrative embodiment of the disclosure. The marked corresponding points are shown in FIG. 8E.
Figure 8E:
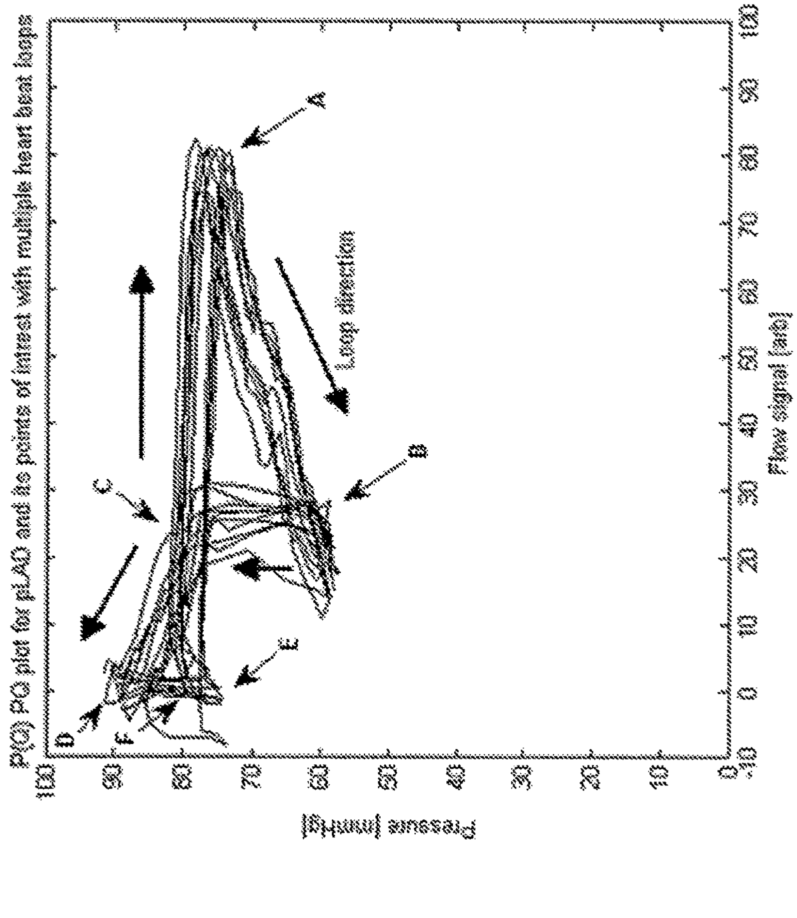
FIG. 8E shows a pressure versus flow plot having a loop or trajectory obtained with regard to the LCA using a pressure and flow sensing probe in accordance with an illustrative embodiment of the disclosure. The marked corresponding points are shown in FIG. 8F.

FIG. 8E shows a pressure versus flow plot obtained using a pressure and flow sensing probe with a 40 kg swine. FIG. 8F shows a pressure and flow versus time plot corresponding to the data of FIG. 8E. The proximal left anterior descending coronary artery (pLAD) is the location being monitored with the sensing probe. The loop direction is in a clockwise direction. Various points of interest A, B, C, D, E and F are shown. The majority of the points of interest selected, B, C, D, and E, occur in Systole with points A and F occurring in diastole. Point A corresponds to the maximum flow in diastole following contraction of the heart in Systole. Point B corresponds to the minimum pressure value, which occurs at the onset of systole. Point C corresponds to relative local increase in pressure prior to reaching the maximum pressure at point D. Point E corresponds to the closing of the aortic valve and a decrease of pressure in the left ventricle. Accordingly, as shown in FIG. 8E, when the pressure drops, the blood flow in the left coronary arteries again increases.

Figure 9A:
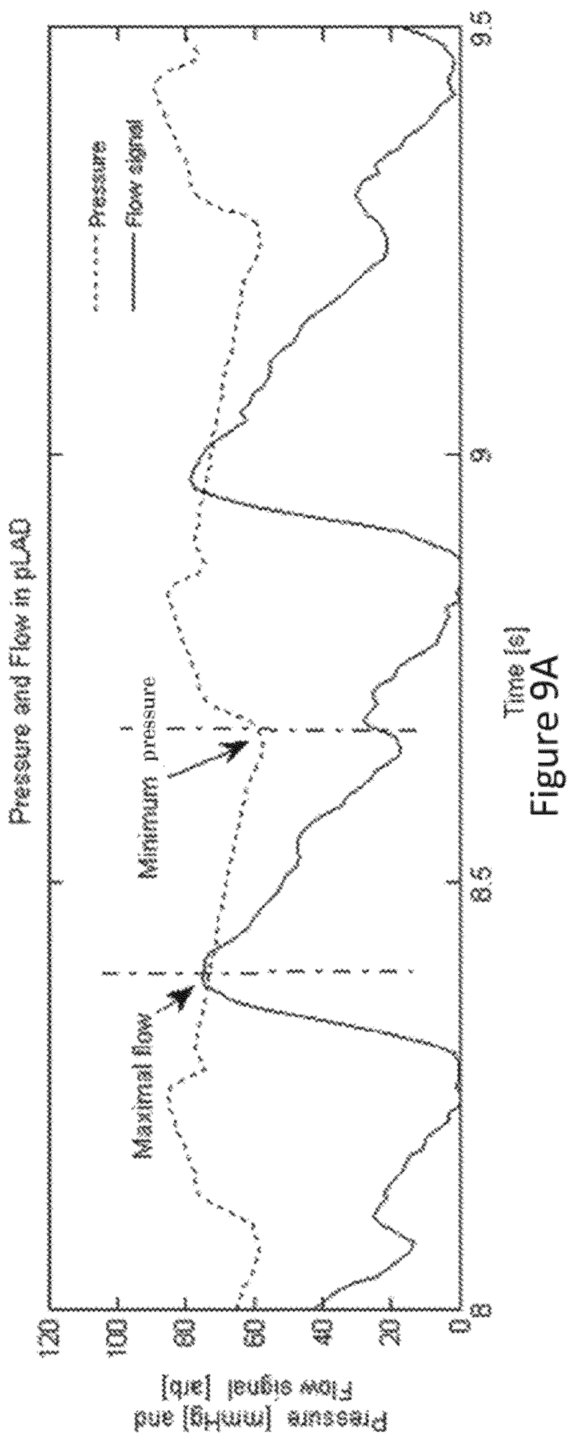
FIG. 9A shows a plot of pressure and flow versus time in the proximal left anterior descending coronary artery in accordance with an illustrative embodiment of the disclosure.
Figure 9B:
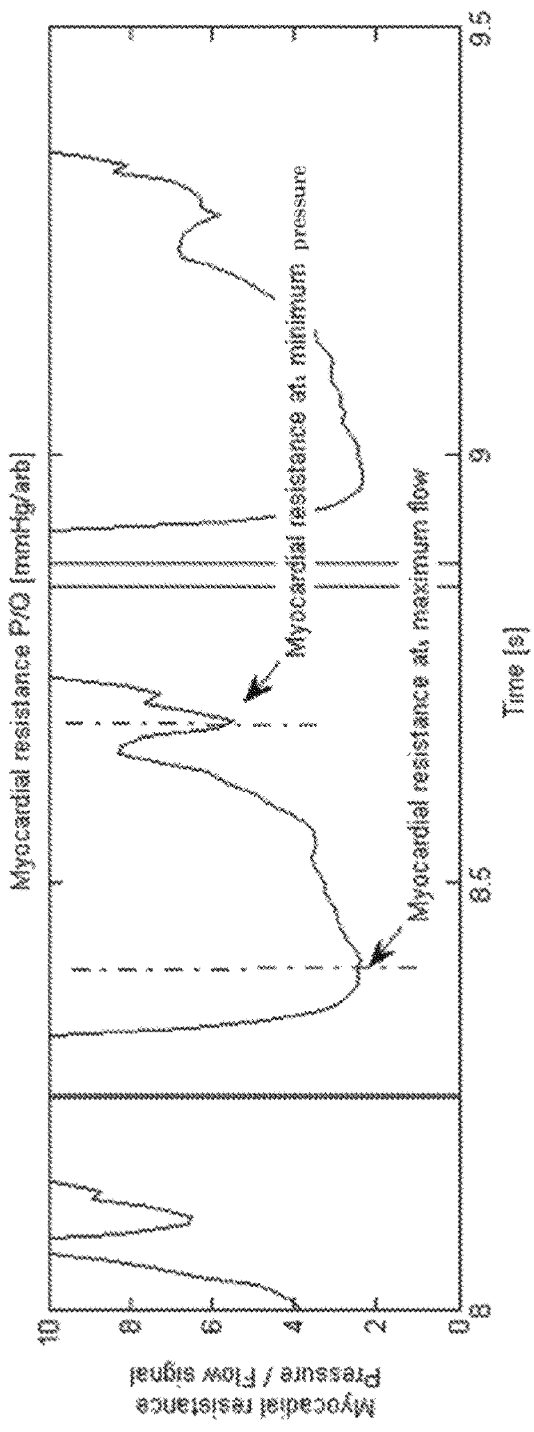
FIG. 9B shows a plot of myocardial resistances versus time in accordance with an illustrative embodiment of the disclosure. The plot of FIG. 9B is derived by dividing the pressure and the flow signal in FIG. 9A.

FIG. 9A shows pressure and flow versus time in the pLAD. FIG. 9B shows myocardial resistances versus time. Instances of maximum flow and minimum pressure are identified. Myocardial resistance is identified at its minimum at maximum flow. For the minimum pressure the myocardial resistance is also identified and plotted. These resistance values can be used to establish trajectories that change over time and displayed to a user on a real time or substantially real time basis along with FFR values and other values obtained using an intravascular pressure and flow probe capable of simultaneously measuring the foregoing parameters. The measurements were obtained with a 40 kg swine.

Figure 10B:
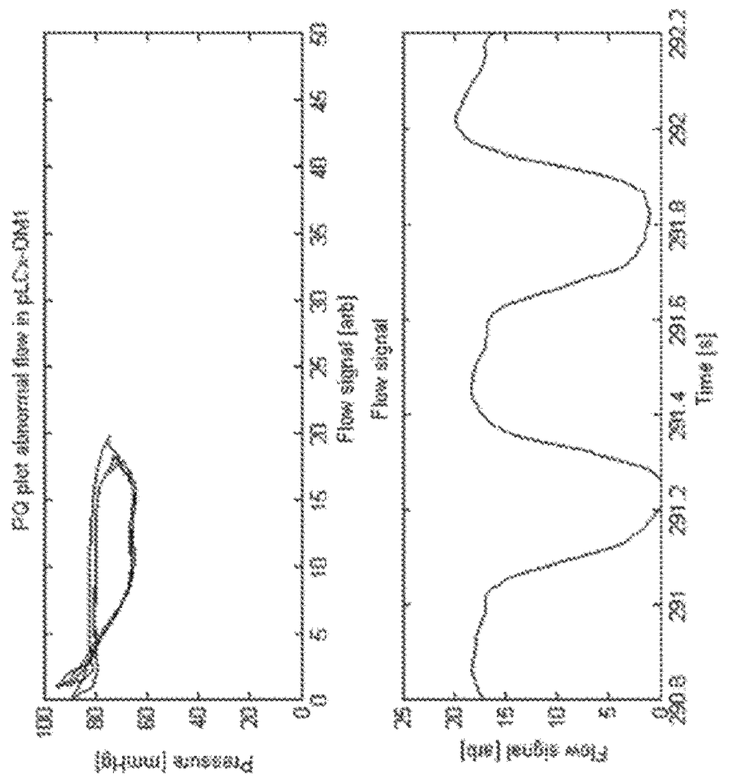
FIGS. 10A and 10B show pressure versus flow plots (top) and pressure versus time plots (bottom) for a normal scenario, FIG. 10A, and an abnormal scenario, FIG. 10B, in accordance with an illustrative embodiment of the disclosure. The abnormal scenario shown in FIG. 10B was created with an occluding balloon to cause a myocardial infarction.
Figure 10A:
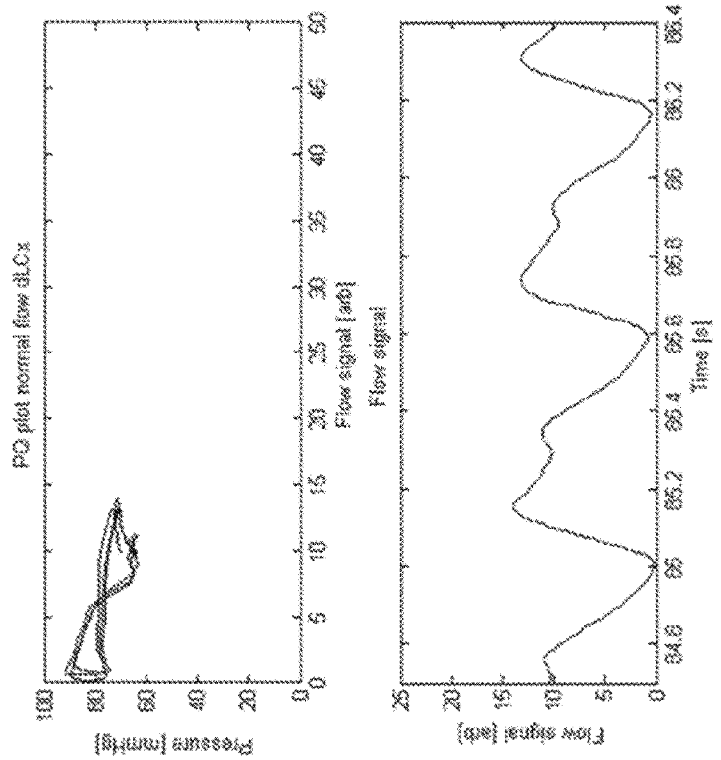

FIGS. 10A and 10B show pressure and flow plots (top) along with a flow versus time plot (bottom) corresponding to a normal scenario (FIG. 10A) and an abnormal flow scenario due to artificially created partial blockage of the marginal branch (FIG. 10B). The pressure (P) versus flow (Q) trajectory shown resembles a tilted figure eight or infinity symbol as plotted in the upper left hand corner of the pressure versus flow of FIG. 10A. In this case the normal scenario of FIG. 10A, the trajectory is substantially uniform at either lobe. In contrast, in the abnormal case of the corresponding plot in FIG. 10B, in which after an artificial blockage is created, the trajectory is asymmetric with the left lobe contracted and the right lobe distended. These can be used as signatures to identify an abnormal cardiac event in one embodiment. Similarly, the double peak flow versus time curve of FIG. 10A changes to a more rounded and higher amplitude curve in the abnormal scenario of FIG. 10B. The amplitude shift and the rounding of the two peaks into one peak can be used as signatures to identify an abnormal cardiac event in one embodiment. The plots can also be tracked over time before, after and during procedures along with the other plots and parameters values described herein to inform a clinician or other user of interest.

Coronary Flow Reserve Diagnostic Systems and Methods

In part, the disclosure relates to methods and systems suitable for determining a coronary flow reserve value in response to one or more of intravascular pressure and flow data or data otherwise correlated therewith. A sensing device (SD) such as a pressure or flow sensor can be used to determine a coronary flow reserve value over time using thermoconvection data. In parallel with a CFR measurement, the same sensing device can be sampled to obtain distal pressure values Pd that can be used with a reference pressure to simultaneously determine FFR values. The various measurement systems described herein such as ICDs can be used to process and display the CFR, FFR, and other parameters described herein. The disclosure also relates to various user interfaces and associated live and review modes by which CFR values and other values can be displayed and plotted.

Some exemplary sources of pressure data can include a pressure sensor such as an electrical or optical pressure transducer. Suitable pressure sensors can be disposed on, in or otherwise relative to a catheter, such as for example a delivery catheter, an intravascular data collection probe, a guide wire, and other suitable devices and systems. CFR values and FFR values can be simultaneously determined and displayed over time as numerical values or time varying curves on a GUI or used as inputs to generate other diagnostic data relating to cardiac system behavior.

In one embodiment, the disclosure relates to an intravascular data collection method. The method allows for diagnostic data and information to be collected and generated. In one embodiment, the method includes tuning or optimizing the temperature signal of an intravascular thermoconvection device when in measurement location of interest; sampling an intravascular thermoconvection device to obtain a baseline thermoconvection signal value; and sampling an intravascular thermoconvection device to obtain Pd values and thermoconvection device values for running FFR and CFR calculations. The outputs of the FFR and CFR calculations can be output on a display of cath lab device or other display such as a touch screen device.

In part, the disclosure relates to methods and systems suitable for determining one or more Coronary Flow Reserve (CFR) and Fractional Flow Reserve (FFR) values simultaneously using a thermoconvection device such as an intravascular pressure and flow sensor and an intravascular data collection and processing system. In addition, in part, the disclosure also relates to determining CFR values using an intravascular probe having a pressure sensor and Constant Temperature Anemometry (CTA) or Constant Excitation Voltage (CVEX) anemometry.

In one embodiment, CFR is the ratio between hyperemic absolute flow and baseline absolute flow. Similarly, in one embodiment, CFVR is defined as the ratio between hyperemic flow velocity and baseline flow velocity. CFR and CFVR are equal by value. The references to CFR in the attached can also be used to perform and display CFVR values as well. As a result, the usage of the term CFR can also be changed to CFVR as used herein to describe CFVR embodiments and measurements, which are also within the scope of the disclosure.

Various data collection and analysis systems are available to obtain information with regard to the coronary system. The data obtained using a device from a blood vessel or derived data from intravascular or extravascular measurements associated therewith can be analyzed or displayed to provide correlations and extrapolations to assist researchers and clinicians. For example, various measurement systems and intravascular probes are available to determine fractional flow reserve (FFR) and Coronary Flow Reserve (CFR). As described herein, a pressure-sensor based device can be used to obtain one or more CFR measurements of a subject.

In one embodiment, pressure data (Pd) and thermoconvection data is collected using an intravascular data collection probe disposed in a subject's artery. Exemplary intravascular data collection probes include catheter-based or catheter delivered probes, guide wire based probes, imaging probes, ablation probes, ultrasound probes, interferometry-based probes and other suitable data collection probes as described herein.

In particular, a pressure sensor can be used to obtain data to measure flow, thermoconvection data, and other cardiac system parameters as described herein. The systems, methods and devices described herein, in part, relate to thermoconvection and hot-film anemometry technologies such Constant Temperature anemometry (CTA) and Constant Excitation Voltage (CVEX) anemometry in some embodiments. As described in more detail below a pressure sensor can be used to sample intravascular data and generate CFR measurements with advantages relative to existing thermodilution approaches.

In way of background, Coronary Flow Reserve measurement can be implemented using a pressure sensor such as a pressure wire or other pressure sensors which can be operated as a thermodilution device. As part of a legacy technique, a CFR value is obtained by injecting a cold saline solution into the coronary artery of interest. In turn, the temperature measuring capability of an intravascular pressure sensor is used to measure the blood temperature rise time (from the onset of cold saline injection into the artery to the return of the temperature to a specific level). This rise time can be converted to a CFR value.

Such legacy thermodilution methods suffer from a lack of accuracy and can be cumbersome to implement. For example, the stated accuracy of an exemplary legacy thermodilution method can result in CFR values that are less than +/−30% accurate. The procedure is cumbersome/time-consuming because it typically requires multiple saline injections of a certain quality to produce enough data for the system software to calculate the CFR value.

The measurement systems, methods and devices described and depicted herein can be used to obtain a signal which is either a measure of pressure sensor chip temperature or power. The chip resistors are heated by electrical current to produce a certain over-temperature compared to the surrounding fluid (blood). The cooling effect of the flowing blood on the chip resistors is measured directly (as a temperature value) or indirectly (as the electrical power needed to keep the temperature of the chip resistors stable).

Figure 11:
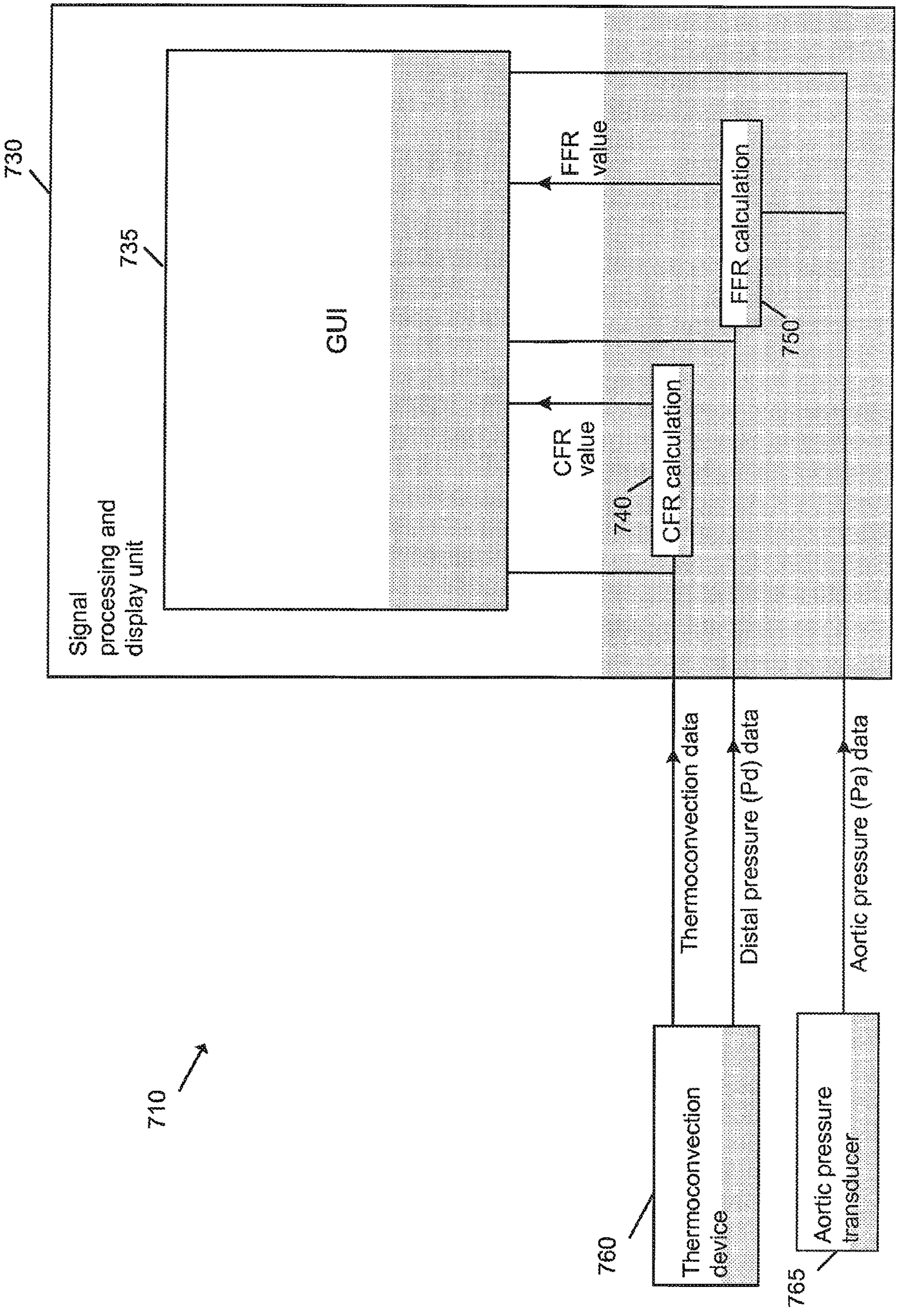
FIG. 11 is a schematic diagram of an intravascular data collection and display system suitable for measuring CFR using an intravascular sensing device in accordance with an illustrative embodiment of the disclosure.

FIG. 11 shows an exemplary system 710 suitable for measuring CFR. In addition, the system 710 can also be used to simultaneously measure CFR values and FFR values. Some non-limiting examples of intravascular data collection and analysis systems 710 or a component thereof can include a RadiAnalyzer, a RadiAnalyzer Xpress, a Quantien, a PressureWire system (such as Aeris 1, Aeris 2 or Certus), an Optis system, a multimodal system such as a combination intravascular imaging and pressure monitoring system, a hemodynamic display having a pressure data input.

In one embodiment, a system suitable for performing thermoconvection CFR measurements alone or simultaneously with FFR measurements such as system 710 of FIG. 11 can include multiple components such as subsystems and devices. As an example, such a system can include a thermoconvection device 760. Examples of such thermoconvection devices can include pressure sensor-based devices such as those described herein. As a specific example, a thermoconvection device can include a pressure sensor Aeris unit adapted to facilitate thermoconvection measurements. Such an Aeris unit can be modified or programmed to use the measurement technology described herein. In one embodiment, the thermoconvection device includes a pressure sensor and is sized and configured to measure distal intravascular pressure and other parameters of interest to measure flow, CFR or FFR or other cardiac system parameters.

As shown with respect to the system 710 of FIG. 11, the exemplary thermoconvection CFR measurement system can also include a reference pressure device 765. The reference pressure device can be used to measure a reference pressure, such aortic pressure in one embodiment. A reference pressure device can include a pressure sensor of a guide or delivery catheter. Such a reference pressure device also receives proximal pressure values (Pa) such as aortic pressure values and transmits them as shown in system 710 as an input for FFR calculations.

The system can also include a signal processing and display unit 730 (such as the Quantien system made by St.

Jude Medical) which receives pressure and thermoconvection (flow) data from the thermoconvection device, either wirelessly or via cable. The unit 730 also receives pressure data from the reference pressure device, e.g. an aortic pressure transducer. In part, embodiments of the disclosure relate to various features of pressure sensing devices, measurement systems, and software relating thereto suitable for determining ratios based upon signals sampled from an intravascular data collection probe such as probes described and depicted herein. Unit 730 can include a display such as a touch screen display or other display to output a GUI along with measured CFR, FFR, and other data of interest from the thermoconvection device 760 and reference pressure sensor 765 (such as an aortic pressure transducer). Thermoconvection data values are temperature values in one embodiment. These values can be generated based upon electrical changes triggered in the thermoconvection device. In one embodiment, the thermoconvection data values are given in degrees C. or other temperature units.

A guide wire-based probe with a semiconductor device that includes components that undergo electrical changes in response to pressure changes is an example of a sensing device that can be used to perform pressure monitoring, flow monitoring, sampling of intravascular data for CFR measurements, and sampling of intravascular data for FFR measurements. The embodiments described herein support methods of determining CFR values using a thermoconvection device and various systems and methods ratio determination and measurements using a guide wire-based probe and associated software and electrical components of a data collection and analysis system 710. A wired probe or a wireless probe can be used to transmit Pd, Pa, and thermoconvection data from a sensor associated with a given probe.

System 710 can perform measurement calculations based on signals sampled from the intravascular probe. Alternatively, system 710 can receive signals encoding results of calculations performed using circuitry or processing elements disposed in the probe such as, for example, in the probe's proximal connector. System 710 can also include software, control systems, and data analysis and display devices and processors suitable for graphing and displaying pressure values, FFR values, CFR values, sampled Pa values, sampled Pd values, moving averages, and other values relating to the foregoing.

The data collection and analysis system 710 can include a processor such a microprocessor, a memory, and one or more software modules, circuits, or hardware components such as a CFR hardware component or CFR software module 740. System 710 can also include a FFR hardware component or FFR software module 750. These components or software routines are configured to receive intravascular data and simultaneously determine CFR and FFR values, if such information is selected for display on an interface screen. The CFR hardware or software module can include one or more of the methods and associated empirically determined functions or mathematical relationships described herein with regard to determining a CFR value using data sampled from a sensing device (SD) such as a thermoconvection device as described in with regard to temperature and flow sensing guide wire-based probes.

In one embodiment, the thermoconvection data is the relative temperature changes of the heated measurement resistor, which is a measure of the flow changes around the resistor/device. Additional details relating to systems that can be used to obtain thermoconvection data and thermoconvection devices that are based upon pressure and flow sensing devices are described and depicted herein.

The CFR measurement runs in parallel with the FFR measurement. For example, the CFR measurement software can be implemented as one or more software routines or methods as an extension to the pressure sensor signal processing software and/or the one or more software components running in hardware components and devices of the system of FIG. 11.

FFR Data and Thermoconvection Data CFR Procedure

Figure 12A:
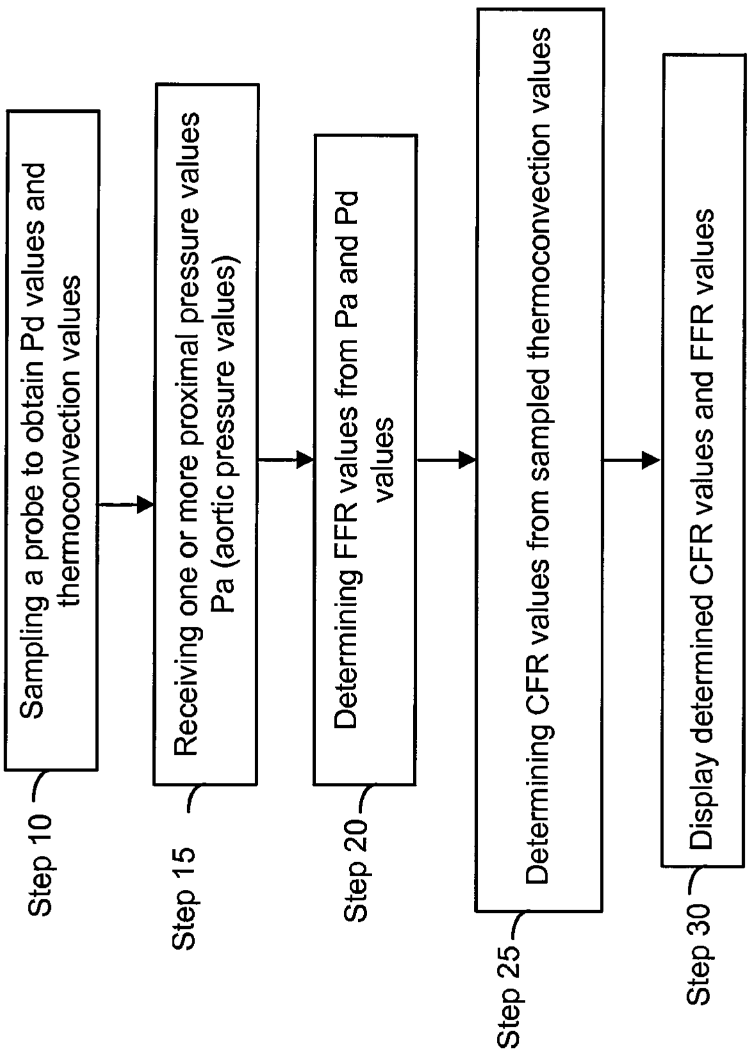
FIG. 12A is a flow chart of an exemplary method of intravascular data analysis and display in accordance with an illustrative embodiment of the disclosure.
Figure 12B:
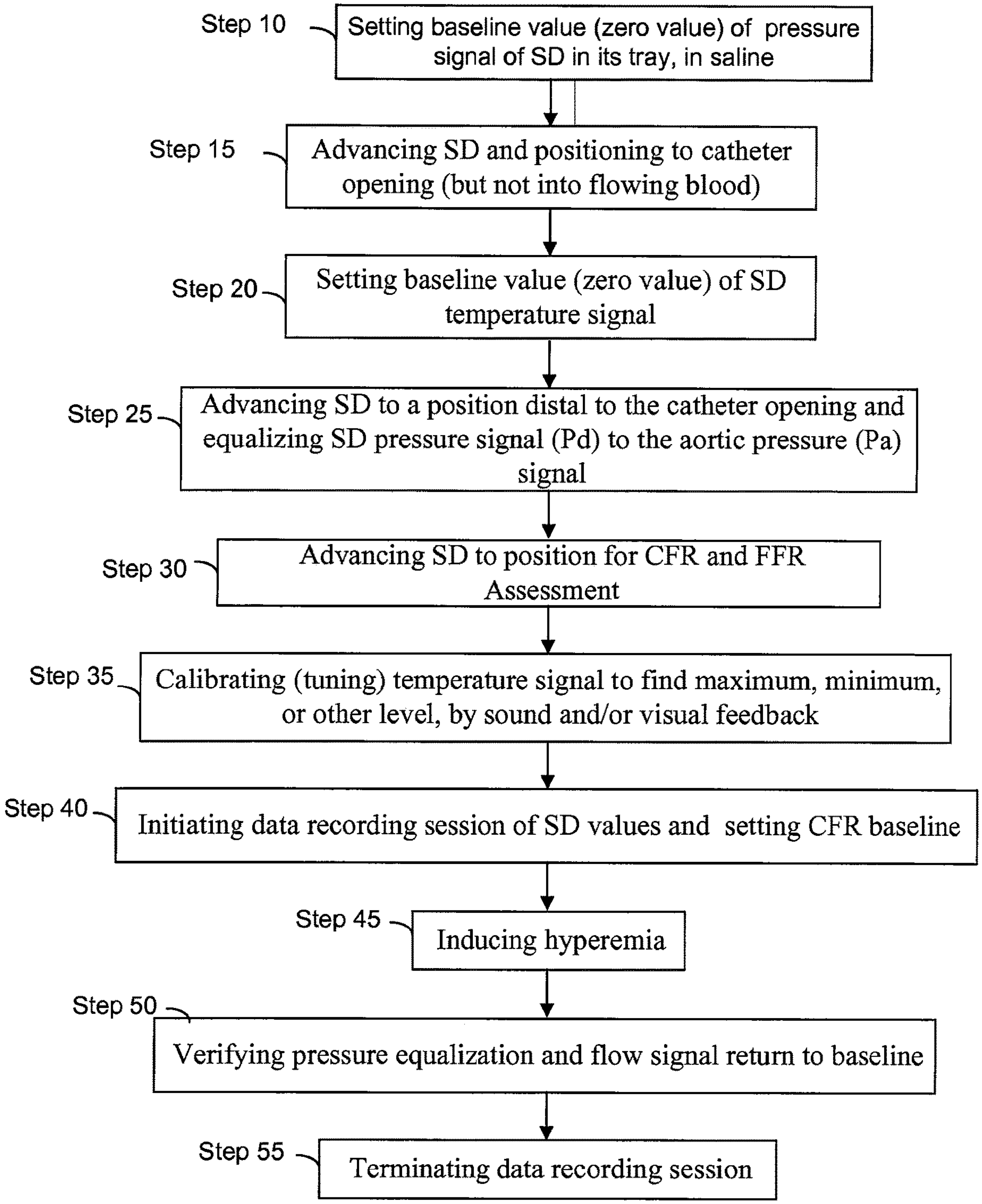
FIG. 12B is a flow chart of an exemplary method of intravascular data analysis and display in accordance with an illustrative embodiment of the disclosure.

An exemplary set of steps of a combined FFR and Thermoconvection CFR measurement procedure is described with regard to FIG. 12B. These steps can be performed using the system of FIG. 11 and those described herein. The associated graphic user interface screens associated with diagnostic data outputs are shown in FIGS. 13A-13D and 5A-5D.

In FIG. 12B, an exemplary series of method steps that can be performed to determine one or more CFR values and one or more FFR values for a subject is shown. Steps 10 to 55 need not all be performed in a given embodiment. Further, some steps can be performed in a different order or simultaneously with other steps.

As part of this method, setting baseline value or otherwise establishing a zero value of pressure signal of a sensing device (SD) such as an intravascular pressure in its tray, in saline or another buffer is performed (Step 10). Advancing SD and positioning to catheter opening (but not into flowing blood) is performed (Step 15). Setting baseline value (zero value) of SD temperature signal (Step 20) is performed. Advancing SD to a position distal to the catheter opening and equalizing SD pressure signal (Pd) to the aortic pressure (Pa) signal is performed (Step 25). Advancing SD to position for CFR and FFR Assessment is performed (Step 30). Calibrating (tuning) temperature signal to find maximum, minimum, or other level, by sound and/or visual feedback is performed (Step 35). This calibration or tuning step can be implemented in software or can be software facilitated with visual or auditory cues indicative of a calibrated state being present to an operator when adjusting controls to find a temperature signal level. In one embodiment, tuning or calibrating refers to the intravascular device being physically moved radially inside the blood vessel in order to position the device in optimal or other desired flow level. Optimal flow is typically identified by the temperature signal settling on a maximum or minimum level. The temperature signal level is tuned to achieve a relative maximum or minimum value or other threshold value.

Still referring to the method depicted in FIG. 12B, the method can also include initiating a data recording session of SD values and setting a CFR baseline (Step 40). When obtaining a CFR measure, in one embodiment, inducing hyperemia is performed (Step 45). Thus, in step 45 as an example, an introduction of a hyperemic agent such as adenosine is performed with regard to the subject being monitored to determine CFR and FFR values. Verifying pressure equalization and flow signal return to baseline is performed (Step 50). Finally, in one embodiment, once a desired set of sampled probe values has been obtained or a parallel diagnostic or treatment has concluded, terminating or stopping the data recording session occurs (Step 55). In one embodiment, the baseline level is level 1 or another established baseline value.

The Graphical User Interface (GUI) of a FFR measurement system such as for example a Quantien system or the system of FIG. 11 can incorporate one or more processors or control systems to provide user controls for zeroing the pressure sensor temperature signal. In addition, such user controls can be used to set the CFR baseline value, as well as new graph windows for signal tuning and CFR tracings. The system would also be extended with a sound interface/speaker for the audio tuning step.

In various screenshots, one or more regions or panels of a GUI or other display output of the system of FIG. 11 or of the other systems described and depicted herein, shows recorded measurement for simultaneous FFR and CFR assessment. For example, simultaneous display of FFR and CFR data is depicted with Fv/Fv-B (Flow/Flow_baseline ratio), which is the output from the CFR calculation being displayed in various interface figures along with FFR values in review mode.

In part, the disclosure includes various features that represent advances and new diagnostic information and methodologies to users with regard to CFR and FFR. One such feature is the process of determining a CFR value based upon the following relationship CFR=b^((x_hyperemic−x_baseline)/c). Further, this CFR relationship can be evaluated based on measured pressure sensor temperature or power signals from an intravascular pressure probe such as herein. As noted herein with regard to FIG. 11, it is advantageous to run CFR software-based method or hardware component 740 in parallel with pressure sensor pressure signal processing as part of FFR software-based method or hardware component 50 to facilitate simultaneous FFR and CFR measurement and subsequently simultaneously display the FFR and CFR values. The method steps described herein, such as with regard to the process flow of FIGS. 12A and 12B and the associated user interfaces and plots of CFR data and the simultaneous plotting of FFR and CFR changes over time, are additional features that offer enhanced diagnostic information to a user.

Figure 14:
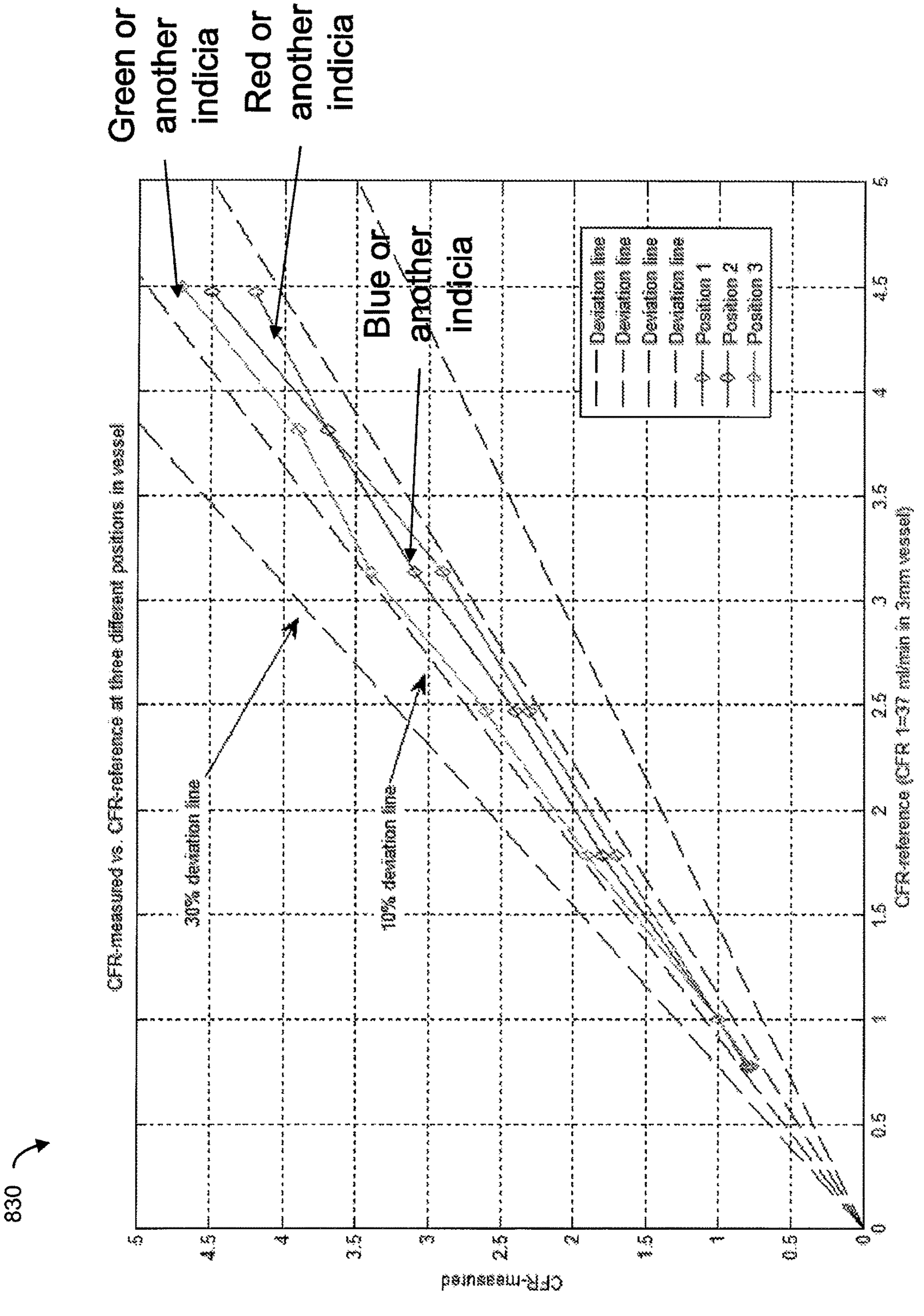
FIG. 14 is graph showing the performance of a system in accordance with an illustrative embodiment of the disclosure used to determine CFR values compared to reference CFR value.
Figure 15A:
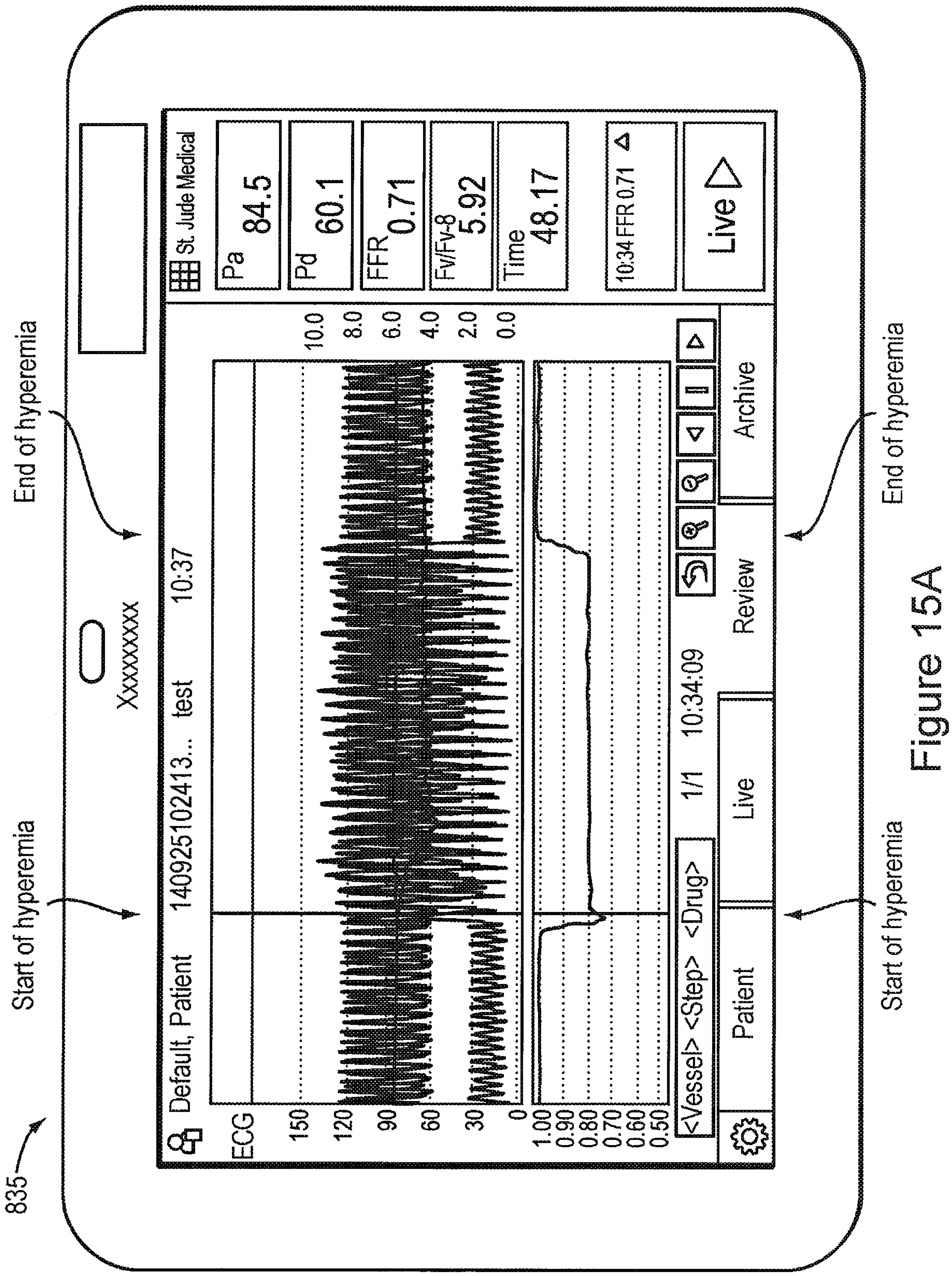
FIGS. 15A-15D are exemplary user interface and data display screenshots in accordance with an illustrative embodiment of the disclosure.
Figure 15B:
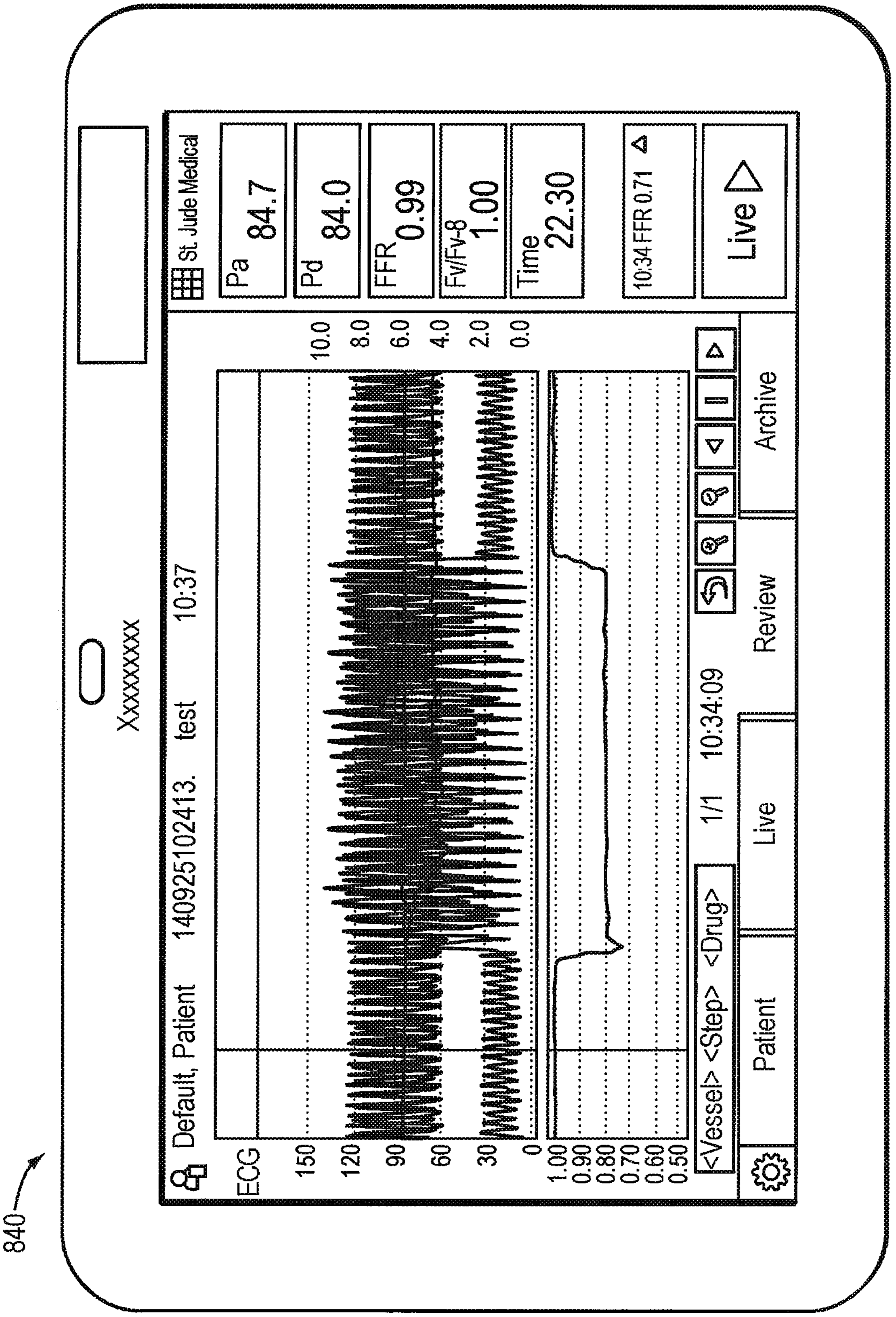
Figure 15C:
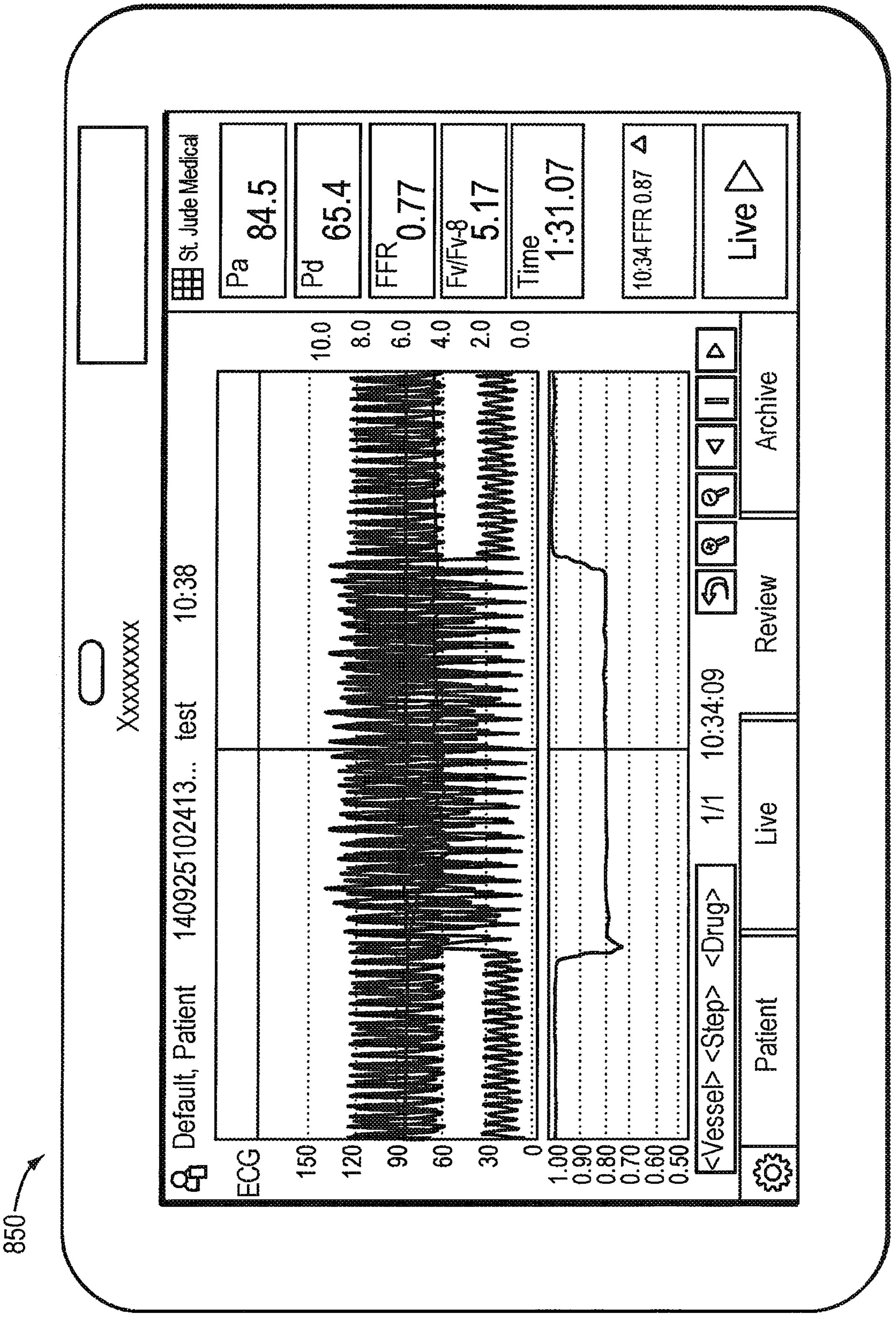
Figure 15D:
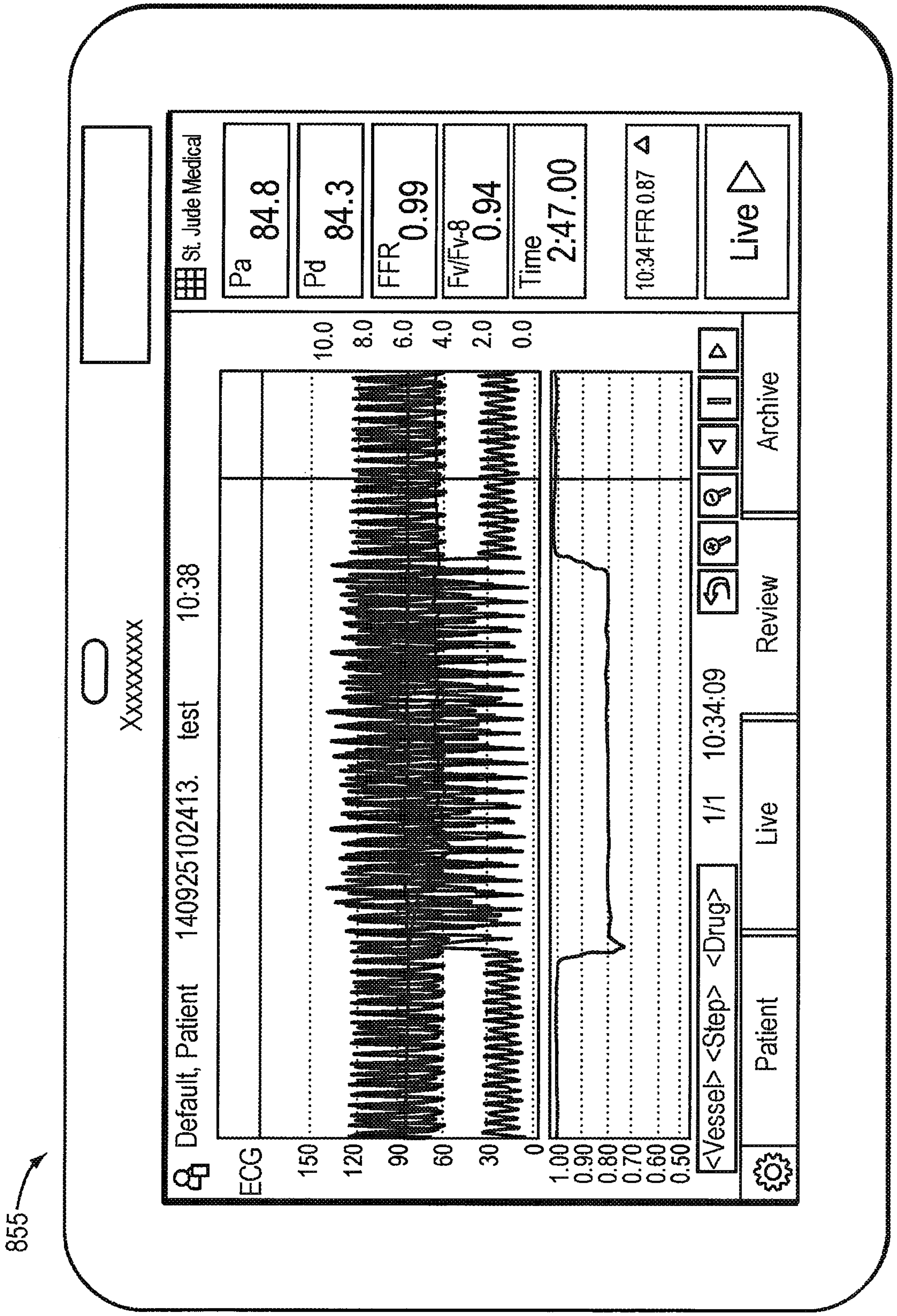

FIG. 14 shows the performance of CFR measurements performed with a PressureWire Generation 8 unit, provided by St. Jude Medical, using thermoconvection flow measurement on an Aeris 2 platform, versus a reference CFR to serve as a comparison known CFR value. The measurement was performed in a 3 mm tube at three different positions (shown in red (position 1), blue (position 2), and green (position 3)). In one embodiment, during measure the PressureWire is rotated and a maximal flow signal level is determined prior to each CFR measurement. The results show that the maximum deviation is within 10% for all positions. This compares favorable relative to the 30% error margin specified for PressureWire CFR measurements using the thermodilution method.

Visual Representations of Intravascular and other Cardiac System Data

Various exemplary Graphical User Interface (GUI) or display outputs are depicted in FIGS. 13A to 13D and 15A to 15D that include data sets generated using intravascular measurements such as one or more of a pressure, temperature, flow measurement, or measurements derived therefrom or correlated thereto. In one embodiment, there is a plurality of modes for the intravascular data processing and display system outputs. By way of example, a live mode and a review mode are discussed in more detail as follows.

Live Mode—GUI

Figure 13A:
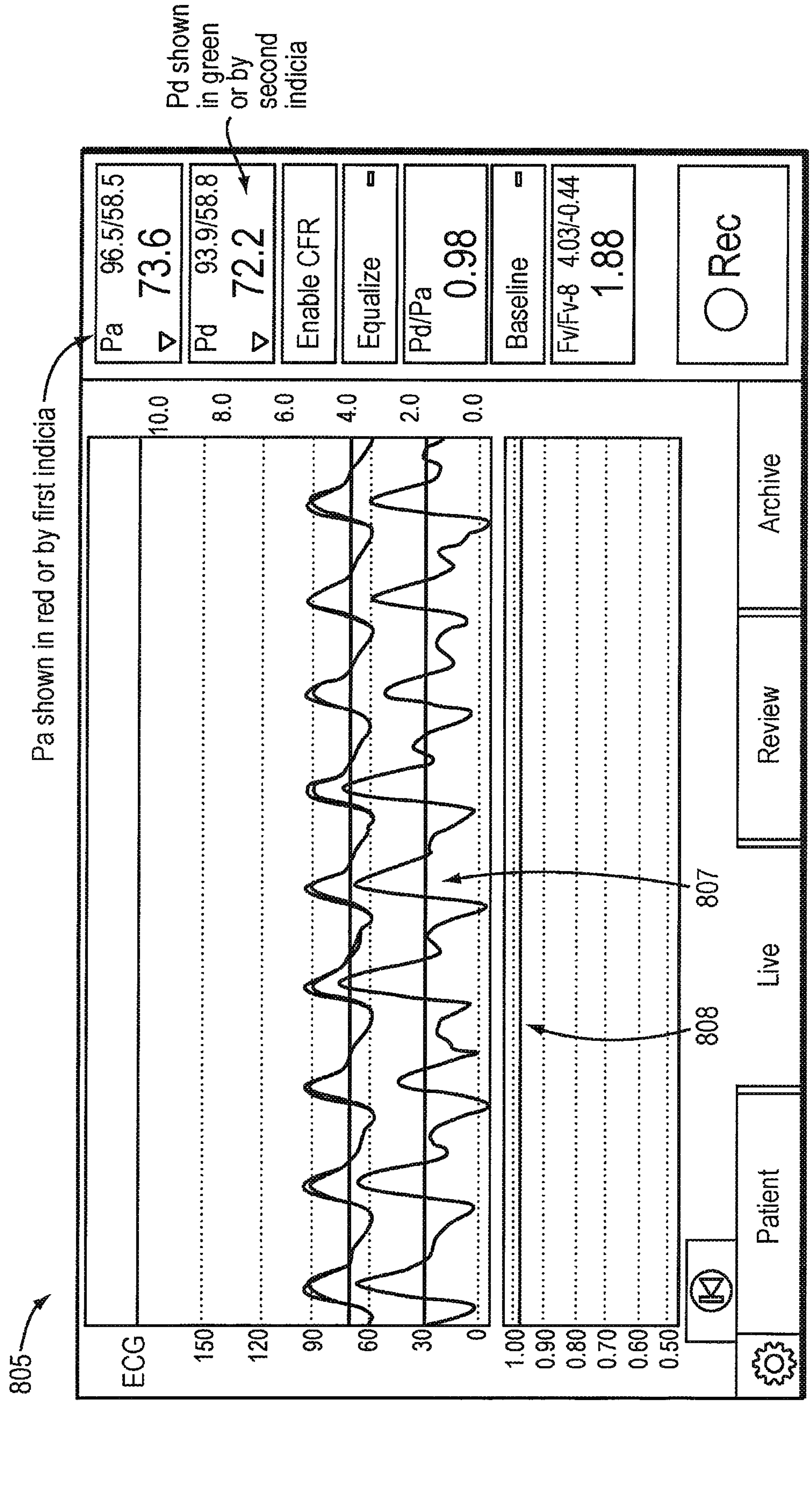
FIGS. 13A-13D are exemplary user interface and data display screenshot during review mode in accordance with an illustrative embodiment of the disclosure.

FIG. 13A shows an exemplary GUI 805 in live mode with data being displayed as it is sampled by an intravascular probe and processed by a measurement system such as system 710 or other ICDs described herein. The GUI is typically displayed on a touch screen and various elements on the interface can be activated and deactivated and otherwise interacted with to change the display, calibrate the system, and make other modifications. In the live mode shown, real-time data curves and numerical values are displayed which provide real time insights to a user reviewing such data, such as may be the case before, during, or after another diagnostic procedure of treatment.

As shown in FIG. 13A, various graphs or plots can be shown with regard to measured cardiac system data. The upper graph window shows phasic Pd (using one color such as green or second indicia), Pa (using another color such as red or first indicia), and their respective average values. The white phasic curve 807 is the thermoconvection (flow) data, mapped to the current flow ratio value (see Numerical information below). The average value of the phasic curve matches the present flow ratio value (1.88). The lower graph window displays a colored line 808 such a yellow line or another indicia, reflecting the current Pd/Pa value (0.98). The right-hand panel displays the following numerical information from top to bottom:

- Pa average, with Pa maximum and Pa minimum shown with smaller digits.
- Pd average, with Pd maximum and Pd minimum shown with smaller digits.
- Pd/Pa value, based on average values of Pd and Pa.
- Fv/Fv-B (Flow/Flow_baseline ratio), which is the output from the CFR calculation. In one embodiment, the value is not called CFR in Live mode since the definition of CFR is the flow ratio relative to baseline flow at maximum hyperemia. These definitions can be modified and changed based on expectations of users of the systems. In one embodiment, maximum hyperemia is present during only a short portion of the measurement cycle. In one embodiment, Pd/Pa is not identified as FFR in Live mode.

The GUI of FIG. 13A includes various user control buttons Rec (record), Equalize, Patient, Live, Review and Archive buttons and menus. The exemplary GUI 805 of FIG. 13A also includes new controls and buttons with regard to the Enable CFR control interface. The Enable CFR control can be adjusted by the user to enable and disable FFR+CFR mode, i.e. the user can choose between FFR mode and FFR+CFR mode. The GUIs shown herein are implemented using touchscreens or other controls and input devices in various embodiments.

The Baseline control (shown in FIG. 13A) can be used to open a new menu where the user can choose between Tune and Set Baseline. In turn, the Tune control can be used to activate thermoconvection signal tuning, using both visual information (a graph) and audio (a sound signal) to give the user a chance to optimize the thermoconvection signal, i.e. to position the device in an optimal vessel position. The Set Baseline control can be used to instruct the software to store the present average of the thermoconvection signal as $T_{bas}$ for the CFR calculation.

Review Mode

Figure 13B:
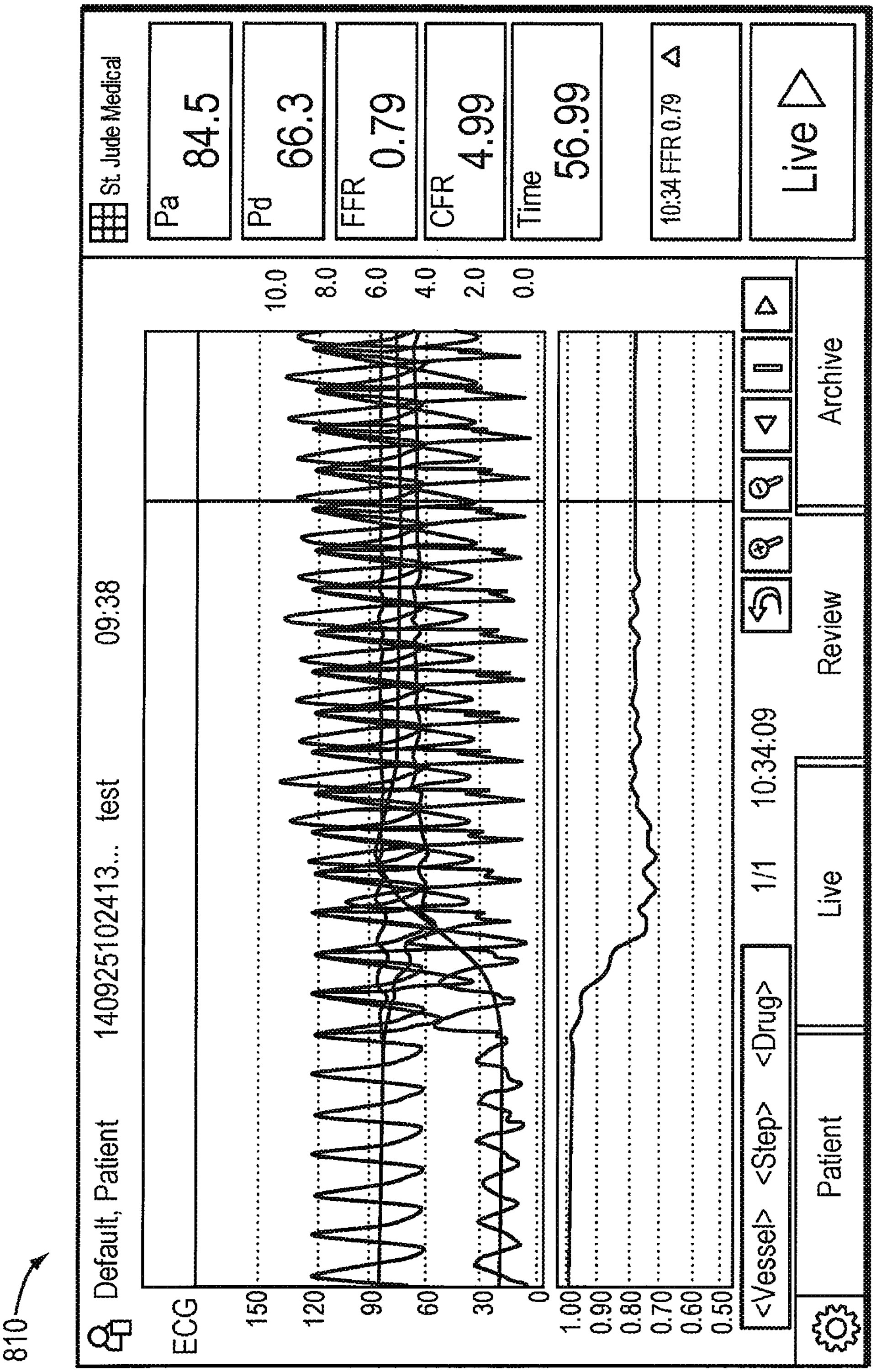
Figure 13C:
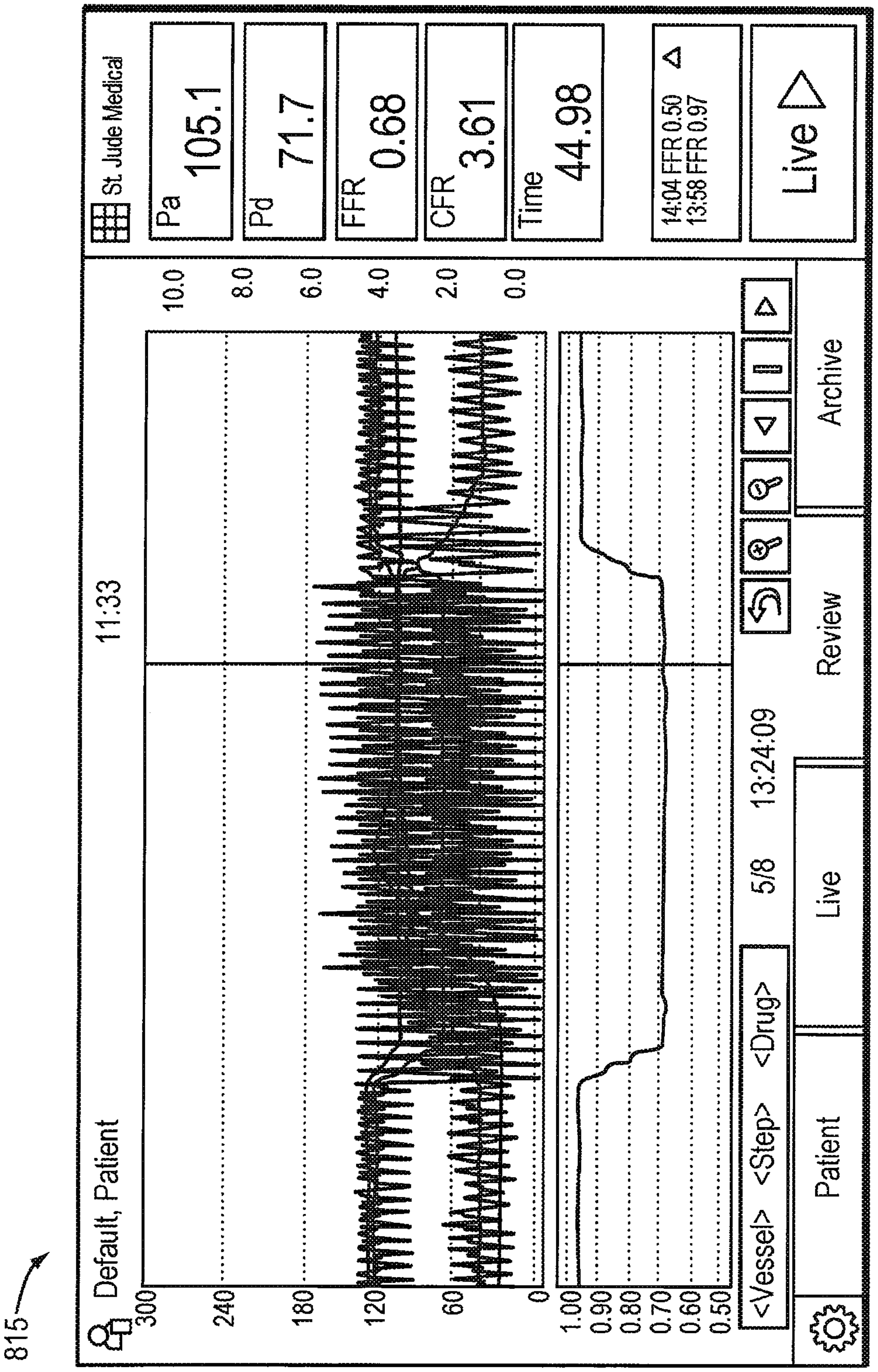
Figure 13D:
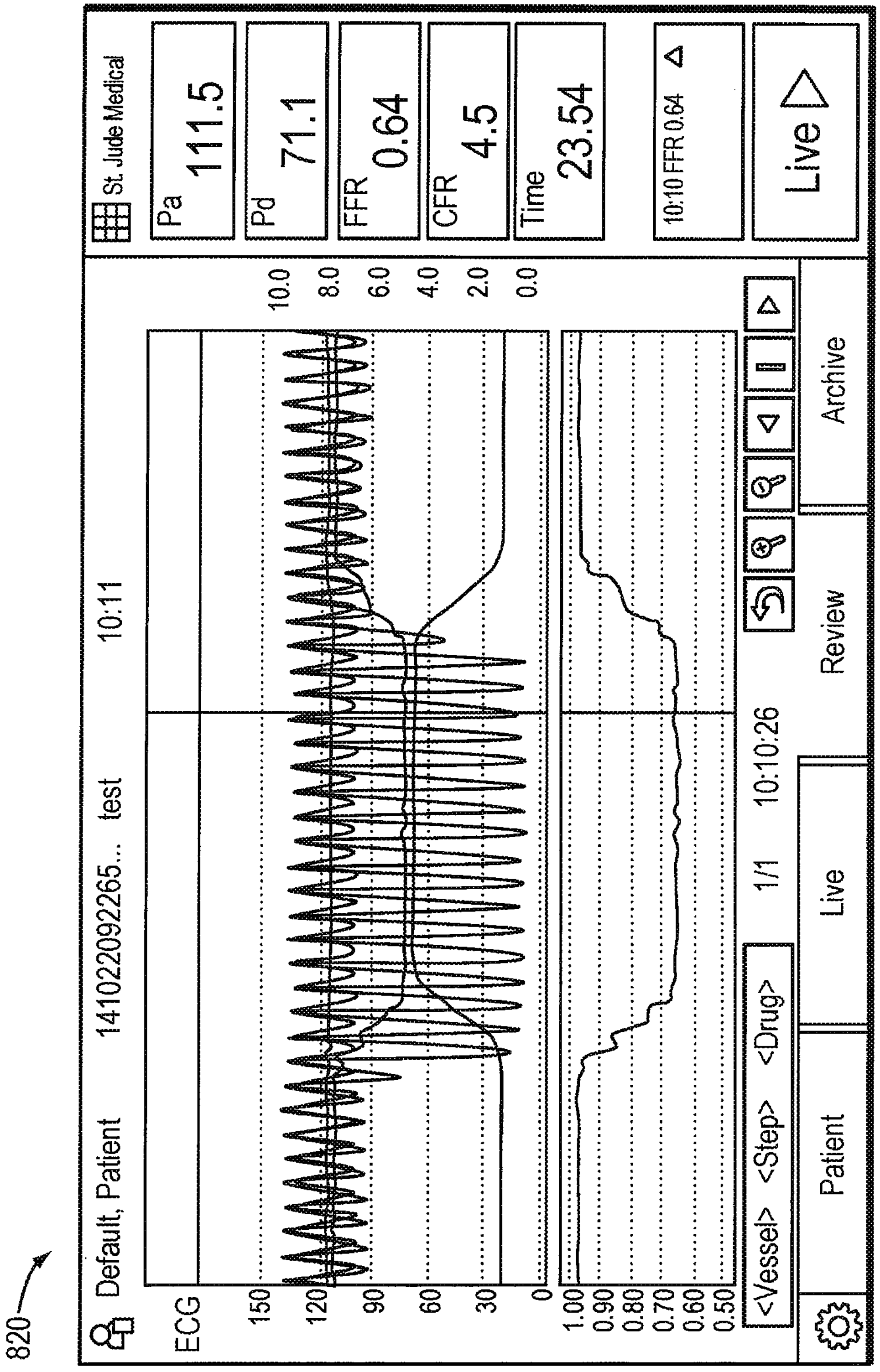

In Review mode as shown in FIGS. 13B, 13C, and 13D, measurement recordings are presented. The screen shows how the pressure and flow ratios start at 1 (baseline flow) and then at the onset of hyperemia shift to their respective hyperemic levels, i.e., for FIG. 13B, a pressure ratio of around 0.8 and a flow ratio of 5.0. Note that the flow ratio scale is shown on the right-hand side of the top graph window, ranging from 0.0 to 10.0. On the Review screen the ratios are called FFR and CFR, assuming that the user uses the cursor to slide across the recording to identify maximum hyperemia (which is where the two ratios become FFR and CFR).

CFR Determination—Thermoconvection Data

As described herein, a number of possible transfer functions from the blood flow value to the measured pressure sensor signal are listed. In one embodiment, a transfer of the following form is used: x=a+c*log bQ, where the base b of the logarithm is unspecified, x is the measured Pressure sensor temperature signal or chip power, a is an offset value, c is a gain factor, and Q is the value of the blood flow. Both a and c are dependent on the position of the pressure sensor chip in the blood vessel. The inverse of this function is used to calculate a flow value using the measured pressure sensor signal: Q=b^((x−a)/c). CFR (Q_hyperemic/Q_baseline) can then be calculated as b^((x_hyperemic−x_baseline)/c) as described in more detail herein. In one implementation, the offset value (a) is unnecessary for the CFR calculation.

The CFR calculation is based on one of the transfer functions described above, namely:

$$T = a + c * lnQ \tag{1}$$

where T is the measured temperature of the temperature variable resistor of the thermoconvection device, Q is the flow, and a and c are constants dependent on the device and the position of the thermoconvection device inside the flow vessel. To calculate a flow value given a measured thermoconvection device temperature, the inverse of (1) is used:

$$Q = e^{\frac{T-a}{c}} \tag{2}$$

In one embodiment, the definition of CFR is:

$$CFR = \frac{Q_{hyp}}{Q_{bas}} \tag{3}$$

where $Q_{hyp}$ is hyperemic coronary flow and $Q_{bas}$ is baseline (resting) coronary flow. The CFR index is thus a value of the maximum achievable blood flow increase ratio of the coronary system.

By inserting (2) in (3) we get:

$$CFR = \frac{e^{\frac{T_{hyp}-a}{c}}}{e^{\frac{T_{bas}-a}{c}}}$$

Where $T_{hyp}$ is the measured temperature at hyperemic flow, and $T_{bas}$ is the measured temperature at baseline flow. This requires that the thermoconvection device is kept stable in a specific measurement position during both baseline and hyperemic flow (or else the a and c constants will not be valid for both hyperemia and baseline). Hyperemia can be visualized in FIGS. 15A-15D as the negative plateau region shown in the lower window of the FFR data plot and the positive plateau shown in the middle of the screen (see FIG. 15A) with respect to the Fv/Fv-B (Flow/Flow_baseline ratio) plot. The vertical line shown around the left third of the screenshot of FIG. 5A represents the start of hyperemia. Simplification of (4) using logarithm laws gives:

$$CFR = e^{\left(\frac{T_{hyp}-a}{c} - \frac{T_{bas}-a}{c}\right)}$$

Further simplification, leading to the final CFR function, as used by the CFR calculation software:

$$CFR = e^{\frac{T_{hyp}-T_{bas}}{c}} \tag{5}$$

Note that the constant a is not necessary for calculating CFR. Constant c however is crucial, and is specific to the thermoconvection device and the position of the device in the flow vessel. Also note that the CFR value is a ratio of flow relative to the baseline flow, meaning that the $T_{bas}$ value acts as a constant during the specific CFR calculation. The value of $T_{bas}$ is indirectly provided by the user; when the coronary flow is at resting level, and the operator has positioned the thermoconvection device in an optimal measurement position, the GUI button Set Baseline is pressed and the software stores the current thermoconvection value (averaged) as $T_{bas}$.

The function can be written in a more general form by not using the base of the natural logarithm (e), but the base of any logarithm (b):

$$CFR = b^{\frac{T_{hyp}-T_{bas}}{c}} \tag{6}$$

Intravascular data collection devices can be used to generate and receive signals that include diagnostic information relative to the blood vessel in which they are used. These devices can include without limitation imaging devices, such as optical or ultrasound probes, pressure sensor devices, and other devices suitable for collecting data with regard to a blood vessel or other components of a cardiovascular system.

In part, the disclosure relates to intravascular data collections systems and related methods by which intravascular data collected by an intravascular probe can be transformed or analyzed by a processor-based system. The results of such analysis and transformation can be displayed to an end user in various representations such as a display that is in communication with or part of a system such as a pressure monitoring system or intravascular data collection system. Examples of such systems are shown for example in FIGS. 1A-2B, 5A-5E, 11, 13A-13D, 15A-15D and as otherwise depicted in whole or in part in other figures.

In one embodiment, the display consoles used to display user interfaces such as touch screen interfaces and one or more of a flow velocity, a maximum flow, a minimum flow, a flow threshold, a relative extremum of flow one or more fractional flow reserve (FFR) values, coronary flow reserve (CFR) values, coronary flow velocity reserve (CFVR) values, instantaneous flow reserve (IFR) values, and one or more index of myocardial resistance (IMR) values in one or more panels, user interface regions, or as values or as a plot or graph re a component of the system in one embodiment. The display device, console or the cart or other housing to which they are attached or in electrical or wireless communication with and can include one or more microprocessors to perform one or more of the steps described herein and process intravascular signals from a probe as recited herein.

These figures and user interface screens can be used with intravascular and angiography images to make stent decisions, identify regions of interest from a diagnostic standpoint, and inform other cardiac system treatment decisions as diagnostic tools.

In one embodiment, a user of the systems, methods, and displays disclosed herein can review a given display of FFR and CFR values over time, before a procedure, during a procedure, or after a procedure to diagnose stenosis severity, stenosis location, guide treatment strategy, evaluate treatment effect, and assess the need for additional therapy post procedure.

Flow Peak/Flow Threshold Measurement and Assessment Embodiments

A pressure or flow sensor or other sensing device can be used in conjunction with a system such as an integrated cardiology display or other systems as described herein to determine one or more categories of intravascular data overtime using thermoconvection data or flow data obtained using a flow sensor or from other measurements correlated with flow data. Mechanical, optical, and other flow sensors can be used in addition to thermoconvection-based sensors. The system can include a signal processing and display unit (such as a RadiAnalyzer system, a RadiAnalyzer Xpress system, a Quantien system, an Aeris system, a Prestige guide wire-based probe system, ComboMap® Pressure and Flow System, and other intravascular pressure sensing or FFR determining devices and systems). In one embodiment, a pressure or flow sensor is used that is part of an intravascular probe. The system can also include or be in communication with a reference pressure device such as a catheter suitable for measuring a proximal or distal pressure value. The reference pressure device can be used to measure a reference pressure, such as an aortic pressure in one embodiment. A reference pressure device can include a pressure sensor of a guide or delivery catheter.

The same sensing device can be sampled to obtain distal pressure values Pd that can be used with a reference pressure to simultaneously determine FFR values. Such a reference pressure device also receives proximal pressure values (Pa) such as aortic pressure values and transmits them for subsequent analysis and calculations to a suitable system such as described herein and as depicted in exemplary embodiments in FIGS. 1A-2B, 5A-5E, 11, 13A-13D, 15A-15D.

In one aspect, the disclosure relates to using intravascular data obtained to detect a flow threshold such as a flow peak or other relative extrema, inflection point, first derivative value, or second derivative value as non-limiting examples during a cardiac cycle using one or more techniques described herein. In turn, the detected flow threshold such as a flow peak (or other value or point) can be selected as an indicator for a measurement system such as to calculate a pressure ratio/difference. Additional details relating to exemplary process steps are described with regard to FIGS. 16, 17A, 17B and the plot of exemplary pressure and flow curves along with Pa and Pd values on a per cardiac cycle basis.

In part, embodiments of the disclosure relate to various features of pressure sensing devices, measurement systems, and software relating thereto suitable for determining ratios based upon signals sampled from an intravascular data collection probe. The signals, which can be various values such as pressure or flow thresholds (user specified via an interface or automatically identified by the measurement system) being used to select a point or a time period during the cardiac cycle. This point can be the max value of a set of flow values obtained with a probe. The point or time period selected is used to perform a measurement or select a previously obtained measurement that includes a distal pressure value or other parameters including without limitation a flow velocity, a maximum flow, a minimum flow, a flow threshold, a relative extremum of flow, one or more fractional flow reserve (FFR) values, coronary flow reserve (CFR) values, coronary flow velocity reserve (CFVR) values, instantaneous flow reserve (IFR) values, and one or more index of myocardial resistance (IMR) values. A flow threshold can be specified as a level greater than or equal to which a measure level of flow is categorized as a peak or high flow.

Alternatively, the largest flow value or absolute value of measure flow can be identified as the flow threshold or peak flow value at which point in a cardiac cycle one or more pressure values or other intravascular parameters of interest are measured. The selection of a flow threshold provides a point relative to which a pressure difference, a flow value, or other values described herein such as statistical values and other metrics can be obtained using a sensing device. The diagnostic data collected at each flow threshold, such as a peak or maximum flow, for example, can then be displayed as a value, plotted or otherwise processed and used to generate correlated values which in turn can be displayed or plotted.

Diagnostic methods suitable for performing stenosis assessment in coronary arteries and related thermoconvection systems and devices are described herein. The systems and methods can be used to detect a flow peak (or other value or point as described herein) which can serve as a guide to identify points in time or an event in a cardiac cycle of interest. These points in time or events can be used as the basis for measuring a pressure ratio difference during the event or point in time. These methods and systems can be used to perform non-hyperemic measurements such as a non-hyperemic or resting FFR value.

In some of the currently used techniques to determine an FFR independent of flow data or other metrics associated with a flow peak or other time point in the cardiac cycle, assumptions are made to determine an FFR value such as defining a region where high flow normally appears. In contrast with such a definitional approach, instead of simply specifying such a region to select for data collection, an anemometry-based or other flow measurement-based system and method as described herein can be used to accurately measure when high flow or peak flow occurs or another metric correlated with or derived using such a measured flow value. In some embodiments, this is referred to peak flow which can correspond to the occurrence of a maximum blood flow which is associated with a maximum blood flow peak or other relative extremum during the heart cycle.

Figure 18:
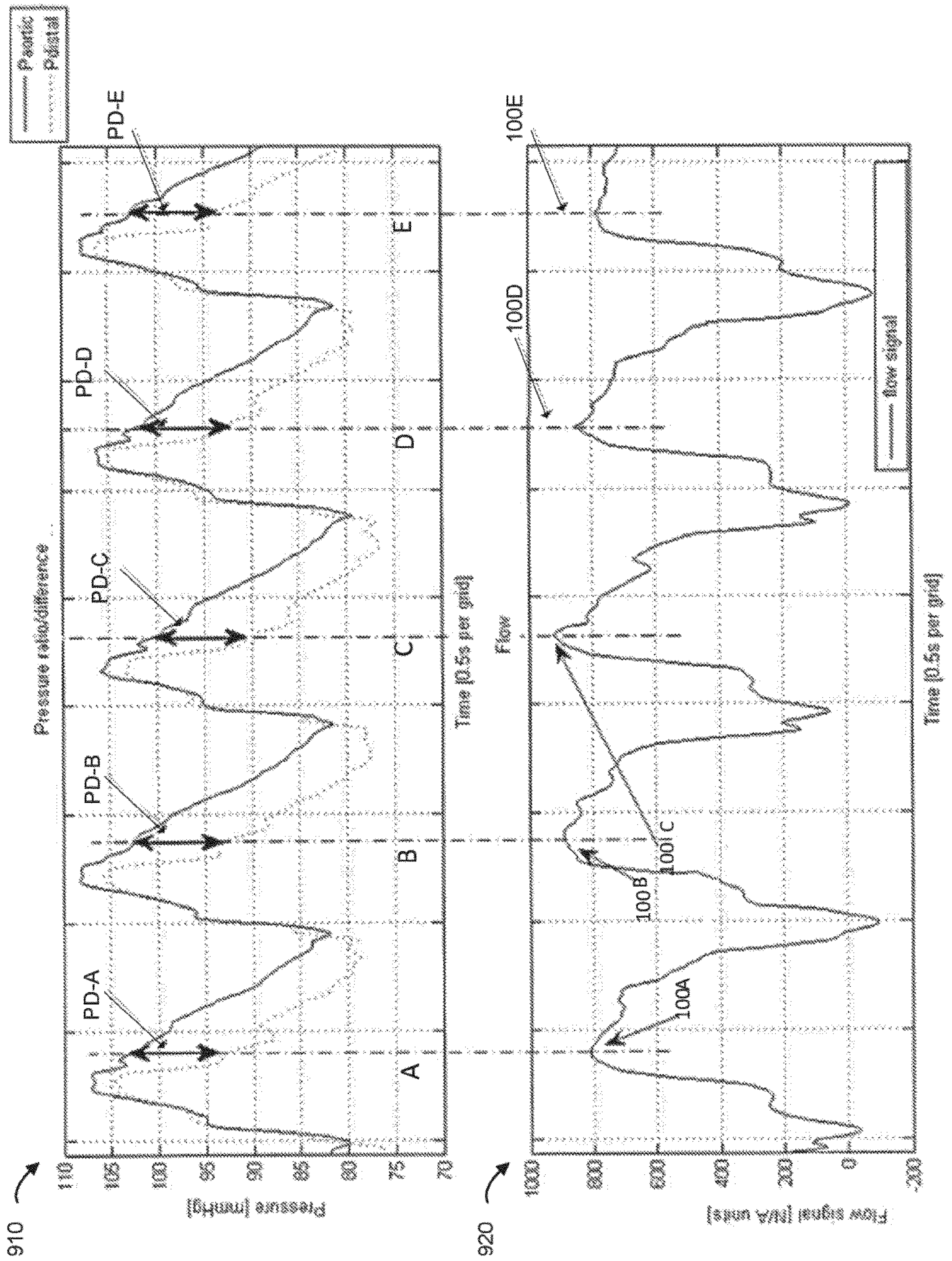
FIG. 18 is a plot of pressure ratio and pressure differences obtained at a plurality of flow thresholds obtained at different points in time using a sensing device versus a pressure measurement (top) and a flow measurement/measurement correlated with a flow value (bottom) in accordance with an illustrative embodiment of the disclosure.

The position of interest (at a flow threshold such as a maximum blood flow peak) can always be found and the pressure drop is measured at that point in the heart cycle. The appearance of the flow peak can be located anywhere in the heart cycle and the ratio of the cycle and thus is not determined by pre-selecting a region based on an expectation relating to the behavior of the heart during systole and diastole. The pressure drop can be measured in resting condition or/and in hyperemia. The appearance of the flow peak can be located anywhere in the heart cycle and the ratio of the distal pressure (Pd) and the aortic pressure (Pa) can be measured at this point (or several points/samples of the neighborhood at this point). If pressure drop is of interest, the difference (Pa−Pd) is measured at the same point/points. As shown in FIG. 18, the Paortic curve shows a Pa value at a peak flow and a Pd value at the vertical double headed arrows for the cariac cycles shown. These values can be found and used to calculate FFR, pressure differences and other values on a per cardiac cycle basis at the peak flow or other specified flow threshold. In one embodiment, an arithmetic mean or other statistical or data metric (mean, median, mode, standard deviations, etc.) of the measured values are calculated over a number of heart beats. This ratio is Pd/Pa at the flow peak or other flow threshold. At baseline (if no hyperemia is introduced), this is the lowest Pd/Pa in the heart cycle and represents non-hyperemic resting indices.

Figure 16:
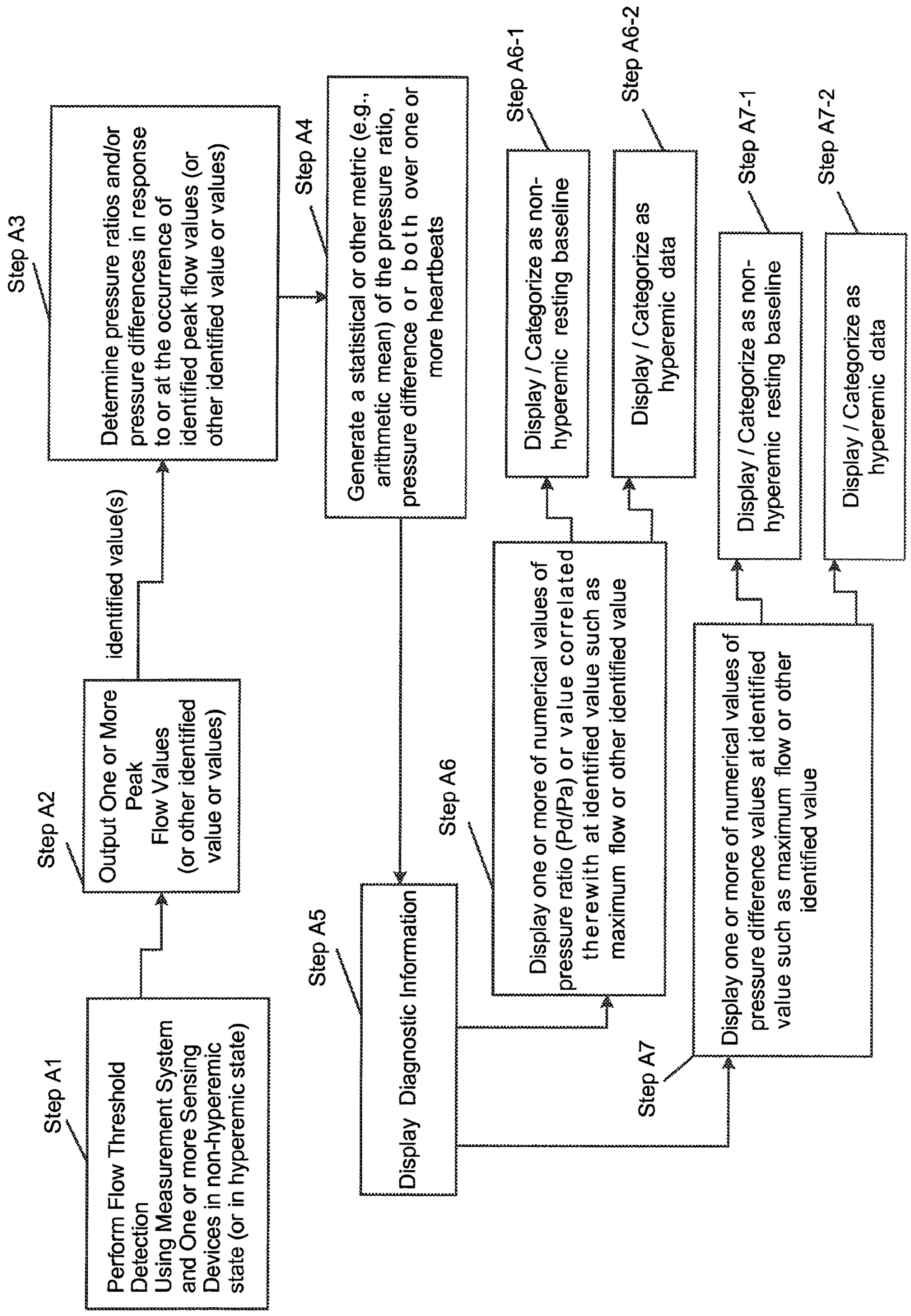
FIG. 16 is diagnostic method relating to flow threshold detection in accordance with an illustrative embodiment of the disclosure.

FIG. 16 is a series of methods steps for a diagnostic method such a blood vessel or stenosis assessment method that uses a flow threshold and other measured intravascular parameters. As one step of the method, performing flow threshold detection using an interface or other intravascular measurement system and one or more sensing devices in non-hyperemic state (or in hyperemic state) is undertaken (Step A1). As a result, a sensing device or system component can output one or more peak flow values (or other identified value or values) (Step A2). Further, the system and associated control logic can determine pressure ratios and/or pressure differences in response to or at the occurrence of identified peak flow values (or other identified value or values) (Step A3). Using such pressure ratios or differences, the system can generate a statistical or other metric (e.g., arithmetic mean, mode, deviation, or other metric or statistical value) of the pressure ratio, pressure difference, or both over one or more heartbeats (Step A4).

In turn, the system can then display or output diagnostic information (Step A5) such as plots or ratios or differences obtained at a flow threshold such as peak or maximum flow. Flow values can be generated using an intravascular sensor and can be used to provide an input to the system to select the flow threshold. The system can display one or more of numerical values of pressure ratio (Pd/Pa) or value correlated therewith at identified value such as maximum flow or other identified value (Step A6). The system can display/categorize the output as non-hyperemic resting baseline (Step A6-1) if the data was collected in a non-hyperemic state. The system can display/categorize the output as hyperemic data (Step A6-2) is a hyperemic agent was used. In addition, the system can display one or more of numerical values of pressure difference values at identified value such as maximum flow or other identified value (Step A7). The system can display/categorize the output as non-hyperemic resting baseline (Step 7-1). The system can display/categorize the output as hyperemic data (Step 7-2).

Figure 17A:
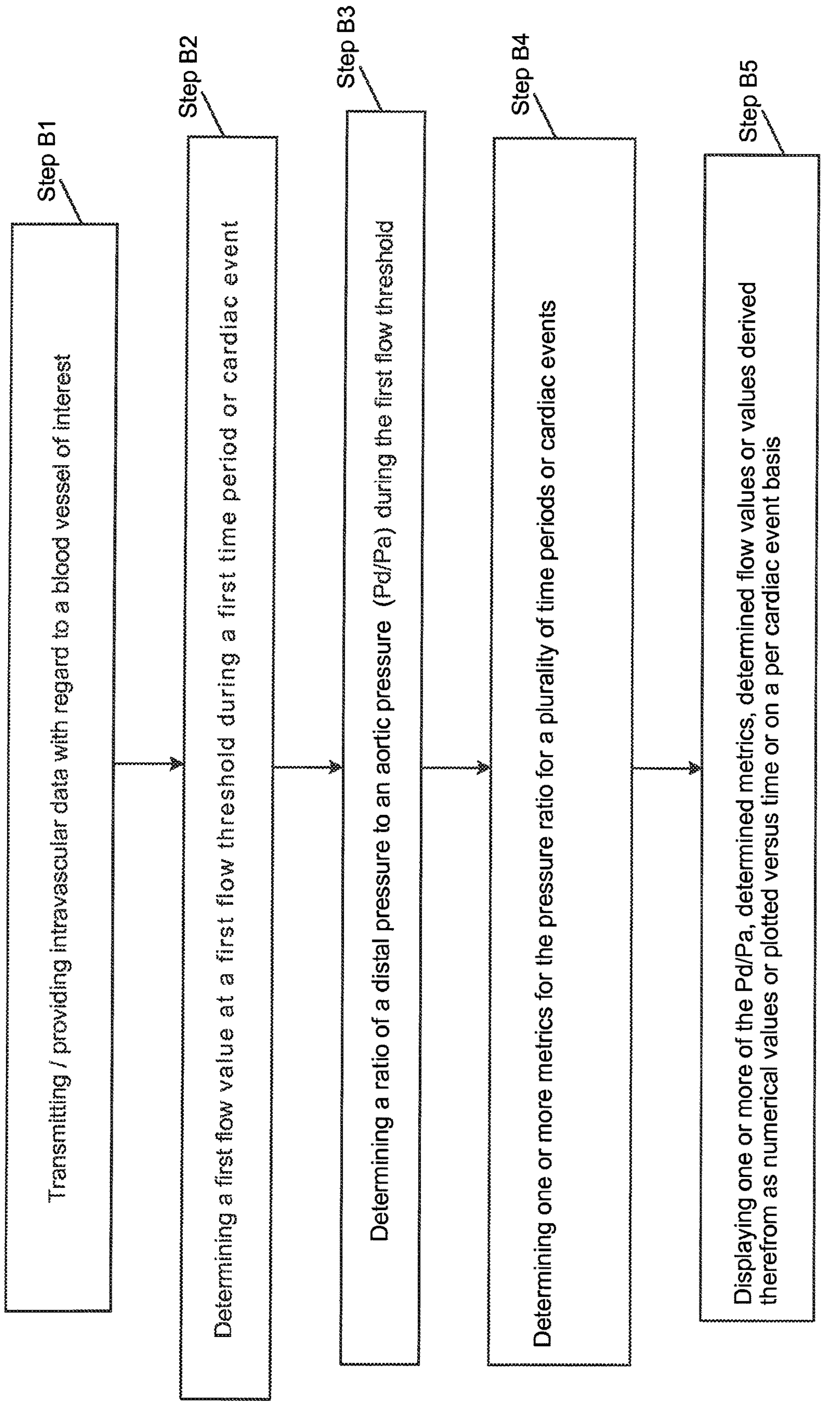
FIGS. 17A and 17B are flow charts depicting method embodiments relating to intravascular data collection, analysis and display of diagnostic information of interest in accordance with an illustrative embodiment of the disclosure.

FIG. 17A is another embodiment of a diagnostic method relating to pressure value ratios suitable for use with one or more of the pressure and flow sensing systems described herein. In FIG. 17A, various steps are outlined relating to a Pd/Pa ratio as shown. Initially, the system is used for transmitting/providing intravascular data with regard to a blood vessel of interest (Step B1). Next, the step of determining a first flow value at a first flow threshold during a first time period or cardiac event (Step B2) is performed. Determining a ratio of a distal pressure to an aortic pressure (pd/pa) during the first flow threshold (Step B3) is performed. In addition, the system can be setup for determining one or more metrics for the pressure ratio for a plurality of time periods or cardiac events (Step B4). The system can then display one or more of the pd/pa, determined metrics, determined flow values or values derived therefrom as numerical values or plotted versus time or on a per cardiac event basis (Step B5). FIG. 18 shows an exemplary output display from the method of FIG. 17A or a plot suitable for depicting flow thresholds and Pa and Pd values found at such thresholds such as the Pa and Pd value shown along vertical line A for the first cardiac cycle A.

Figure 17B:
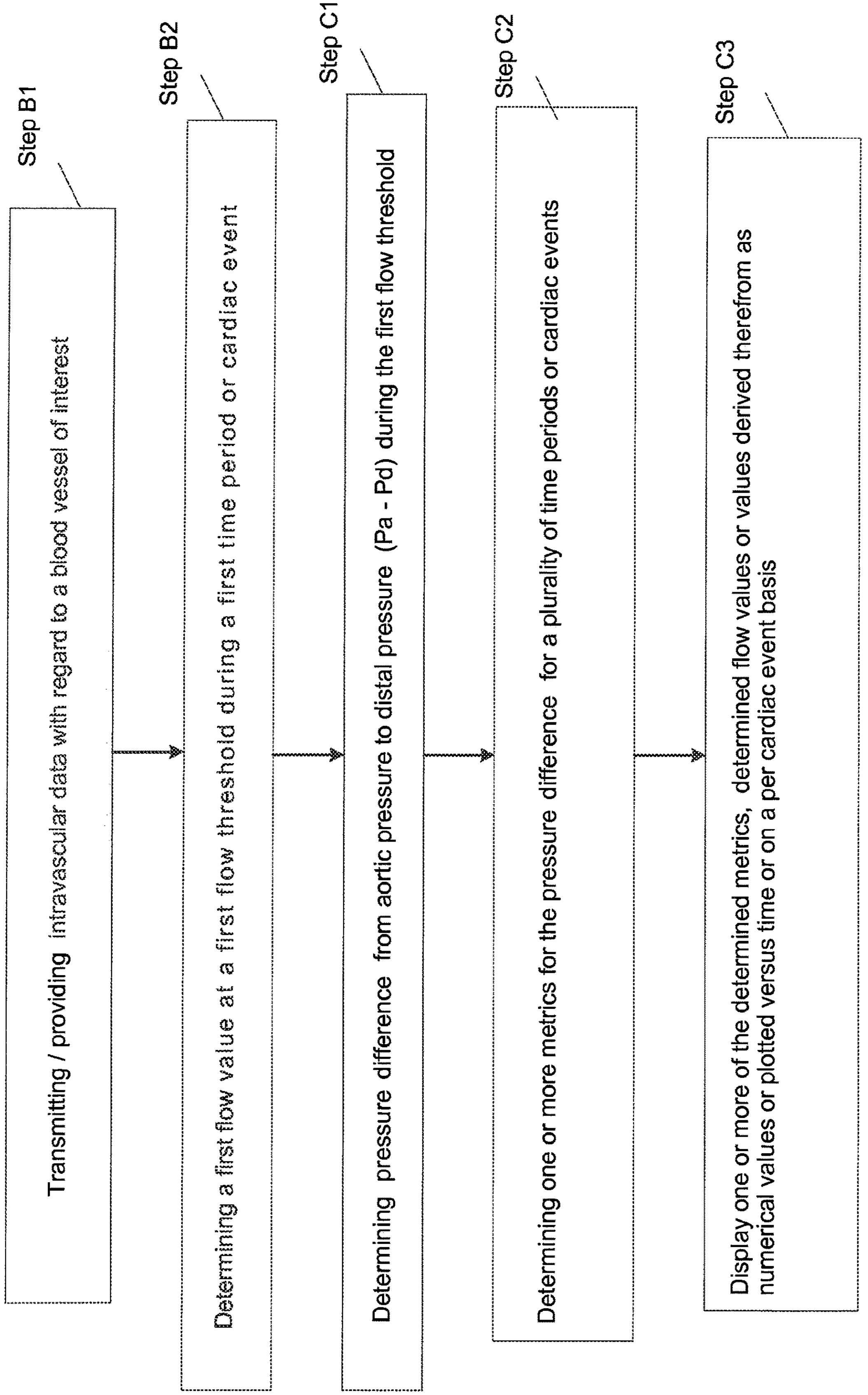

FIG. 17B is another embodiment of a diagnostic method relating to pressure value ratios suitable for use with one or more of the pressure and flow sensing systems described herein. In FIG. 17B, various steps are outlined relating to a diagnostic method relating to pressure differences for an intravascular pressure value and another pressure value of interest. The system can be used to perform the step of transmitting/providing intravascular data with regard to a blood vessel of interest (Step B1). As another step, determining a first flow value at a first flow threshold during a first time period or cardiac event (Step B2) can be performed. The flow values measured with a flow sensor such as using temperature and voltage as described herein can be used to select the flow threshold at which measurements will be obtained. Determining pressure difference from aortic pressure to distal pressure (pa−pd) during the first flow threshold (Step C1) can be performed.

As another step, determining one or more metrics for the pressure difference for a plurality of time periods or cardiac events (Step C2) can be performed such as by user selection or a predetermined selection in the system. The system displays one or more of the determined metrics, determined flow values or values derived therefrom as numerical values or plotted versus time or on a per cardiac event basis (Step C3). FIG. 18 shows an exemplary output display from the method of FIG. 17B.

With regard to FIG. 18, two plots or tracings are generated using measured intravascular data such as through one or more of the methods of FIGS. 16, 17A and 17B. Plot 910 (top of figure) and plot 920 (bottom of figure) show pressure versus time and flow values versus time respectively for cardiac cycles A-E. That is, a series of pressure curves versus time are shown over multiple cardiac cycles. In the top figure, plot 910, the solid line corresponds to the upper curve and shows aortic pressure rising and falling over time as the heart goes through a series of cardiac cycles. The lower pressure curve corresponds to the distal pressure measured in the blood vessel shown by the dotted lines 100A, 100B, 100C, 100D, and 100E corresponding to the flow thresholds. The Pd and Pa values can be found at the intersection of the double headed arrows and used to determine a first parameter such as Pd—Pa or Pd/Pa or a second parameter otherwise correlated with the first parameter.

Each vertical dotted line labelled A through E indicate a flow threshold at which data is collected and diagnostic data is generated on per cardiac cycle basis. The vertical line shown corresponds to a maximum flow. However, other flow thresholds can be used such as X % of maximum flow wherein X ranges from about 1 to about 100. There are five cardiac cycles A-E shown. The pressure differences shown by the double-headed arrows and identified as PD-A, PD-B, PD-C, PD-D, and PD-E are the pressure differences or pressure ratios determined at the associated time slice shown by the dotted vertical lines corresponding to a flow threshold selected by the system. As shown herein, a max or peak flow was the basis for the flow threshold used to determine where to measure the pressure ratios or pressure differences. The flow thresholds shown by the vertical lines can be selected as a max flow value on a per cycle basis as determined using the temperature based flow measurements described herein or other flow sensors.

For the five heartbeats shown, the double-headed vertical arrows correspond to the difference between the first pressure and the second pressure. The double-headed arrows are aligned with the vertical dotted lines that span the top figure and also continue down to the bottom figure. These dotted lines indicate the occurrence of a flow threshold such as peak flow. These dotted lines can be set using a control system and other flow threshold values of interest such as measured flow values or other values correlated therewith. The diagnostic values or plots thereof that can be determined at a flow threshold and displayed include without limitation one or more fractional flow reserve (FFR) values, coronary flow reserve (CFR) values, coronary flow velocity reserve (CFVR) values, instantaneous flow reserve (IFR) values, and one or more index of myocardial resistance (IMR) values.

The various pressure differences and pressure issues described herein can be displayed as numerical values for use during the diagnostic procedure or other procedures. These differences and ratios can also be used to generate various metrics such statistical values and other metrics. Examples of such statistical values include weighted average, average, arithmetic mean, mode frequency, median, standard deviations from a parameter such as a baseline (whether hyperemic or otherwise), and another statistical values relating to intravascular and coronary system parameters.

Non-Limiting Software Features and Embodiments for Implementing Pressure and Flow Related Data Collection and Analysis Methods and Systems The following description is intended to provide an overview of device hardware and other operating components suitable for performing the methods of the disclosure described herein. This description is not intended to limit the applicable environments or the scope of the disclosure. Similarly, the hardware and other operating components may be suitable as part of the apparatuses described above. The disclosure can be practiced with other system configurations, including personal computers, multiprocessor systems, microprocessor-based or programmable electronic device, network PCs, minicomputers, mainframe computers, and the like. The disclosure can also be practiced in distributed computing environments where tasks are performed by remote processing devices that are linked through a communications network such as in different rooms of a catheter or cath lab.

Some portions of the detailed description are presented in terms of algorithms and symbolic representations of operations on data bits within a computer memory. These algorithmic descriptions and representations can be used by those skilled in the computer and software related fields. In one embodiment, an algorithm is here, and generally, conceived to be a self-consistent sequence of operations leading to a desired result. The operations performed as methods stops or otherwise described herein are those requiring physical manipulations of physical quantities. Usually, though not necessarily, these quantities take the form of electrical or magnetic signals capable of being stored, transferred, combined, transformed, compared, and otherwise manipulated.

Unless specifically stated otherwise as apparent from the following discussion, it is appreciated that throughout the description, discussions utilizing terms such as “processing” or “computing” or “searching” or “detecting” or “measuring” or “calculating” or “comparing” “generating” or “sensing” or “determining” or “displaying,” or Boolean logic or other set related operations or the like, refer to the action and processes of a computer system, or electronic device, that manipulates and transforms data represented as physical (electronic) quantities within the computer system’s or electronic devices’ registers and memories into other data similarly represented as physical quantities within electronic memories or registers or other such information storage, transmission or display devices.

The present disclosure, in some embodiments, also relates to apparatus for performing the operations herein. This apparatus may be specially constructed for the required purposes, or it may comprise a general purpose computer selectively activated or reconfigured by a computer program stored in the computer. Various circuits and components thereof can be used to perform some of the data collection and transformation and processing described herein.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems will appear from the description below. In addition, the present disclosure is not described with reference to any particular programming language, and various embodiments may thus be implemented using a variety of programming languages.

Embodiments of the disclosure may be embodied in many different forms, including, but in no way limited to, computer program logic for use with a processor (e.g., a microprocessor, microcontroller, digital signal processor, or general purpose computer), programmable logic for use with a programmable logic device, (e.g., a Field Programmable Gate Array (FPGA) or other programmable logic device), discrete components, integrated circuitry (e.g., an Application Specific Integrated Circuit (ASIC)), or any other means including any combination thereof. In a typical embodiment of the present disclosure, some or all of the processing of the data collected using an OCT probe and the processor-based system is implemented as a set of computer program instructions that is converted into a computer executable form, stored as such in a computer readable medium, and executed by a microprocessor under the control of an operating system. Thus, query, response, transmitted probe data, input data and other data and signal described herein are transformed into processor understandable instructions suitable for generating pressure and flow data, detecting stenosis, determining max flow values, calibrating using a CVEX-based transfer function, calibrating using a CTA-based transfer function, determining max flow values, determining CFR values, determining FFR values; displaying and plotting data and parameters as described herein such in regions of a GUI and otherwise performing analysis and comparisons based on pressure versus flow curves and flow measurements, and other features and embodiments described above. Data and parameters suitable for display as plotted curve, values, or as another representation in a graphical user interface can include without limitation fractional flow reserve (FFR) values, coronary flow reserve (CFR) values, coronary flow velocity reserve (CFVR) values, instantaneous flow reserve (IFR) values, flow thresholds, averages of flow thresholds, and index of myocardial resistance (IMR) values.

Computer program logic implementing all or part of the functionality previously described herein may be embodied in various forms, including, but in no way limited to, a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies (e.g., Bluetooth), networking technologies, and internetworking technologies. The computer program may be distributed in any form as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Various examples of suitable processing modules are discussed below in more detail. As used herein a module refers to software, hardware, or firmware suitable for performing a specific data processing or data transmission task. Typically, in a preferred embodiment a module refers to a software routine, program, or other memory resident application suitable for receiving, transforming, routing and processing instructions, or various types of data such as resistance changes, guide wire-based probe data, temperature data, intravascular flow data, intravascular pressure data, transfer function outputs calibration data, excitation voltages, and other information of interest.

Computers and computer systems described herein may include operatively associated computer-readable media such as memory for storing software applications used in obtaining, processing, storing and/or communicating data. It can be appreciated that such memory can be internal, external, remote or local with respect to its operatively associated computer or computer system.

Memory may also include any means for storing software or other instructions including, for example and without limitation, a hard disk, an optical disk, floppy disk, DVD (digital versatile disc), CD (compact disc), memory stick, flash memory, ROM (read only memory), RAM (random access memory), DRAM (dynamic random access memory), PROM (programmable ROM), EEPROM (extended erasable PROM), and/or other like computer-readable media.

In general, computer-readable memory media applied in association with embodiments of the disclosure described herein may include any memory medium capable of storing instructions executed by a programmable apparatus. Where applicable, method steps described herein may be embodied or executed as instructions stored on a computer-readable memory medium or memory media. These instructions may be software embodied in various programming languages such as C++, C, Java, and/or a variety of other kinds of software programming languages that may be applied to create instructions in accordance with embodiments of the disclosure.

A storage medium may be non-transitory or include a non-transitory device. Accordingly, a non-transitory storage medium or non-transitory device may include a device that is tangible, meaning that the device has a concrete physical form, although the device may change its physical state. Thus, for example, non-transitory refers to a device remaining tangible despite this change in state.

The aspects, embodiments, features, and examples of the disclosure are to be considered illustrative in all respects and are not intended to limit the disclosure, the scope of which is defined only by the claims. Other embodiments, modifications, and usages will be apparent to those skilled in the art without departing from the spirit and scope of the claimed disclosure.

The use of headings and sections in the application is not meant to limit the disclosure; each section can apply to any aspect, embodiment, or feature of the disclosure.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions may be conducted simultaneously.

Where a range or list of values is provided, each intervening value between the upper and lower limits of that range or list of values is individually contemplated and is encompassed within the disclosure as if each value were specifically enumerated herein. In addition, smaller ranges between and including the upper and lower limits of a given range are contemplated and encompassed within the disclosure. The listing of exemplary values or ranges is not a disclaimer of other values or ranges between and including the upper and lower limits of a given range.

It is to be understood that the figures and descriptions of the disclosure have been simplified to illustrate elements that are relevant for a clear understanding of the disclosure, while eliminating, for purposes of clarity, other elements. Those of ordinary skill in the art will recognize, however, that these and other elements may be desirable. However, because such elements are well known in the art, and because they do not facilitate a better understanding of the disclosure, a discussion of such elements is not provided herein. It should be appreciated that the figures are presented for illustrative purposes and not as construction drawings. Omitted details and modifications or alternative embodiments are within the purview of persons of ordinary skill in the art.

It can be appreciated that, in certain aspects of the disclosure, a single component may be replaced by multiple components, and multiple components may be replaced by a single component, to provide an element or structure or to perform a given function or functions. Except where such substitution would not be operative to practice certain embodiments of the disclosure, such substitution is considered within the scope of the disclosure.

The examples presented herein are intended to illustrate potential and specific implementations of the disclosure. It can be appreciated that the examples are intended primarily for purposes of illustration of the disclosure for those skilled in the art. There may be variations to these diagrams or the operations described herein without departing from the spirit of the disclosure. For instance, in certain cases, method steps or operations may be performed or executed in differing order, or operations may be added, deleted or modified.

What is claimed is:

1. A method of intravascular pressure and flow monitoring comprising:

measuring a plurality of intravascular blood flow values, a plurality of proximal blood pressure values, and a plurality of distal blood pressure values during each of a plurality of heart cycles using one or more sensors, wherein:

the one or more sensors are part of an intravascular guide wire-based probe disposed on a distal end of a guidewire, the one or more sensors comprising:

an active resistor that is sensitive to temperature and pressure, and a passive resistor that is sensitive to temperature but is not sensitive to pressure;

the plurality of distal blood pressure values are measured by performing steps comprising:

processing a first electrical signal associated with the active resistor and the passive resistor, and determining the distal blood pressure values based on the first electrical signal, and the plurality of intravascular blood flow values are measured by performing steps comprising:

processing a second electrical signal associated with the passive resistor, and determining the intravascular blood flow values using a transfer function based on the second electrical signal;

receiving, at a control system, the plurality of intravascular blood flow values, the plurality of proximal blood pressure values, and the plurality of distal blood pressure values;

determining, with the control system, a plurality of flow thresholds, including a flow threshold for each of the plurality of heart cycles, using the plurality of intravascular blood flow values;

determining, with the control system, a proximal blood pressure value and a distal blood pressure value at a time of each flow threshold;

calculating, with the control system, a diagnostic parameter based on the proximal blood pressure value and the distal blood pressure value at the time of each flow threshold; and causing, with the control system, a display to display the diagnostic parameter for the plurality of heart cycles.

2. The method of claim 1, wherein:

the diagnostic parameter is a pressure difference of the proximal blood pressure value minus the distal pressure value at the time of each flow threshold.

3. The method of claim 1, wherein:

the diagnostic parameter is a pressure ratio of the distal blood pressure value over the proximal pressure value at the time of each flow threshold.

4. The method of any of claims 1-3, wherein:

each proximal blood pressure value is a proximal blood pressure value measured relative to a stenosis.

5. The method of any of claims 1-3, wherein:

each proximal blood pressure value is an aortic pressure value.

6. The method of claim 1, wherein:

each flow threshold is selected from the group consisting of a maximum flow, a relative extremum flow value, and a fraction of the maximum flow.

7. The method of claim 1, wherein:

calculating the diagnostic parameter comprises calculating an average of pressure ratios or pressure differences for the plurality of heart cycles per a determined flow threshold for the plurality of heart cycles.

8. The method of claim 1, wherein the diagnostic parameter is a mean of pressure ratios for the plurality of heart cycles or a mean of pressure differences for the plurality of heart cycles.

* * * * *